(12) United States Patent
Liang et al.

(10) Patent No.: US 7,576,191 B2
(45) Date of Patent: Aug. 18, 2009

(54) TUMOR SUPPRESSOR KILLIN

(75) Inventors: Peng Liang, Nashville, TN (US);
Yong-jig Cho, Brentwood, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 11/519,193

(22) Filed: Sep. 11, 2006

(65) Prior Publication Data
US 2007/0072218 A1    Mar. 29, 2007

Related U.S. Application Data

(60) Provisional application No. 60/716,691, filed on Sep. 13, 2005.

(51) Int. Cl.
*C07H 21/02*    (2006.01)

(52) U.S. Cl. ..................... 536/23.1; 536/23.4

(58) Field of Classification Search ............ None
See application file for complete search history.

(56) References Cited

U.S. PATENT DOCUMENTS

2004/0234973 A1 *  11/2004  Adorjan et al. ............... 435/6

OTHER PUBLICATIONS

Kim et al, GenEmbl submission-SEQ ID No. 2, Aug. 5, 2001.*
Kim et al (GenEmbl submission- SEQ ID No. 1, Aug. 5, 2001.*
Liang and Pardee, "Analysing differential gene expression in cancer," *Nature Reviews*, 3:869-876, 2003.

* cited by examiner

*Primary Examiner*—Larry R. Helms
*Assistant Examiner*—Mark Halvorson
(74) *Attorney, Agent, or Firm*—Fulbright & Jaworski, LLP

(57) ABSTRACT

The present invention relates to a new tumor suppressor, designated Killin. Also described are diagnostic and therapeutic uses of the Killin protein and the killin gene, alone or in combination with traditional cancer therapies.

5 Claims, 17 Drawing Sheets

MDRPGPGSARPGRTVHVWGYRVEWKVRNGRKLQPSEWAGRGDLGGFKRRWKDTRATVGT-
TFRRRSRVSLVGELSKFPLPSDSSGGKSSSSFARGALAWCRQRNPNPSCAAAETGARSLP-
KERCRGWRLGNWLHKHPHPNTCPRLPACWLPPILTERGERVPKLVPLLACYPKSKPKD

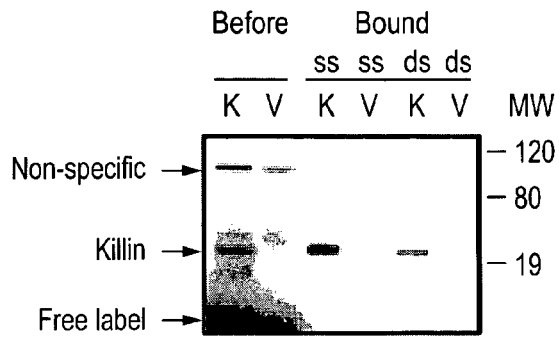
FIG. 6A
| | | Colony formation |
|---|---|---|
| 1 [===================================] 178 | | − |
| 1 [=======================] 123 | | − |
| 124 [==========] 178 | | + |
| 1 [==================] 97 | | − |
| 1 [================] 85 | | − |
| 1 [=========] 49 | | − |
| 1 [========] 43 | | + |
| 1 [=======] 36 | | + |
| 1 [======] 32 | | + |
| 1 [====] 23 | | + |
| 1 [===] 17 | | + |
| 8 [====] 49 | | − |
| 11 [===] 49 | | + |
FIG. 6B
ARPGRTVHVWGYRVEWKVRNGRKLQPSEWAGRGDLDDFKRRW
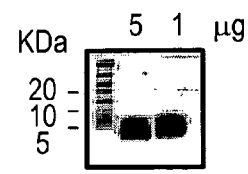
FIG. 6C

TUMOR SUPPRESSOR KILLIN

The present application claims benefit of priority to U.S. Provisional Application Ser. No. 60/716,691, filed Sep. 13, 2005, the entire contents of which are hereby incorporated by reference.

This invention was made with government support under grant number RO1 CA105024 awarded by the National Institutes of Health. The government has certain rights in the invention.

BACKGROUND OF THE INVENTION

I. Field of the Invention

The present invention relates to the fields of oncology, genetics and molecular biology. More particular the invention relates to the identification, on human chromosome 10, of a p53-related tumor suppressor gene designated as Killin.

II. Related Art

Oncogenesis is a multistep biological process, which is presently known to occur by the accumulation of genetic damage. On a molecular level, the process of tumorigenesis involves the disruption of both positive and negative regulatory effectors (Weinberg, 1989). The molecular basis for human colon carcinomas has been postulated, by Vogelstein and coworkers (1990), to involve a number of oncogenes, tumor suppressor genes and repair genes. Similarly, defects leading to the development of retinoblastoma have been linked to another tumor suppressor gene (Lee et al., 1987). Still other oncogenes and tumor suppressors have been identified in a variety of other malignancies. Unfortunately, there remains an inadequate number of treatable cancers, and the effects of cancer are catastrophic—over half a million deaths per year in the United States alone.

p53 is the most frequently mutated, disrupted, and/or allelically lost tumor suppressor gene in human cancer, and it has been a focal point for intensive cancer research (Levine, 1997; Vogelstein et al., 2000; Vousden and Prives, 2005). Functionally, p53 works as a sequence dependent transcription factor, which upon activation by genotoxic stresses such as DNA damages regulates the expression of a set of target genes that are involved in cell growth control and apoptosis (El-Deiry, 1998; Yu et al., 1999; Vousden and Lu, 2002; Liang and Pardee, 2003). In contrast to a large number of p53 target genes that were implicated in cell apoptosis, activation of cell cycle arrest at G1 by p53 results predominantly from the induction of p21 (Deng et al., 1995), whereas p21 as well as GADD45 and 14-3-3 proteins were also shown to be involved in G2-M arrest (Taylor and Stark, 2001). Among the known p53 target genes implicated in apoptosis, a family of Bcl-2 related genes, such as bax, puma and noxa, are the best characterized and thought to work through a mitochondria-dependent death pathway (Yu and Zhang, 2005).

Through a genetic approach using somatic gene knockout strategy, it was shown that cellular choice between growth arrest and death upon p53 activation appears to depend on at least two factors. For cell types that undergo p53-mediated G1 arrest, elimination of p21 sensitizes cells to die (Polyak et al., 1996; Yu et al., 2003). In such cases, p21 clearly plays a protective role in apoptosis. In cell types that are prone to apoptosis upon p53 activation, transacting death-inducing factors are dominant over p21-mediated protection (Polyak et al., 1996; Yu et al., 2003). In the case of p21-mediated G1 arrest which protects cells from p53 induced apoptosis, one possible explanation could be that the apoptosis initiating event(s) require cells to enter S-phase. Supporting evidence for such S-phase-coupled apoptosis include findings that forced S-phase entry by unrestricted E2F activity can trigger the activation of caspases and apoptosis (Nahle et al., 2002; Gottifredi and Prives, 2005). Conceivably, DNA damage can happen to cells at any phase during the cell cycle. The induction of either p21 in cells at G1, or p21, GADD45 and 14-3-3 at G2/M phase by p53 will lead to growth arrest at the respective cell cycle phases. However, little is known about p53-mediated checkpoint control during S-phase where cells would run the highest risk of incorporating mutations after sustained DNA damage. It is logical that apoptosis would be the best choice for eliminating these cells. summary of the invention

SUMMARY OF THE INVENTION

Thus, in accordance with the present invention, there is provided an isolated polynucleotide encoding a polypeptide having an amino acid sequence of SEQ ID NO:1 The polynucleotide may further have the nucleic acid sequence of SEQ ID NO:2 or a complement thereof. In addition, the polynucleotide may further comprise a promoter operable in eukaryotic cells. The promoter may be heterologous to the coding sequence, and may be selected from the group consisting of hsp68, SV40, CMV IE, MKC, GAL4$_{UAS}$, HSV and β-actin. The promoter may be a tissue specific promoter or inducible promoter.

Also provided is a nucleic acid of about 15 to about 5000 base pairs comprising from about 15 contiguous base pairs of SEQ ID NO:2, or the complement thereof. The nucleic acid may comprise about 15, 16, 17, 18, 19, 20, 21, 22, 23, 24, 25, 30, 40, 50, 60, 70, 80, 90, 100, 150, 250, 500, 1000, 2500, or 4000 contiguous base pairs of SEQ ID NO:2, or the complement thereof. The nucleic acid itself may be 15, 16, 17, 18, 19, 20, 21, 22, 23, 24, 25, 26, 27, 28, 29, 30, 35, 40, 45, 50, 55, 60, 65, 70, 75, 80, 85, 90, 95 100, 150, 200, 250, 300, 400, 500, 1000, 2000, 3000, 4000, or 5000 base pairs.

In another embodiment, there is provided a peptide comprising about 10-50 contiguous amino acids of SEQ ID NO:1, or more specifically, 15, 16, 17, 18, 19, 20, 21, 22, 23, 24, 25, 30, 35, 40, 45, or 50 contiguous amino acids of SEQ ID NO:1. The peptide may comprise residues 8-49 of SEQ ID NO:1, or the full length sequence of SEQ ID NO:1.

In yet another embodiment, there is provided an expression cassette comprising a polynucleotide encoding a polypeptide having the sequence of SEQ ID NO:1 or a fragment thereof, wherein the polynucleotide is under the control of a promoter operable in eukaryotic cells. The promoter may be heterologous to the coding sequence, and may be selected from the group consisting of hsp68, SV40, CMV IE, MKC, GAL4$_{UAS}$, HSV and β-actin. The promoter may be a tissue specific promoter or inducible promoter. The expression cassette may be contained in a viral vector, for example, a retroviral vector, an adenoviral vector, and adeno-associated viral vector, a vaccinia viral vector, and a herpesviral vector. The expression cassette may further comprise a polyadenylation signal, may further comprise a second polynucleotide encoding a second polypeptide which may be under the control of a second promoter.

In still yet another embodiment, there is provided a method for suppressing growth of a cancer cell comprising contacting the cells with an expression cassette comprising a polynucleotide encoding a polypeptide having the sequence of SEQ ID NO:1 or a fragment thereof, wherein the polynucleotide is under the control of a promoter operable in eukaryotic cells. The promoter may be heterologous to the polynucleotide sequence, such as hsp68, SV40, CMV, MKC, GAL4$_{UAS}$, HSV and β-actin. The may be tissue specific promoter or an inducible promoter. The expression cassette may be contained in a viral vector, for example, a retroviral vector, an adenoviral vector, and adeno-associated viral vector, a vaccinia viral vector, and a herpesviral vector. The expression cassette may further comprise a polyadenylation signal, a second polynucleotide encoding a second polypeptide which may be under the control of a second promoter.

In an additional embodiment, there is provided a cell comprising an expression cassette comprising a polynucleotide encoding a polypeptide having the sequence of SEQ ID NO:1 or a fragment thereof, wherein the polynucleotide is under the control of a promoter operable in eukaryotic cells.

In still an additional embodiment, there is provided a monoclonal antibody that binds immunologically to a polypeptide having the sequence of SEQ ID NO:1, or an immunologic fragment thereof. The antibody may further comprise a detectable label, for example, a fluorescent label, a chemiluminescent label, a radiolabel and an enzyme.

In another embodiment, there is provided a hybridoma cell that produces a monoclonal antibody that binds immunologically to a polypeptide having the sequence of SEQ ID NO:1, or an immunologic fragment thereof. Also provided is a polyclonal antisera, antibodies of which bind immunologically to a polypeptide having the sequence of SEQ ID NO:1, or an immunologic fragment thereof.

In still another embodiment, there is provided a method of diagnosing a cancer comprising the steps of (i) obtaining a tissue sample from a subject; and (ii) assessing the expression or structure of Killin in cells of the sample. The cancer may be selected from the group consisting of brain, lung, liver, spleen, kidney, lymph node, small intestine, pancreas, blood cells, colon, stomach, breast, endometrium, prostate, testicle, ovary, skin, head and neck, esophagus, bone marrow and blood cancer. The method may comprise assessing Killin expression or Killin structure. The sample may be a tissue or fluid sample. Assessing may comprise assaying for a Killin-encoding nucleic acid from the sample, such as by subjecting the sample to conditions suitable to amplify the nucleic acid. Assessing may comprise contacting the sample with an antibody that binds immunologically to a Killin polypeptide, such as by ELISA. Assessing may comprise evaluating the level of Killin expression, for example, by comparing the expression of Killin with the expression of Killin in non-cancer samples. Assessing may comprise evaluating the structure of the Killin gene or transcript, for example, by sequencing, wild-type oligonucleotide hybridization, mutant oligonucleotide hybridization, SSCP, PCR and RNase protection, including use of an array on a chip or wafer.

In still another embodiment, there is provided a method for altering the phenotype of a tumor cell comprising the step of administering to a cell a tumor suppressor designated Killin or a fragment thereof under conditions permitting the uptake of the tumor suppressor by the tumor cell. The tumor cell may be derived from a tissue selected from the group consisting of brain, lung, liver, spleen, kidney, lymph node, small intestine, blood cells, pancreas, colon, stomach, breast, endometrium, prostate, testicle, ovary, skin, head and neck, esophagus, bone marrow and blood tissue. The phenotype may be selected from the group consisting of apoptosis, angiogenesis, proliferation, migration, contact inhibition, soft agar growth and cell cycling. The tumor suppressor may be is encapsulated in a liposome.

A further embodiment comprises a method for altering the phenotype of a tumor cell comprising the step of contacting the cell with a nucleic acid (i) encoding a tumor suppressor designated Killin or a fragment thereof and (ii) a promoter active in the tumor cell, wherein the promoter is operably linked to the region encoding the tumor suppressor, under conditions permitting the uptake of the nucleic acid by the tumor cell. The tumor cell may be derived from a tissue selected from the group consisting of brain, lung, liver, spleen, kidney, lymph node, small intestine, blood cells, pancreas, colon, stomach, breast, endometrium, prostate, testicle, ovary, skin, head and neck, esophagus, bone marrow and blood tissue. The phenotype may be selected from the group consisting of apoptosis, angiogenesis, proliferation, migration, contact inhibition, soft agar growth or cell cycling. The nucleic acid may be encapsulated in a liposome. The nucleic acid may comprise a viral vector selected from the group consisting of retrovirus, adenovirus, adeno-associated virus, vaccinia virus and herpesvirus. The nucleic acid may be encapsulated in a viral particle.

Yet another embodiment provides a method for treating subject with cancer comprising the step of administering to the subject a tumor suppressor designated Killin or a fragment thereof. The tumor cell may be derived from a tissue selected from the group consisting of brain, lung, liver, spleen, kidney, lymph node, small intestine, blood cells, pancreas, colon, stomach, breast, endometrium, prostate, testicle, ovary, skin, head and neck, esophagus, bone marrow and blood tissue. The subject may be a human. The method may further comprise treating the subject with a second anti-cancer therapy, such as radiation therapy, gene therapy, hormonal therapy, immunotherapy, toxin therapy or surgery. The gene therapy may be p53 gene therapy.

In still another embodiment, there is provided a method for treating a subject with cancer comprising the step of administering to the subject a nucleic acid (i) encoding a tumor suppressor designated Killin or a fragment thereof and (ii) a promoter active in eukaryotic cells, wherein the promoter is operably linked to the region encoding the tumor suppressor. The tumor cell may be derived from a tissue selected from the group consisting of brain, lung, liver, spleen, kidney, lymph node, small intestine, blood cells, pancreas, colon, stomach, breast, endometrium, prostate, testicle, ovary, skin, head and neck, esophagus, bone marrow and blood tissue. The subject may be a human. The method may further comprise treating the subject with a second anti-cancer therapy, such as radiation therapy, gene therapy, hormonal therapy, immunotherapy, toxin therapy or surgery. The gene therapy may be p53 gene therapy.

In a further embodiment, there is provided a non-human transgenic eukaryote lacking a functional Killin gene, for example, wherein the eukaryote is a mammal. Another embodiment is a non-human transgenic eukaryote that overexpresses Killin as compared to a similar non-transgenic eukaryote, for example, wherein the eukaryote is a mammal.

A method of screening a candidate substance for anti-tumor activity comprising the steps of (i) providing a cell lacking functional Killin polypeptide; (ii) contacting the cell with the candidate substance; and (iii) determining the effect of the candidate substance on the cell. The cell may be a tumor cell, such as a tumor cell having a mutation in the coding region of Killin. The mutation may be a deletion mutant, an insertion mutant, a frameshift mutant, a nonsense mutant, a missense mutant or splice mutant. Determining may comprise comparing one or more characteristics of the cell in the presence of the candidate substance with characteristics of a cell in the absence of the candidate substance. The characteristic may be selected from the group consisting of proliferation, metastasis, apoptosis, contact inhibition, soft agar growth, cell cycle regulation, tumor formation, tumor progression and tissue invasion. The candidate substance may be a chemotherapeutic or radiotherapeutic agent, or selected from a small molecule library. The may be contacted in vitro or in vivo.

In still yet another embodiment, there is provided an isolated and purified nucleic acid that hybridizes, under high stringency conditions, to a DNA segment comprising SEQ ID NO:2.

Another embodiment comprises a method of screening a candidate substance for anti-tumor activity comprising the steps of (i) providing a cell expression a functional Killin peptide or polypeptide; (ii) contacting the cell with the candidate substance; and (iii) determining Killin DNA binding or nuclear localizaion, wherein an increase in Killin DNA binding or nuclear localization, as compared to a similar cell not treated with the candidate substance, indicates that the candidate substance has anti-tumor activity.

In yet an additional embodiment, there is provided a nucleic acid segment comprising SEQ ID NO:3. Also provided is a method of screening for an activator of Killin expression comprising (i) providing a cell comprising a Killin promoter operably linked to a nucleic acid segment encoding expressible marker; (ii) contacting said cell with a candidate substance; and (iii) assessing the expression of said marker, wherein an increase in expression of said marker, as compared to expression in a cell not contacted with said candidate substance, identifies said candidate substance as an activator of Killin expression. The cell may be a eukaryotic cell. The candidate substance may be a protein, a peptide, an organopharmaceutical, a lipid, a carbohydrate or a nucleic acid. The expressible marker may be an enzyme or a fluorescent or chemiluminescent protein.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein:

(FIG. 1A) Identification of killin by FDD. p53-3, a H1299 lung cancer cell line with a Tet-repressible p53 expression construct was either uninduced (+tet) or induced (−tet) for wild-type p53 for the time points indicated. p53 dependent expression of killin (G101) was detected by FDD with a G-anchored primer and arbitrary primer HAP-101 (indicated by arrow). (FIG. 1B) Northern Blot confirmation. killin cDNA was recovered from the FDD gel, cloned and used as a probe for Northern blot confirmation of its induction by p53 which was verified by western blot analysis. rRNA loading control was shown as the bottom panel. (FIG. 1C) p53 dependence of killin expression. To rule out the effect of tetracycline, parental H1299 cell line (p53 null) was grown also in the absence of tet for 24 hours and compared for killin expression by Northern blot analysis with p53-3 cells (H1299 with inducible wt p53) either without (+tet) and with (−tet) p53 induction for the same duration. The induction of p53 protein was confirmed by western blot analysis. rRNA loading control was shown as the bottom panel. (FIG. 1D) Predicted amino acid sequence of Killin with putative nuclear localization sequence (NLS) underlined.

(FIG. 2A) Chromosomal locus of killin. The 194 bp intergenic region separating killin and pTEN contains a divergent promoter with a p53 consensus binding site (underlined). Note killin is encoded by a single exon of 4.1 kb, whereas pTEN is encoded by multiple exons and introns spanning over 100 kb (SEQ ID NO:4). (FIG. 2B) Luciferase reporter assays showing that the 140 bp killin promoter sequence containing the conserved p53 binding site (pGL3-Killin) conferred a dramatic p53-dependent transcription activation, whereas mutations at the key p53 consensus bases within the Kuhn promoter (pGL3-Killin-mutant) greatly decreased the p53 effect. Co-transfected vectors expressing either wild-type (pCep4-ps3wt) or a DNA binding mutant of p513 (R248W) (pCep4-ps3mut), as well as the vector control (pCep4) were as indicated.

(FIG. 3A) DLD-1 cell lines stably expressing either inducible GFP or GFP-Killin was visualized by fluorescence microscopy after 16 hrs of induction (−tet). Note that GFP-Killin is localized exclusively in the nucleus, whereas GFP is expressed throughout the cells. (FIG. 3B) pEGFP-C1 vector expressing an in-frame GFP-Killin fusion protein was transiently transfected into Cos-1 cells. One day (left panels) and three days (right panels) after transfection, cells expressing the GFP-Killin were visualized under a Zeiss fluorescent microscope (20×). Compared to nuclear staining with DAPI, GFP-Killin was clearly localized in the nucleus with focal distribution pattern (upper left). In apoptotic cells (upper right), GFP-Killin appeared to be associated with condensed apoptotic chromotin. (FIG. 3C) Confocal fluorescent microscopy. Cos-1 cells after transiently transfected with either GFP-PCNA or GFP-Killin for 16 hrs showed distribution pattern as nuclear foci.

(FIG. 4A) RNAi knockdown of killin expression blocks p53 induced Caspase-3 activation and PARP cleavage. p53-3 cells stably transfected with either pSuper-RNAi vector alone or pSuper-RNAi-killin were either non-induced (+tet) or induced (−tet) for 24 hrs. The induction of p53 and p21 were confirmed by Western blot analysis with β-actin as a control for equal sample loading. RNAi knockdown of killin expression in p53-3 cells led to not only diminished p53-dependent expression of killin mRNA as determined by real time RT-PCR, but also inhibition of Caspase-3 activation and cleavage of PARP analyzed by Western blot. RNAi knockdown of killin expression had little effect on p53 induction and its effect on p21 expression. (FIG. 4B) RNAi knockdown of killin expression blocks p53-mediated Apoptosis. FACS analysis of p53-3 cells stably transfected with either pSuper- RNAi-killin or pSuper vector control confirmed that blocking p53-dependent killin expression would essentially prevent cells from apoptosis, without affecting G1 arrest mediated by p21. The p53 induction time following tetracycline withdraw was as indicated. The results were representative of multiple clones of cells in duplicated experiments.

(FIG. 5A) Killin expression causes rapid inhibition in cell proliferation. Cell proliferation rate for DLD-1 cells with tetracycline regulated expression of either GFP-Killin or GFP alone were compared with (−tet) or without induction (+tet). Both attached (live) and detached (dying) cells were counted and combined for each time point as indicated. (FIG. 5B) Killin expression leads to rapid cell cycle arrest followed by massive cell apoptosis. FACS analysis of DLD-1 cells following inducible expression of GFP-Killin showed little decrease in S-phase DNA content or increase in G1 or G2/M DNA content during the first 48 hrs of GFP-Killin induction, when growth arrest became apparent (FIG. 5A). Massive apoptosis based on sub-G1 DNA content was apparent after 72 hrs post induction of GFP-Killin. (FIG. 5C) The induction of GFP and GFP-Killin were also visualized by fluorescence microscopy, whereas cells were depicted by phase-contrast. Note massive cell death (reflectory detached cells) induced by GFP-Killin (−tet) after 72 hrs, compared to either non-induced cells (+tet) or GFP alone induced cells during the same time period.

FIGS. 6A-D—Killin is a High Affinity DNA Binding Protein. (FIG. 6A) The full-length native Killin is a DNA binding protein. In vitro transcribed and translated Killin (K) or vector alone (V) were labeled with $^{35}$S and incubated with either single-stranded (ss) or double-stranded (ds) DNA cellulose. After washing with PBS, bound proteins were resolved on a 15% SDS-PAGE gel and visualized by autoradiography. Killin (20 Kda), but not the non-specific protein (100 Kda) from the vector alone was specifically retained by DNA cellulose. (FIG. 6B) Bacterial genetic screen and serial deletion analysis of the functional domain of Killin. pQE32 bacterial expression vectors encoding either the full-length N-terminal His-tagged Killin (1-178 aa), or truncated Killin as indicated were transformed into either XL-1 Blue (lac I$^q$ with repression) or GH1 (wild-type lac I without repression) competent cells and selected with ampicillin in the absence of IPTG. While all plasmids gave numerous colonies when transformed under repressed condition in XL-1 blue, Killin deletions that retained the ability to kill *E. coli* were scored for their ability to inhibit colony formation in GH1 cells. Similar deletion mutants of Killin were made into GFP fusion protein in pEGFP-C1 expression vector and transiently transfected into H1299 cells to score for their ability to induced cell apoptosis based on florescent microscopy of the nuclear condensation. (FIG. 6C) Amino acid sequence of Killin/N8-50 peptide with the minimum 8-49 aa residues underlined. The chemically synthesized Killin/N8-50 was analyzed on a 15% SDS PAGE by Coomassie Blue staining with the amount of peptide as indicated. (FIG. 6D) In vitro DNA binding kinetics of Killin/N8-50 peptide. $^{32-}$P end labeled double-stranded, single-stranded and artificial replication fork DNA templates of 32-35 bases or bp in length were each incubated with increasing concentration of Killin/N8-50 peptide as indicated. The reactions were resolved on a 6% TBE PAGE gel. The Killin-DNA binding kinetics was quantified by counting the radioactivity of the complex formed (upper retained band) from each reaction in duplicate.

(FIG. 7A) Killin/N8-50 and DNA forms a non-covalently linked stable complex. Equal amount (500 ng) of either double-stranded (replication form) or single-stranded (viral form) PhiX174 bacterial phage DNA was incubated with either 1 μg of BSA or Killin/N8-50 peptide. The stability of Killin-DNA complex, in the presence of either 6 M urea, 150 mM EDTA or 0.1% SDS as indicated, was then assessed on a 0.8% TAE agarose gel after ethidium bromide staining. (FIG. 7B) Inhibition of eukaryotic DNA replication in vitro by Killin/N8-50 peptide. The concentration of Killin/N8-50 peptide used was from 1, 1.6, 2.4, 3.2, 4.8, 6.4, 8 to 16 μM, as indicated.

DETAILED DESCRIPTION OF THE PREFERRED EMBODIMENTS

I. THE PRESENT INVENTION

The inventors have identified of a novel p53 target gene, killin, which encodes a small nuclear DNA binding protein with a high affinity to both double-stranded and single-stranded DNA. Killin is not only necessary, but sufficient for mediating p53-induced growth arrest and apoptosis. Genetic and biochemical analysis reveal that the DNA binding domain of Killin resides within 42 amino acid residues near the N-terminus of the protein which can inhibit DNA synthesis in vitro and S-phase arrest coupled to apoptosis in vivo. Thus, Killin represents the first p53 target gene that is directly involved in S-phase checkpoint control-coupled apoptosis. These findings also help to explain the apparent paradox of p21 being both a growth and death inhibitor, since G1 arrest triggered by p21 can prevent cells from S-phase entry, thereby escaping the fate of death through S-phase checkpoint control mediated by Killin.

Compelling evidence from cell biological, genetic and biochemical analysis of the gene suggests the following possible mechanism of action for Killin in mediating tumor-suppressor p53 functions. Upon induction by p53 during S-phase, Killin functions in the cell nucleus as a DNA synthesis inhibitor via its high affinity to both double-stranded and single-stranded DNA (e.g., at the replication forks) and thereby causes S-phase arrest, which in turn triggers subsequent cell apoptosis. Thus, Killin-mediated checkpoint control at S-phase would complement those at G1 mediated by p21, and G2-M phase by p21, GADD45 and 14-3-3, and provides a fool-proof mechanism for p53 in preventing precancerous cells from replicating their DNA content. Thus, Killin represents the first p53 target gene that is directly and functionally involved in S-phase checkpoint control which seems to be coupled to apoptosis, in contrast to p21 mediated G1 arrest, which is anti-apoptotic. The unique function of Killin in coupling S-phase arrest with apoptosis may also explain why p21-mediated G1 arrest can be anti-apoptotic. Conceivably, prevention of cells from S-phase entry by p21 would spare cells from Killin-mediated inhibition of DNA synthesis. Without stalled replication forks caused by Killin, apoptosis may be avoided. The high affinity of Killin to both double-stranded and single-stranded DNA could also reconcile with the diffusive focal distribution pattern of Killin in S-phase nuclei which undergo further condensation characteristic of apoptotic cells.

Figure 9:
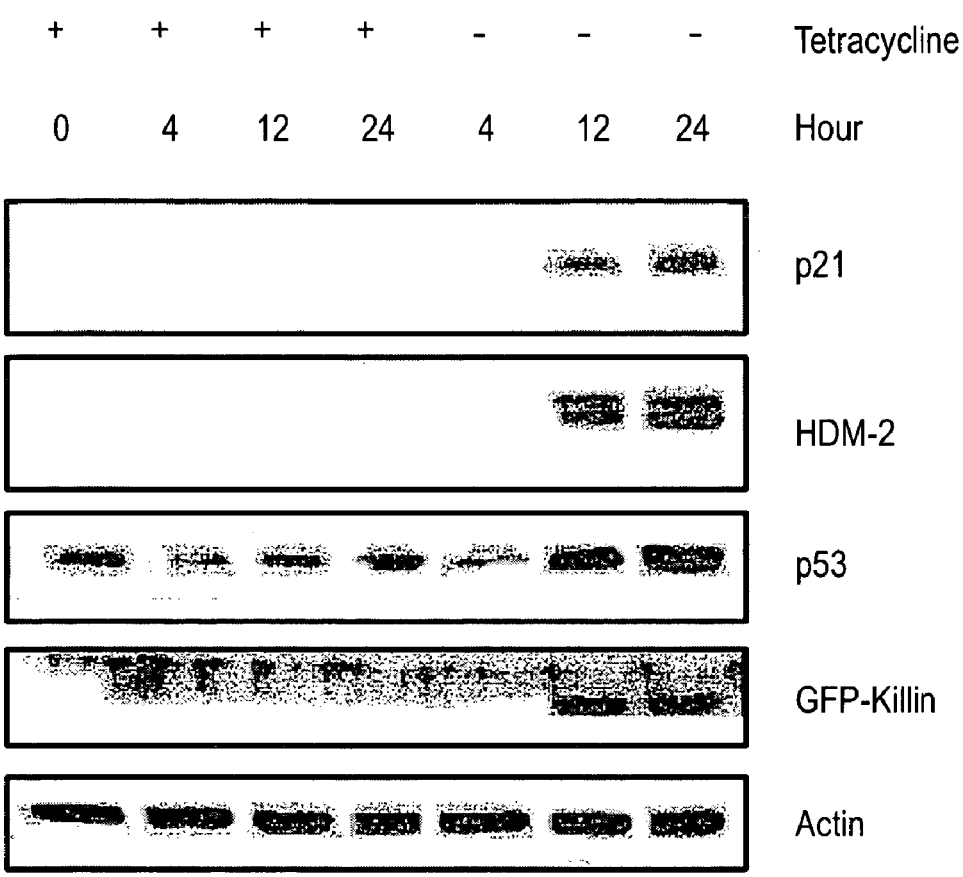
FIG. 9—Positive Feedback regulation of p53 by Killin. Western blot analysis of DLD-1 cells with an inducible GFP-Killin led to increase in p53 as well as its major target gene products, such as p21 and HDM-2 proteins. Cells were either non-induced (+tet) or induced (−tet) for the duration as indicated. Actin was used as a control for equal sample loading. GFP-Killin was detect with an antibody to GFP.

While Killin is not only necessary but sufficient in triggering rapid cell growth arrest, commencement of cell apoptosis induced by Killin (after 48 hours) appeared to be rather delayed, as compared to the effect of p53 induction (within 48 hours). The delayed onset of cell apoptosis seems to suggest that Killin-mediated growth arrest at S-phase may lead to subsequent activation of other downstream genes, which may cooperate in triggering a full apoptotic response. In contrast, such genes may be coordinately induced by p53 as immediate targets along with killin. This conjecture appeared to be supported by an intriguing piece of evidence of ours which showed that Killin expression alone was able to induce not only several major p53 target genes that the inventors have examined, such as hdm2 and p21, but also the endogenous p53 (FIG. 9). Thus, Killin may be part of a positive-feedback loop that is designed to amplify p53 functions to ensure precancerous cells are either completely arrested simultaneously at multiple checkpoints, or killed through apoptosis. The positive feedback activation of endogenous p53 by Killin conceivably could be mediated by ATR or its related kinases, which are known to be activated by genotoxic stresses such as stalled DNA replication forks (Abraham, 2001; Falck et al., 2005). The induction of p21 and possible other cell cycle regulators at G2/M by GFP-Killin may also explain the static cell cycle profiles within 48 hours following GFP-Killin induction. Future studies should help better define this important regulatory circuitry for p53.

Close inspection of the minimal 41 amino acid Killin peptide sequence essential for DNA binding in vitro and killing of bacteria in vivo, the inventors noted multiple WXXR and KXXW motifs (FIG. 6C). Although, theoretical protein folding prediction could not provide definitive secondary structure of the Killin/N8-50 peptide, conceivably these regular motifs would bring R, K and W residues along the same surface for DNA binding should the peptide fold into binary alpha helices that are connected by the single proline residue within the peptide sequence. The binary DNA binding fingers could allow Killin to bind to more than one DNA template, causing it to tangle up, which may explain why DNA-Killin/ N8-50 peptide complex had a dramatically retarded mobility on the gel. Conceivably, tryptophan (W) may interact with purine or pyrimidine bases, while basic amino acid residues arginine (R) and lysine (K) may interact with phosphates in the DNA. The extremely tight binding of Killin to DNA may prevent DNA synthesis machinery from access to the template, thus leading to inhibition of DNA synthesis and S-phase arrest. Future structural-functional studies by NMR and sited-directed mutagenesis should help verify or refine our prediction. The short Killin peptide (41-42 aa) and its potent activity in DNA binding, inhibition of DNA synthesis and ability to trigger apoptosis also make it a good candidate as a peptide drug for cancer treatment.

The extremely close proximity of killin and pten did not escape notice, since it would also make killin a candidate tumor-suppressor gene. pten was originally identified as a candidate tumor-suppressor by positional cloning from chromosome 10q23 region, which is frequently deleted in a variety of human tumors (Li et al., 1997; Steck et al., 1997). While pTEN is encoded by multiple exons spanning over 100 kb, killin resides in a single exon of only 4.1 kb. In fact, the extremely short 194 bp intergenic region connecting the two genes contains a divergent promoter that appears to be p53-responsive for both pten (Stambolic et al., 2001) and killin, with the latter shown here to be completely p53-dependent. Since one logical prediction for a major p53 target gene would be that such a gene could be a tumor-suppressor on its own, mutational analysis in cancer and genetic studies in animal models should help further define the precise role of Killin in tumor suppression.

II. KILLIN

According to the present invention, there has been identified a tumor suppressor encoded by a gene in the pten locus, and designated here as Killin. This molecule is capable of suppressing tumor phenotypes in various cancers. In addition to the entire Killin molecule, the present invention also relates to fragments of the polypeptide that may or may not retain the tumor suppressing (or other) activity. Fragments, including the N-terminus of the molecule may be generated by genetic engineering of translation stop sites within the coding region (discussed below). Alternatively, treatment of the Killin molecule with proteolytic enzymes, known as proteases, can produces a variety of N-terminal, C-terminal and internal fragments. Examples of fragments may include contiguous residues of the Killin sequence given in SEQ ID NO:1 of 6, 7, 8, 9, 10, 11, 12, 13, 14, 15, 16, 17, 18, 19, 20, 21, 22, 23, 24, 25, 30, 35, 40, 45, 50, 55, 60, 65, 75, 80, 85, 90, 95, 100, 125, 150, or 178 amino acids in length. These fragments may be purified according to known methods, such as precipitation (e.g., ammonium sulfate), HPLC, ion exchange chromatography, affinity chromatography (including immunoaffinity chromatography) or various size separations (sedimentation, gel electrophoresis, gel filtration).

A. Features of the Polypeptide

The gene for Killin encodes a 178 amino acid polypeptide (SEQ ID NO:1). When the present application refers to the function of Killin or "wild-type" activity, it is meant that the molecule in question has the ability to inhibit the transformation of a cell from a normally regulated state of proliferation to a malignant state, i.e., one associated with any sort of abnormal growth regulation, or to inhibit the transformation of a cell from an abnormal state to a highly malignant state, e.g., to prevent metastasis or invasive tumor growth. Other phenotypes that may be regulated by the normal Killin gene product are angiogenesis, adhesion, migration, cell-to-cell signaling, cell growth, cell proliferation, density-dependent growth, anchorage-dependent growth and others. Determination of which molecules possess this activity may be achieved using assays familiar to those of skill in the art. For example, transfer of genes encoding Killin, or variants thereof, into cells that do not have a functional Killin product, and hence exhibit impaired growth control, will identify, by virtue of growth suppression, those molecules having Killin function.

B. Variants of Killin

Amino acid sequence variants of the polypeptide can be substitutional, insertional or deletion variants. Deletion variants lack one or more residues of the native protein which are not essential for function or immunogenic activity, and are exemplified by the variants lacking a transmembrane sequence described above. Another common type of deletion variant is one lacking secretory signal sequences or signal sequences directing a protein to bind to a particular part of a cell. Insertional mutants typically involve the addition of material at a non-terminal point in the polypeptide. This may include the insertion of an immunoreactive epitope or simply a single residue. Terminal additions, called fusion proteins, are discussed below.

Substitutional variants typically contain the exchange of one amino acid for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The following is a discussion based upon changing of the amino acids of a protein to create an equivalent or improved molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and its underlying DNA coding sequence, and nevertheless obtain a protein with like properties. It is thus contemplated by the inventors that various changes may be made in the DNA sequences of genes without appreciable loss of their biological utility or activity, as discussed below. Table 1 shows the codons that encode particular amino acids.

TABLE 1

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

In making substitutional variants, the hydropathic index of amino acids may be considered. The importance of the hydropathic amino acid index in conferring interactive biologic function on a protein is generally understood in the art (Kyte & Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine *−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Another embodiment for the preparation of polypeptides according to the invention is the use of peptide mimetics. Mimetics are peptide-containing molecules that mimic elements of protein secondary structure. See, for example, Johnson et al., (1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outline above, to engineer second generation molecules having many of the natural properties of Killin, but with altered and even improved characteristics.

C. Domain Switching

Domain switching involves the generation of chimeric molecules using different but, in this case, related polypeptides. By comparing the Killin sequence with other tumor suppressors, one can make predictions as to the functionally significant regions of these molecules. It is possible, then, to switch related domains of these molecules in an effort to determine the criticality of these regions to Killin function. These molecules may have additional value in that these "chimeras" can be distinguished from natural molecules, while possibly providing the same function.

D. Fusion Proteins

A specialized kind of insertional variant is the fusion protein. This molecule generally has all or a substantial portion of the native molecule, linked at the N- or C-terminus, to all or a portion of a second polypeptide. For example, fusions typically employ leader sequences from other species to permit the recombinant expression of a protein in a heterologous host. Another useful fusion includes the addition of a immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions.

E. Purification of Proteins

It will be desirable to purify Killin or variants thereof. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fuctose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

F. Synthetic Peptides

The present invention also describes smaller Killin-related peptides for use in various embodiments of the present invention. Because of their relatively small size, the peptides of the invention can also be synthesized in solution or on a solid support in accordance with conventional techniques. Various automatic synthesizers are commercially available and can be used in accordance with known protocols. See, for example, Stewart and Young (1984); Tam et al. (1983); Merrifield (1986); and Barany and Merrifield (1979), each incorporated herein by reference. Short peptide sequences, or libraries of overlapping peptides, usually from about 6 up to about 35 to 50 amino acids, which correspond to the selected regions described herein, can be readily synthesized and then screened in screening assays designed to identify reactive peptides. Alternatively, recombinant DNA technology may be employed wherein a nucleotide sequence which encodes a peptide of the invention is inserted into an expression vector, transformed or transfected into an appropriate host cell and cultivated under conditions suitable for expression.

G. Antigen Compositions

The present invention also provides for the use of Killin proteins or peptides as antigens for the immunization of animals relating to the production of antibodies. It is envisioned that either Killin, or portions thereof, will be coupled, bonded, bound, conjugated or chemically-linked to one or more agents via linkers, polylinkers or derivatized amino acids. This may be performed such that a bispecific or multivalent composition or vaccine is produced. It is further envisioned that the methods used in the preparation of these compositions will be familiar to those of skill in the art and should be suitable for administration to animals, i.e., pharmaceutically acceptable. Preferred agents are the carriers are keyhole limpet hemocyannin (KLH) or bovine serum albumin (BSA).

III. NUCLEIC ACIDS

The present invention also provides, in another embodiment, genes encoding Killin. A gene for the human Killin molecule has been identified. The present invention is not limited in scope to this gene, however, as one of ordinary skill in the could readily identify related homologs in various other species (e.g., mouse, rat, rabbit, dog, monkey, gibbon, chimp, ape, baboon, cow, pig, horse, sheep, cat and other species).

In addition, it should be clear that the present invention is not limited to the specific nucleic acids disclosed herein. As discussed below, a "Killin gene" may contain a variety of different bases and yet still produce a corresponding polypeptide that is functionally indistinguishable from, and in some cases structurally identical to, the human gene disclosed herein.

Similarly, any reference to a nucleic acid should be read as encompassing a host cell containing that nucleic acid and, in some cases, capable of expressing the product of that nucleic acid. In addition to therapeutic considerations, cells expressing nucleic acids of the present invention may prove useful in the context of screening for agents that induce, repress, inhibit, augment, interfere with, block, abrogate, stimulate or enhance the function of Killin.

A. Nucleic Acids Encoding Killin

Nucleic acids according to the present invention may encode an entire Killin gene, a domain of Killin that expresses a tumor suppressing function, or any other fragment of the Killin sequences set forth herein. The nucleic acid may be derived from genomic DNA, i.e., cloned directly from the genome of a particular organism. In preferred embodiments, however, the nucleic acid would comprise complementary DNA (cDNA). Also contemplated is a cDNA plus a natural intron or an intron derived from another gene; such engineered molecules are sometime referred to as "mini-genes." At a minimum, these and other nucleic acids of the present invention may be used as molecular weight standards in, for example, gel electrophoresis.

The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression or where non-coding regions such as introns are to be targeted in an antisense strategy.

It also is contemplated that a given Killin from a given species may be represented by natural variants that have slightly different nucleic acid sequences but, nonetheless, encode the same protein (see Table 1, above).

As used in this application, the term "a nucleic acid encoding a Killin" refers to a nucleic acid molecule that has been isolated free of total cellular nucleic acid. In certain embodiments, the invention concerns a nucleic acid sequence essentially as set forth in SEQ ID NO:2. The term "as set forth in SEQ ID NO:2" means that the nucleic acid sequence substantially corresponds to a portion of SEQ ID NO:2. The term "functionally equivalent codon" is used herein to refer to codons that encode the same amino acid, such as the six codons for arginine or serine, and also refers to codons that encode biologically equivalent amino acids, as discussed in the following pages.

Allowing for the degeneracy of the genetic code, sequences that have at least about 50%, usually at least about 60%, more usually about 70%, most usually about 80%, preferably at least about 90% and most preferably about 95% of nucleotides that are identical to the nucleotides of SEQ ID NO:2. Sequences that are essentially the same as those set forth in SEQ ID NO:2 also may be functionally defined as sequences that are capable of hybridizing to a nucleic acid segment containing the complement of SEQ ID NO:2 under standard conditions.

The DNA segments of the present invention include those encoding biologically functional equivalent Killin proteins and peptides, as described above. Such sequences may arise as a consequence of codon redundancy and amino acid functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques or may be introduced randomly and screened later for the desired function, as described below.

B. Oligonucleotide Probes and Primers

Naturally, the present invention also encompasses DNA segments that are complementary, or essentially complementary, to the sequence set forth in SEQ ID NO:2. Nucleic acid sequences that are "complementary" are those that are capable of base-pairing according to the standard Watson-Crick complementary rules. As used herein, the term "complementary sequences" means nucleic acid sequences that are substantially complementary, as may be assessed by the same nucleotide comparison set forth above, or as defined as being capable of hybridizing to the nucleic acid segment of SEQ ID NO:2 under relatively stringent conditions such as those described herein. Such sequences may encode the entire Killin protein or functional or non-functional fragments thereof.

Alternatively, the hybridizing segments may be shorter oligonucleotides. Sequences of 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that exemplary oligonucleotides of 8, 9, 10, 11, 12, 13, 14, 15, 16, 17, 18, 19, 20, 25, 30, 35, 40, 45, 50, 55, 60, 65, 70, 75, 80, 85, 90, 95, 100 or more base pairs will be used, although others are contemplated. Longer polynucleotides encoding 250, 500, 1000, 1212, 1500, 2000, 2500, 3000 or longer are contemplated as well. Such oligonucleotides will find use, for example, as probes in Southern and Northern blots and as primers in amplification reactions.

Suitable hybridization conditions will be well known to those of skill in the art. In certain applications, for example, substitution of amino acids by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated, and thus will generally be a method of choice depending on the desired results.

In other embodiments, hybridization may be achieved under conditions of, for example, 50 mM Tris-HCl (pH 8.3), 75 mM KCl, 3 mM $MgCl_2$, 10 mM dithiothreitol, at temperatures between approximately 20° C. to about 37° C. Other hybridization conditions utilized could include approximately 10 mM Tris-HCl (pH 8.3), 50 mM KCl, 1.5 µM $MgCl_2$, at temperatures ranging from approximately 40° C. to about 72° C. Formamide and SDS also may be used to alter the hybridization conditions.

One method of using probes and primers of the present invention is in the search for genes related to Killin or, more particularly, homologs of Killin from other species. Normally, the target DNA will be a genomic or cDNA library, although screening may involve analysis of RNA molecules. By varying the stringency of hybridization, and the region of the probe, different degrees of homology may be discovered.

Another way of exploiting probes and primers of the present invention is in site-directed, or site-specific mutagenesis. Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

The technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double-stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double-stranded vector which includes within its sequence a DNA sequence encoding the desired protein. An oligonucleotide primer bearing the desired mutated sequence is synthetically prepared. This primer is then annealed with the single-stranded DNA preparation, taking into account the degree of mismatch when selecting hybridization conditions, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected that include recombinant vectors bearing the mutated sequence arrangement.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

C. Antisense Constructs

In some cases, mutant tumor suppressors may not be non-functional. Rather, they may have aberrant functions that cannot be overcome by replacement gene therapy, even where the "wild-type" molecule is expressed in amounts in excess of the mutant polypeptide. Antisense treatments are one way of addressing this situation. Antisense technology also may be used to "knock-out" function of Killin in the development of cell lines or transgenic mice for research, diagnostic and screening purposes.

Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarity to regions within 50-200 bases of an ifitron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme; see below) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

D. Ribozymes

Another approach for addressing the "dominant negative" mutant tumor suppressor is through the use of ribozymes. Although proteins traditionally have been used for catalysis of nucleic acids, another class of macromolecules has emerged as useful in this endeavor. Ribozymes are RNA-protein complexes that cleave nucleic acids in a site-specific fashion. Ribozymes have specific catalytic domains that possess endonuclease activity (Kim and Cech, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cook et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cook et al., 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990). Recently, it was reported that ribozymes elicited genetic changes in some cells lines to which they were applied; the altered genes included the oncogenes H-ras, c-fos and genes of HIV. Most of this work involved the modification of a target mRNA, based on a specific mutant codon that is cleaved by a specific ribozyme.

E. Vectors for Cloning, Gene Transfer and Expression

Within certain embodiments, expression vectors are employed to express the Killin polypeptide product, which can then be purified for various uses. In other embodiments, the expression vectors are used in gene therapy. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding a gene of interest.

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al. (1989) and Ausubel et al. (1994), both incorporated herein by reference.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

(i) Regulatory Elements

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally-associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally-occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202, 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. One example is the native Killin promoter, set forth in SEQ ID NO: 3. Those of skill in the art of molecular biology generally know the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Table 2 lists several elements/promoters that may be employed, in the context of the present invention, to regulate the expression of a gene. This list is not intended to be exhaustive of all the possible elements involved in the promotion of expression but, merely, to be exemplary thereof. Table 3 provides examples of inducible elements, which are regions of a nucleic acid sequence that can be activated in response to a specific stimulus.

TABLE 2

| Promoter/Enhancer | Promoter and/or Enhancer References |
|---|---|
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |

TABLE 2-continued

Promoter and/or Enhancer

| Promoter/Enhancer | References |
| --- | --- |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Omitz et al., 1987 |
| Metallothionein (MTII) | Karin et al., 1987; Culotta et al., 1989 |
| Collagenase | Pinkert et al., 1987; Angel et al., 1987 |
| Albumin | Pinkert et al., 1987; Tronche et al., 1989, 1990 |
| α-Fetoprotein | Godbout et al., 1988; Campere et al., 1989 |
| t-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| $α_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Chol et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al, 1987; Hirochika et al., 1987; Stephens et al., 1987; Glue et al., 1988 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1998; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 3

Inducible Elements

| Element | Inducer | References |
| --- | --- | --- |
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |

TABLE 3-continued

Inducible Elements

| Element | Inducer | References |
|---|---|---|
| MMTV (mouse mammary tumor virus) | Glucocorticoids | Huang et al., 1981; Lee et al., 1981; Majors et al., 1983; Chandler et al., 1983; Lee et al., 1984; Ponta et al., 1985; Sakai et al., 1988 |
| β-Interferon | poly(rI) x poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

The identity of tissue-specific promoters or elements, as well as assays to characterize their activity, is well known to those of skill in the art. Examples of such regions include the human LIMK2 gene (Nomoto et al. 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki, et al., 1998), D1A dopamine receptor gene (Lee, et al., 1997), insulin-like growth factor II (Wu et al., 1997), human platelet endothelial cell adhesion molecule-1 (Almendro et al., 1996). Tumor specific promoters also will find use in the present invention. Some such promoters are set forth in Tables 4 and 5.

TABLE 4

Candidate Tissue-Specific Promoters for Cancer Gene Therapy

| Tissue-specific promoter | Cancers in which promoter is active | Normal cells in which promoter is active |
|---|---|---|
| Carcinoembryonic antigen (CEA)* | Most colorectal carcinomas; 50% of lung carcinomas; 40-50% of gastric carcinomas; most pancreatic carcinomas; many breast carcinomas | Colonic mucosa; gastric mucosa; lung epithelia; eccrine sweat glands; cells in testes |
| Prostate-specific antigen (PSA) | Most prostate carcinomas | Prostate epithelium |
| Vasoactive intestinal peptide (VIP) | Majority of non-small cell lung cancers | Neurons; lymphocytes; mast cells; eosinophils |
| Surfactant protein A (SP-A) | Many lung adenocarcinomas cells | Type II pneumocytes; Clara |
| Human achaete-scute homolog (hASH) | Most small cell lung cancers | Neuroendocrine cells in lung |
| Mucin-1 (MUC1)** | Most adenocarcinomas (originating from any tissue) | Glandular epithelial cells in breast and in respiratory, gastrointestinal, and genitourinary tracts |
| Alpha-fetoprotein | Most hepatocellular carcinomas; possibly many testicular cancers | Hepatocytes (under certain conditions); testis |
| Albumin | Most hepatocellular carcinomas | Hepatocytes |
| Tyrosinase | Most melanomas | Melanocytes; astrocytes; Schwann cells; some neurons |
| Tyrosine-binding protein (TRP) | Most melanomas | Melanocytes; astrocytes, Schwann cells; some neurons |
| Keratin 14 | Presumably many squamous cell carcinomas (e.g., Head and neck cancers) | Keratinocytes |
| EBV LD-2 | Many squamous cell carcinomas of head and neck | Keratinocytes of upper digestive Keratinocytes of upper digestive tract |

TABLE 4-continued

Candidate Tissue-Specific Promoters for Cancer Gene Therapy

| Tissue-specific promoter | Cancers in which promoter is active | Normal cells in which promoter is active |
|---|---|---|
| Glial fibrillary acidic protein (GFAP) | Many astrocytomas | Astrocytes |
| Myelin basic protein (MBP) | Many gliomas | Oligodendrocytes |
| Testis-specific angiotensin-converting enzyme (Testis-specific ACE) | Possibly many testicular cancers | Spermatazoa |
| Osteocalcin | Possibly many osteosarcomas | Osteoblasts |

TABLE 5

Candidate Promoters for Tissue-Specific Targeting of Tumors

| Promoter | Cancers in which Promoter is active | Normal cells in which Promoter is active |
|---|---|---|
| E2F-regulated promoter | Almost all cancers | Proliferating cells |
| HLA-G | Many colorectal carcinomas; many melanomas; possibly many other cancers | Lymphocytes; monocytes; spermatocytes; trophoblast |
| FasL | Most melanomas; many pancreatic carcinomas; most astrocytomas possibly many other cancers | Activated leukocytes: neurons; endothelial cells; keratinocytes; cells in immunoprivileged tissues; some cells in lungs, ovaries, liver, and prostate |
| Myc-regulated promoter | Most lung carcinomas (both small cell and non-small cell); most colorectal carcinomas | Proliferating cells (only some cell-types): mammary epithelial cells (including non-proliferating) |
| MAGE-1 | Many melanomas; some non-small cell lung carcinomas; some breast carcinomas | Testis |
| VEGF | 70% of all cancers (constitutive overexpression in many cancers) | Cells at sites of neovascularization (but unlike in tumors, expression is transient, less strong, and never constitutive) |
| bFGF | Presumably many different cancers, since bFGF expression is induced by ischemic conditions | Cells at sites of ischemia (but unlike tumors, expression is transient, less strong, and never constitutive) |
| COX-2 | Most colorectal carcinomas; many lung carcinomas; possibly many other cancers | Cells at sites of inflammation |
| IL-10 | Most colorectal carcinomas; many lung carcinomas; many squamous cell carcinomas of head and neck; possibly many other cancers | Leukocytes |
| GRP78/BiP | Presumably many different cancers, since GRP7S expression is induced by tumor-specific conditions | Cells at sites of ishemia |
| CarG elements from Egr-1 | Induced by ionization radiation, so conceivably most tumors upon irradiation | Cells exposed to ionizing radiation; leukocytes |

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

(ii) IRES

In certain embodiments of the invention, the use of internal ribosome entry sites (IRES) elements are used to create multigene, or polycistronic, messages. IRES elements are able to bypass the ribosome scanning model of 5'-methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

(iii) Multi-Purpose Cloning Sites

Vectors can include a multiple cloning site (MCS), which is a nucleic acid region that contains multiple restriction enzyme sites, any of which can be used in conjunction with standard recombinant technology to digest the vector. See Carbonelli et al., 1999, Levenson et al., 1998, and Cocea, 1997, incorporated herein by reference. "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

(iv) Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see Chandler et al., 1997, herein incorporated by reference.)

(v) Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and/or to minimize read through from the cassette into other sequences.

Terminators contemplated for use in the invention include any known terminator of transcription described herein or known to one of ordinary skill in the art, including but not limited to, for example the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

(vi) Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Polyadenylation may increase the stability of the transcript or may facilitate cytoplasmic transport.

(vii) Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

(viii) Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is calorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

(ix) Viral Vectors

The capacity of certain viral vectors to efficiently infect or enter cells, to integrate into a host cell genome and stably express viral genes, have led to the development and application of a number of different viral vector systems (Robbins et al., 1998). Viral systems are currently being developed for use as vectors for ex vivo and in vivo gene transfer. For example, adenovirus, herpes-simplex virus, retrovirus and adeno-associated virus vectors are being evaluated currently for treatment of diseases such as cancer, cystic fibrosis, Gaucher disease, renal disease and arthritis (Robbins and Ghivizzani, 1998; Imai et al., 1998; U.S. Pat. No. 5,670,488). The various viral vectors described below, present specific advantages and disadvantages, depending on the particular gene-therapeutic application.

Adenoviral Vectors. In particular embodiments, an adenoviral expression vector is contemplated for the delivery of expression constructs. "Adenovirus expression vector" is meant to include those constructs containing adenovirus sequences sufficient to (a) support packaging of the construct and (b) to ultimately express a tissue or cell-specific construct that has been cloned therein.

Adenoviruses comprise linear, double-stranded DNA, with a genome ranging from 30 to 35 kb in size (Reddy et al., 1998; Morrison et al., 1997; Chillon et al., 1999). An adenovirus expression vector according to the present invention comprises a genetically engineered form of the adenovirus. Advantages of adenoviral gene transfer include the ability to infect a wide variety of cell types, including non-dividing cells, a mid-sized genome, ease of manipulation, high infectivity and the ability to be grown to high titers (Wilson, 1996). Further, adenoviral infection of host cells does not result in chromosomal integration because adenoviral DNA can replicate in an episomal manner, without potential genotoxicity associated with other viral vectors. Adenoviruses also are structurally stable (Marienfeld et al., 1999) and no genome rearrangement has been detected after extensive amplification (Parks et al., 1997; Bett et al., 1993).

Salient features of the adenovirus genome are an early region (E1, E2, E3 and E4 genes), an intermediate region (pIX gene, Iva2 gene), a late region (L1, L2, L3, L4 and L5 genes), a major late promoter (MLP), inverted-terminal-repeats (ITRs) and a $\psi$ sequence (Zheng, et al., 1999; Robbins et al., 1998; Graham and Prevec, 1995). The early genes E1, E2, E3 and E4 are expressed from the virus after infection and encode polypeptides that regulate viral gene expression, cellular gene expression, viral replication, and inhibition of cellular apoptosis. Further on during viral infection, the MLP is activated, resulting in the expression of the late (L) genes, encoding polypeptides required for adenovirus encapsidation. The intermediate region encodes components of the adenoviral capsid. Adenoviral inverted terminal repeats (ITRs; 100-200 bp in length), are cis elements, and function as origins of replication and are necessary for viral DNA replication. The $\psi$ sequence is required for the packaging of the adenoviral genome.

A common approach for generating an adenoviruses for use as a gene transfer vector is the deletion of the E1 gene (E1$^-$), which is involved in the induction of the E2, E3 and E4 promoters (Graham and Prevec, 1995). Subsequently, a therapeutic gene or genes can be inserted recombinantly in place of the E1 gene, wherein expression of the therapeutic gene(s) is driven by the E1 promoter or a heterologous promoter. The E1$^-$, replication-deficient virus is then proliferated in a "helper" cell line that provides the E1 polypeptides in trans (e.g., the human embryonic kidney cell line 293). Thus, in the present invention it may be convenient to introduce the transforming construct at the position from which the E1-coding sequences have been removed. However, the position of insertion of the construct within the adenovirus sequences is not critical to the invention. Alternatively, the E3 region, portions of the E4 region or both may be deleted, wherein a heterologous nucleic acid sequence under the control of a promoter operable in eukaryotic cells is inserted into the adenovirus genome for use in gene transfer (U.S. Pat. Nos. 5,670,488; 5,932,210, each specifically incorporated herein by reference).

Although adenovirus based vectors offer several unique advantages over other vector systems, they often are limited by vector immunogenicity, size constraints for insertion of recombinant genes and low levels of replication. The preparation of a recombinant adenovirus vector deleted of all open reading frames, comprising a full length dystrophin gene and the terminal repeats required for replication (Haecker et al., 1997) offers some potentially promising advantages to the above mentioned adenoviral shortcomings. The vector was grown to high titer with a helper virus in 293 cells and was capable of efficiently transducing dystrophin in mdx mice, in myotubes in vitro and muscle fibers in vivo. Helper-dependent viral vectors are discussed below.

A major concern in using adenoviral vectors is the generation of a replication-competent virus during vector production in a packaging cell line or during gene therapy treatment of an individual. The generation of a replication-competent virus could pose serious threat of an unintended viral infection and pathological consequences for the patient. Armentano et al. (1990), describe the preparation of a replication-defective adenovirus vector, claimed to eliminate the potential for the inadvertent generation of a replication-competent adenovirus (U.S. Pat. No. 5,824,544, specifically incorporated herein by reference). The replication-defective adenovirus method comprises a deleted E1 region and a relocated protein IX gene, wherein the vector expresses a heterologous, mammalian gene.

Other than the requirement that the adenovirus vector be replication defective, or at least conditionally defective, the nature of the adenovirus vector is not believed to be crucial to the successful practice of the invention. The adenovirus may be of any of the 42 different known serotypes and/or subgroups A-F. Adenovirus type 5 of subgroup C is the preferred starting material in order to obtain the conditional replication-defective adenovirus vector for use in the present invention. This is because adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Adenovirus growth and manipulation is known to those of skill in the art, and exhibits broad host range in vitro and in vivo (U.S. Pat. Nos. 5,670,488; 5,932, 210; 5,824,544). This group of viruses can be obtained in high titers, e.g., $10^9$ to $10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. Many experiments, innovations, preclinical studies and clinical trials are currently under investigation for the use of adenoviruses as gene delivery vectors. For example, adenoviral gene delivery-based gene therapies are being developed for liver diseases (Han et al., 1999), psychiatric diseases (Lesch, 1999), neurological diseases (Smith, 1998; Hermens and Verhaagen, 1998), coronary diseases (Feldman et al., 1996), muscular diseases (Petrof, 1998), gastrointestinal diseases (Wu, 1998) and various cancers such as colorectal (Fujiwara and Tanaka, 1998; Dorai et al., 1999), pancreatic, bladder (Irie et al., 1999), head and neck (Blackwell et al., 1999), breast (Stewart et al., 1999), lung (Batra et al., 1999) and ovarian (Vanderkwaak et al., 1999).

Retroviral Vectors. In certain embodiments of the invention, the use of retroviruses for gene delivery are contemplated. Retroviruses are RNA viruses comprising an RNA genome. When a host cell is infected by a retrovirus, the genomic RNA is reverse transcribed into a DNA intermediate which is integrated into the chromosomal DNA of infected cells. This integrated DNA intermediate is referred to as a provirus. A particular advantage of retroviruses is that they can stably infect dividing cells with a gene of interest (e.g., a therapeutic gene) by integrating into the host DNA, without expressing immunogenic viral proteins. Theoretically, the integrated retroviral vector will be maintained for the life of the infected host cell, expressing the gene of interest.

The retroviral genome and the proviral DNA have three genes: gag, pol, and env, which are flanked by two long terminal repeat (LTR) sequences. The gag gene encodes the internal structural (matrix, capsid, and nucleocapsid) proteins; the pol gene encodes the RNA-directed DNA polymerase (reverse transcriptase) and the env gene encodes viral envelope glycoproteins. The 5' and 3' LTRs serve to promote transcription and polyadenylation of the virion RNAs. The LTR contains all other cis-acting sequences necessary for viral replication.

A recombinant retrovirus of the present invention may be genetically modified in such a way that some of the structural, infectious genes of the native virus have been removed and replaced instead with a nucleic acid sequence to be delivered to a target cell (U.S. Pat. Nos. 5,858,744; 5,739,018, each incorporated herein by reference). After infection of a cell by the virus, the virus injects its nucleic acid into the cell and the retrovirus genetic material can integrate into the host cell genome. The transferred retrovirus genetic material is then transcribed and translated into proteins within the host cell. As with other viral vector systems, the generation of a replication-competent retrovirus during vector production or during therapy is a major concern. Retroviral vectors suitable for use in the present invention are generally defective retroviral vectors that are capable of infecting the target cell, reverse transcribing their RNA genomes, and integrating the reverse transcribed DNA into the target cell genome, but are incapable of replicating within the target cell to produce infectious retroviral particles (e.g., the retroviral genome transferred into the target cell is defective in gag, the gene encoding virion structural proteins, and/or in pol, the gene encoding reverse transcriptase). Thus, transcription of the provirus and assembly into infectious virus occurs in the presence of an appropriate helper virus or in a cell line containing appropriate sequences enabling encapsidation without coincident production of a contaminating helper virus.

The growth and maintenance of retroviruses is known in the art (U.S. Pat. Nos. 5,955,331; 5,888,502, each specifically incorporated herein by reference). Nolan et al. describe the production of stable high titre, helper-free retrovirus comprising a heterologous gene (U.S. Pat. No. 5,830,725, specifically incorporated herein by reference). Methods for constructing packaging cell lines useful for the generation of helper-free recombinant retroviruses with amphoteric or ecotrophic host ranges, as well as methods of using the recombinant retroviruses to introduce a gene of interest into eukaryotic cells in vivo and in vitro are contemplated in the present invention (U.S. Pat. No. 5,955,331).

Currently, the majority of all clinical trials for vector-mediated gene delivery use murine leukemia virus (MLV)-based retroviral vector gene delivery (Robbins et al., 1998; Miller et al., 1993). Disadvantages of retroviral gene delivery includes a requirement for ongoing cell division for stable infection and a coding capacity that prevents the delivery of large genes. However, recent development of vectors such as lentivirus (e.g., HIV), simian immunodeficiency virus (SW) and equine infectious-anemia virus (EIAV), which can infect certain non-dividing cells, potentially allow the in vivo use of retroviral vectors for gene therapy applications (Amado and Chen, 1999; Klimatcheva et al., 1999; White et al., 1999; Case et al., 1999). For example, HIV-based vectors have been used to infect non-dividing cells such as neurons (Miyatake et al., 1999), islets (Leibowitz et al., 1999) and muscle cells (Johnston et al., 1999). The therapeutic delivery of genes via retroviruses are currently being assessed for the treatment of various disorders such as inflammatory disease (Moldawer et al., 1999), AIDS (Amado et al., 1999; Engel and Kohn, 1999), cancer (Clay et al., 1999), cerebrovascular disease (Weihl et al., 1999) and hemophilia (Kay, 1998).

Herpesviral Vectors. Herpes simplex virus (HSV) type I and type II contain a double-stranded, linear DNA genome of approximately 150 kb, encoding 70-80 genes. Wild type HSV are able to infect cells lytically and to establish latency in certain cell types (e.g., neurons). Similar to adenovirus, HSV also can infect a variety of cell types including muscle (Yeung et al., 1999), ear (Derby et al., 1999), eye (Kaufman et al., 1999), tumors (Yoon et al., 1999; Howard et al., 1999), lung (Kohut et al., 1998), neuronal (Garrido et al., 1999; Lachmann and Efstathiou, 1999), liver (Miytake et al., 1999; Kooby et al., 1999) and pancreatic islets (Rabinovitch et al., 1999).

HSV viral genes are transcribed by cellular RNA polymerase II and are temporally regulated, resulting in the transcription and subsequent synthesis of gene products in roughly three discernable phases or kinetic classes. These phases of genes are referred to as the Immediate Early (IE) or alpha genes, Early (E) or beta genes and Late (L) or gamma genes. Immediately following the arrival of the genome of a virus in the nucleus of a newly infected cell, the IE genes are transcribed. The efficient expression of these genes does not require prior viral protein synthesis. The products of IE genes are required to activate transcription and regulate the remainder of the viral genome.

For use in therapeutic gene delivery, HSV must be rendered replication-defective. Protocols for generating replication-defective HSV helper virus-free cell lines have been described (U.S. Pat. Nos. 5,879,934; 5,851,826, each specifically incorporated herein by reference in its entirety). One IE protein, Infected Cell Polypeptide 4 (ICP4), also known as alpha 4 or Vmw175, is absolutely required for both virus infectivity and the transition from IE to later transcription. Thus, due to its complex, multifunctional nature and central role in the regulation of HSV gene expression, ICP4 has typically been the target of HSV genetic studies.

Phenotypic studies of HSV viruses deleted of ICP4 indicate that such viruses will be potentially useful for gene transfer purposes (Krisky et al., 1998a). One property of viruses deleted for ICP4 that makes them desirable for gene transfer is that they only express the five other IE genes: ICP0, ICP6, ICP27, ICP22 and ICP47 (DeLuca et al., 1985), without the expression of viral genes encoding proteins that direct viral DNA synthesis, as well as the structural proteins of the virus. This property is desirable for minimizing possible deleterious effects on host cell metabolism or an immune response following gene transfer. Further deletion of IE genes ICP22 and ICP27, in addition to ICP4, substantially improve reduction of HSV cytotoxicity and prevented early and late viral gene expression (Krisky et al., 1998b).

The therapeutic potential of HSV in gene transfer has been demonstrated in various in vitro model systems and in vivo for diseases such as Parkinson's (Yamada et al., 1999), retinoblastoma (Hayashi et al., 1999), intracerebral and intradermal tumors (Moriuchi et al., 1998), B-cell malignancies (Suzuki et al., 1998), ovarian cancer (Wang et al., 1998) and Duchenne muscular dystrophy (Huard et al., 1997).

Adeno-Associated Viral Vectors. Adeno-associated virus (AAV), a member of the parvovirus family, is a human virus that is increasingly being used for gene delivery therapeutics. AAV has several advantageous features not found in other viral systems. First, AAV can infect a wide range of host cells, including non-dividing cells. Second, AAV can infect cells from different species. Third, AAV has not been associated with any human or animal disease and does not appear to alter the biological properties of the host cell upon integration. For example, it is estimated that 80-85% of the human population has been exposed to AAV. Finally, AAV is stable at a wide range of physical and chemical conditions which lends itself to production, storage and transportation requirements.

The AAV genome is a linear, single-stranded DNA molecule containing 4681 nucleotides. The AAV genome generally comprises an internal non-repeating genome flanked on each end by inverted terminal repeats (ITRs) of approximately 145 bp in length. The ITRs have multiple functions, including origins of DNA replication, and as packaging signals for the viral genome. The internal non-repeated portion of the genome includes two large open reading frames, known as the AAV replication (rep) and capsid (cap) genes. The rep and cap genes code for viral proteins that allow the virus to replicate and package the viral genome into a virion. A family of at least four viral proteins are expressed from the AAV rep region, Rep 78, Rep 68, Rep 52, and Rep 40, named according to their apparent molecular weight. The AAV cap region encodes at least three proteins, VP1, VP2, and VP3.

AAV is a helper-dependent virus requiring co-infection with a helper virus (e.g., adenovirus, herpesvirus or vaccinia) in order to form AAV virions. In the absence of co-infection with a helper virus, AAV establishes a latent state in which the viral genome inserts into a host cell chromosome, but infectious virions are not produced. Subsequent infection by a helper virus "rescues" the integrated genome, allowing it to replicate and package its genome into infectious AAV virions. Although AAV can infect cells from different species, the helper virus must be of the same species as the host cell (e.g., human AAV will replicate in canine cells co-infected with a canine adenovirus).

AAV has been engineered to deliver genes of interest by deleting the internal non-repeating portion of the AAV genome and inserting a heterologous gene between the ITRs. The heterologous gene may be functionally linked to a heterologous promoter (constitutive, cell-specific, or inducible) capable of driving gene expression in target cells. To produce infectious recombinant AAV (rAAV) containing a heterologous gene, a suitable producer cell line is transfected with a rAAV vector containing a heterologous gene. The producer cell is concurrently transfected with a second plasmid harboring the AAV rep and cap genes under the control of their respective endogenous promoters or heterologous promoters. Finally, the producer cell is infected with a helper virus.

Once these factors come together, the heterologous gene is replicated and packaged as though it were a wild-type AAV genome. When target cells are infected with the resulting rAAV virions, the heterologous gene enters and is expressed in the target cells. Because the target cells lack the rep and cap genes and the adenovirus helper genes, the rAAV cannot further replicate, package or form wild-type AAV.

The use of helper virus, however, presents a number of problems. First, the use of adenovirus in a rAAV production system causes the host cells to produce both rAAV and infectious adenovirus. The contaminating infectious adenovirus can be inactivated by heat treatment (56° C. for 1 hour). Heat treatment, however, results in approximately a 50% drop in the titer of functional rAAV virions. Second, varying amounts of adenovirus proteins are present in these preparations. For example, approximately 50% or greater of the total protein obtained in such rAAV virion preparations is free adenovirus fiber protein. If not completely removed, these adenovirus proteins have the potential of eliciting an immune response from the patient. Third, AAV vector production methods which employ a helper virus require the use and manipulation of large amounts of high titer infectious helper virus, which presents a number of health and safety concerns, particularly in regard to the use of a herpesvirus. Fourth, concomitant production of helper virus particles in rAAV virion producing cells diverts large amounts of host cellular resources away from rAAV virion production, potentially resulting in lower rAAV virion yields.

Lentiviral Vectors. Lentiviruses are complex retroviruses, which, in addition to the common retroviral genes gag, pol, and env, contain other genes with regulatory or structural function. The higher complexity enables the virus to modulate its life cycle, as in the course of latent infection. Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. The lentiviral genome and the proviral DNA have the three genes found in retroviruses: gag, pol and env, which are flanked by two long terminal repeat (LTR) sequences. The gag gene encodes the internal structural (matrix, capsid and nucleocapsid) proteins; the pol gene encodes the RNA-directed DNA polymerase (reverse transcriptase), a protease and an integrase; and the env gene encodes viral envelope glycoproteins. The 5' and 3' LTR's serve to promote transcription and polyadenylation of the virion RNA's. The LTR contains all other cis-acting sequences necessary for viral replication. Lentiviruses have additional genes including vif, vpr, tat, rev, vpu, nef and vpx.

Adjacent to the 5' LTR are sequences necessary for reverse transcription of the genome (the tRNA primer binding site) and for efficient encapsidation of viral RNA into particles (the Psi site). If the sequences necessary for encapsidation (or packaging of retroviral RNA into infectious virions) are missing from the viral genome, the cis defect prevents encapsidation of genomic RNA. However, the resulting mutant remains capable of directing the synthesis of all virion proteins.

Lentiviral vectors are known in the art, see Naldini et al., (1996); Zufferey et al., (1997); U.S. Pat. Nos. 6,013,516; and 5,994,136. In general, the vectors are plasmid-based or virus-based, and are configured to carry the essential sequences for incorporating foreign nucleic acid, for selection and for transfer of the nucleic acid into a host cell. The gag, pol and env genes of the vectors of interest also are known in the art. Thus, the relevant genes are cloned into the selected vector and then used to transform the target cell of interest.

Recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. This describes a first vector that can provide a nucleic acid encoding a viral gag and a pol gene and another vector that can provide a nucleic acid encoding a viral env to produce a packaging cell. Introducing a vector providing a heterologous gene, such as the STAT-1α gene in this invention, into that packaging cell yields a producer cell which releases infectious viral particles carrying the foreign gene of interest. The env preferably is an amphotropic envelope protein which allows transduction of cells of human and other species.

One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

The vector providing the viral env nucleic acid sequence is associated operably with regulatory sequences, e.g., a promoter or enhancer. The regulatory sequence can be any eukaryotic promoter or enhancer, including for example, the Moloney murine leukemia virus promoter-enhancer element, the human cytomegalovirus enhancer or the vaccinia P7.5 promoter. In some cases, such as the Moloney murine leukemia virus promoter-enhancer element, the promoter-enhancer elements are located within or adjacent to the LTR sequences.

The heterologous or foreign nucleic acid sequence, such as the STAT-1α encoding polynucleotide sequence herein, is linked operably to a regulatory nucleic acid sequence. Preferably, the heterologous sequence is linked to a promoter, resulting in a chimeric gene. The heterologous nucleic acid sequence may also be under control of either the viral LTR promoter-enhancer signals or of an internal promoter, and retained signals within the retroviral LTR can still bring about efficient expression of the transgene. Marker genes may be utilized to assay for the presence of the vector, and thus, to confirm infection and integration. The presence of a marker gene ensures the selection and growth of only those host cells which express the inserts. Typical selection genes encode proteins that confer resistance to antibiotics and other toxic substances, e.g., histidinol, puromycin, hygromycin, neomycin, methotrexate, etc., and cell surface markers.

The vectors are introduced via transfection or infection into the packaging cell line. The packaging cell line produces viral particles that contain the vector genome. Methods for transfection or infection are well known by those of skill in the art. After cotransfection of the packaging vectors and the transfer vector to the packaging cell line, the recombinant virus is recovered from the culture media and titered by standard methods used by those of skill in the art. Thus, the packaging constructs can be introduced into human cell lines by calcium phosphate transfection, lipofection or electroporation, generally together with a dominant selectable marker, such as neo, DHFR, Gln synthetase or ADA, followed by selection in the presence of the appropriate drug and isolation of clones. The selectable marker gene can be linked physically to the packaging genes in the construct.

Lentiviral transfer vectors Naldini et al. (1996), have been used to infect human cells growth-arrested in vitro and to transduce neurons after direct injection into the brain of adult rats. The vector was efficient at transferring marker genes in vivo into the neurons and long term expression in the absence of detectable pathology was achieved. Animals analyzed ten months after a single injection of the vector showed no decrease in the average level of transgene expression and no sign of tissue pathology or immune reaction (Blomer et al., 1997). Thus, in the present invention, one may graft or transplant cells infected with the recombinant lentivirus ex vivo, or infect cells in vivo.

Other Viral Vectors. The development and utility of viral vectors for gene delivery is constantly improving and evolving. Other viral vectors such as poxvirus; e.g., vaccinia virus (Gnant et al., 1999; Gnant et al., 1999), alpha virus; e.g., sindbis virus, Semliki forest virus (Lundstrom, 1999), reovirus (Coffey et al., 1998) and influenza A virus (Neumann et al., 1999) are contemplated for use in the present invention and may be selected according to the requisite properties of the target system.

In certain embodiments, vaccinia viral vectors are contemplated for use in the present invention. Vaccinia virus is a particularly useful eukaryotic viral vector system for expressing heterologous genes. For example, when recombinant vaccinia virus is properly engineered, the proteins are synthesized, processed and transported to the plasma membrane. Vaccinia viruses as gene delivery vectors have recently been demonstrated to transfer genes to human tumor cells, e.g., EMAP-II (Gnant et al., 1999), inner ear (Derby et al., 1999), glioma cells, e.g., p53 (Timiryasova et al., 1999) and various mammalian cells, e.g., P-450 (U.S. Pat. No. 5,506,138). The preparation, growth and manipulation of vaccinia viruses are described in U.S. Pat. Nos. 5,849,304 and 5,506,138 (each specifically incorporated herein by reference).

In other embodiments, sindbis viral vectors are contemplated for use in gene delivery. Sindbis virus is a species of the alphavirus genus (Garoff and Li, 1998) which includes such important pathogens as Venezuelan, Western and Eastern equine encephalitis viruses (Sawai et al., 1999; Mastrangelo et al., 1999). In vitro, sindbis virus infects a variety of avian, mammalian, reptilian, and amphibian cells. The genome of sindbis virus consists of a single molecule of single-stranded RNA, 11,703 nucleotides in length. The genomic RNA is infectious, is capped at the 5' terminus and polyadenylated at the 3' terminus, and serves as mRNA. Translation of a vaccinia virus 26S mRNA produces a polyprotein that is cleaved co- and post-translationally by a combination of viral and presumably host-encoded proteases to give the three virus structural proteins, a capsid protein (C) and the two envelope glycoproteins (E1 and PE2, precursors of the virion E2).

Three features of sindbis virus suggest that it would be a useful vector for the expression of heterologous genes. First, its wide host range, both in nature and in the laboratory. Second, gene expression occurs in the cytoplasm of the host cell and is rapid and efficient. Third, temperature-sensitive mutations in RNA synthesis are available that may be used to modulate the expression of heterologous coding sequences by simply shifting cultures to the non-permissive temperature at various time after infection. The growth and maintenance of sindbis virus is known in the art (U.S. Pat. No. 5,217,879, specifically incorporated herein by reference).

Chimeric Viral Vectors. Chimeric or hybrid viral vectors are being developed for use in therapeutic gene delivery and are contemplated for use in the present invention. Chimeric poxyiral/retroviral vectors (Holzer et al., 1999), adenoviral/retroviral vectors (Feng et al., 1997; Bilbao et al., 1997; Caplen et al., 1999) and adenoviral/adeno-associated viral vectors (Fisher et al., 1996; U.S. Pat. No. 5,871,982) have been described.

These "chimeric" viral gene transfer systems can exploit the favorable features of two or more parent viral species. For example, Wilson et al., provide a chimeric vector construct which comprises a portion of an adenovirus, AAV 5' and 3' ITR sequences and a selected transgene, described below (U.S. Pat. No. 5,871,983, specifically incorporate herein by reference).

The adenovirus/AAV chimeric virus uses adenovirus nucleic acid sequences as a shuttle to deliver a recombinant AAV/transgene genome to a target cell. The adenovirus nucleic acid sequences employed in the hybrid vector can range from a minimum sequence amount, which requires the use of a helper virus to produce the hybrid virus particle, to only selected deletions of adenovirus genes, which deleted gene products can be supplied in the hybrid viral production process by a selected packaging cell. At a minimum, the adenovirus nucleic acid sequences employed in the pAdA shuttle vector are adenovirus genomic sequences from which all viral genes are deleted and which contain only those adenovirus sequences required for packaging adenoviral genomic DNA into a preformed capsid head. More specifically, the adenovirus sequences employed are the cis-acting 5' and 3' inverted terminal repeat (ITR) sequences of an adenovirus (which function as origins of replication) and the native 5' packaging/enhancer domain, that contains sequences necessary for packaging linear Ad genomes and enhancer elements for the E1 promoter. The adenovirus sequences may be modified to contain desired deletions, substitutions, or mutations, provided that the desired function is not eliminated.

The AAV sequences useful in the above chimeric vector are the viral sequences from which the rep and cap polypeptide encoding sequences are deleted. More specifically, the AAV sequences employed are the cis-acting 5' and 3' inverted terminal repeat (ITR) sequences. These chimeras are characterized by high titer transgene delivery to a host cell and the ability to stably integrate the transgene into the host cell chromosome (U.S. Pat. No. 5,871,983, specifically incorporate herein by reference). In the hybrid vector construct, the AAV sequences are flanked by the selected adenovirus sequences discussed above. The 5' and 3' AAV ITR sequences themselves flank a selected transgene sequence and associated regulatory elements, described below. Thus, the sequence formed by the transgene and flanking 5' and 3' AAV sequences may be inserted at any deletion site in the adenovirus sequences of the vector. For example, the AAV sequences are desirably inserted at the site of the deleted E1a/E1b genes of the adenovirus. Alternatively, the AAV sequences may be inserted at an E3 deletion, E2a deletion, and so on. If only the adenovirus 5' ITR/packaging sequences and 3' ITR sequences are used in the hybrid virus, the AAV sequences are inserted between them.

The transgene sequence of the vector and recombinant virus can be a gene, a nucleic acid sequence or reverse transcript thereof, heterologous to the adenovirus sequence, which encodes a protein, polypeptide or peptide fragment of interest. The transgene is operatively linked to regulatory components in a manner which permits transgene transcription. The composition of the transgene sequence will depend upon the use to which the resulting hybrid vector will be put. For example, one type of transgene sequence includes a therapeutic gene which expresses a desired gene product in a host cell. These therapeutic genes or nucleic acid sequences typically encode products for administration and expression in a patient in vivo or ex vivo to replace or correct an inherited or non-inherited genetic defect or treat an epigenetic disorder or disease.

(x) Non-Viral Transformation

Suitable methods for nucleic acid delivery for transformation of an organelle, a cell, a tissue or an organism for use with the current invention are believed to include virtually any method by which a nucleic acid (e.g., DNA) can be introduced into an organelle, a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783, 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); or by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985). Through the application of techniques such as these, organelle(s), cell(s), tissue(s) or organism(s) may be stably or transiently transformed.

Injection: In certain embodiments, a nucleic acid may be delivered to an organelle, a cell, a tissue or an organism via one or more injections (i.e., a needle injection), such as, for example, either subcutaneously, intradermally, intramuscularly, intravenously or intraperitoneally. Methods of injection of vaccines are well known to those of ordinary skill in the art (e.g., injection of a composition comprising a saline solution). Further embodiments of the present invention include the introduction of a nucleic acid by direct microinjection. Direct microinjection has been used to introduce nucleic acid constructs into *Xenopus* oocytes (Harland and Weintraub, 1985).

Electroporation. In certain embodiments of the present invention, a nucleic acid is introduced into an organelle, a cell, a tissue or an organism via electroporation. Electroporation involves the exposure of a suspension of cells and DNA to a high-voltage electric discharge. In some variants of this method, certain cell wall-degrading enzymes, such as pectin-degrading enzymes, are employed to render the target recipient cells more susceptible to transformation by electroporation than untreated cells (U.S. Pat. No. 5,384,253, incorporated herein by reference). Alternatively, recipient cells can be made more susceptible to transformation by mechanical wounding.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

To effect transformation by electroporation in cells such as, for example, plant cells, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plant cells (Bates, 1994; Lazzeri, 1995). For example, the generation of transgenic soybean plants by electroporation of cotyledon-derived protoplasts is described by Dhir and Widholm in International Patent Application No. WO 9217598, incorporated herein by reference. Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

Calcium Phosphate. In other embodiments of the present invention, a nucleic acid is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

DEAE-Dextran: In another embodiment, a nucleic acid is delivered into a cell using DEAE-dextran followed by polyethylene glycol. In this manner, reporter plasmids were introduced into mouse myeloma and erythroleukemia cells (Gopal, 1985).

Sonication Loading. Additional embodiments of the present invention include the introduction of a nucleic acid by direct sonic loading. LTK⁻ fibroblasts have been transfected with the thymidine kinase gene by sonication loading (Fechheimer et al., 1987).

Liposome-Mediated Transfection. In a further embodiment of the invention, a nucleic acid may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is an nucleic acid complexed with Lipofectanine (Gibco BRL) or Superfect (Qiagen).

Liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa and hepatoma cells has also been demonstrated (Wong et al., 1980).

In certain embodiments of the invention, a liposome may be complexed with a hemagglutinating virus (HVJ). This has been shown to facilitate fusion with the cell membrane and promote cell entry of liposome-encapsulated DNA (Kaneda et al., 1989). In other embodiments, a liposome may be complexed or employed in conjunction with nuclear non-histone chromosomal proteins (HMG-1) (Kato et al., 1991). In yet further embodiments, a liposome may be complexed or employed in conjunction with both HVJ and HMG-1. In other embodiments, a delivery vehicle may comprise a ligand and a liposome.

Receptor Mediated Transfection: Still further, a nucleic acid may be delivered to a target cell via receptor-mediated delivery vehicles. These take advantage of the selective uptake of macromolecules by receptor-mediated endocytosis that will be occurring in a target cell. In view of the cell type-specific distribution of various receptors, this delivery method adds another degree of specificity to the present invention.

Certain receptor-mediated gene targeting vehicles comprise a cell receptor-specific ligand and a nucleic acid-binding agent. Others comprise a cell receptor-specific ligand to which the nucleic acid to be delivered has been operatively attached. Several ligands have been used for receptor-mediated gene transfer (Wu and Wu, 1987; Wagner et al., 1990; Perales et al., 1994; Myers, EPO 0273085), which establishes the operability of the technique. Specific delivery in the context of another mammalian cell type has been described (Wu and Wu, 1993; incorporated herein by reference). In certain aspects of the present invention, a ligand will be chosen to correspond to a receptor specifically expressed on the target cell population.

In other embodiments, a nucleic acid delivery vehicle component of a cell-specific nucleic acid targeting vehicle may comprise a specific binding ligand in combination with a liposome. The nucleic acid(s) to be delivered are housed within the liposome and the specific binding ligand is functionally incorporated into the liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a nucleic acid to cells that exhibit upregulation of the EGF receptor.

In still further embodiments, the nucleic acid delivery vehicle component of a targeted delivery vehicle may be a liposome itself, which will preferably comprise one or more lipids or glycoproteins that direct cell-specific binding. For example, lactosyl-ceramide, a galactose-terminal asialganglioside, have been incorporated into liposomes and observed an increase in the uptake of the insulin gene by hepatocytes (Nicolau et al., 1987). It is contemplated that the tissue-specific transforming constructs of the present invention can be specifically delivered into a target cell in a similar manner.

F. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986 and 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

Other examples of expression systems include STRATAGENE®'S COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

Primary mammalian cell cultures may be prepared in various ways. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented.

One embodiment of the foregoing involves the use of gene transfer to immortalize cells for the production of proteins. The gene for the protein of interest may be transferred as described above into appropriate host cells followed by culture of cells under the appropriate conditions. The gene for virtually any polypeptide may be employed in this manner. The generation of recombinant expression vectors, and the elements included therein, are discussed above. Alternatively, the protein to be produced may be an endogenous protein normally synthesized by the cell in question.

Examples of useful mammalian host cell lines are Vero and HeLa cells and cell lines of Chinese hamster ovary, W138, BHK, COS-7, 293, HepG2, NIH3T3, RIN and MDCK cells. In addition, a host cell strain may be chosen that modulates the expression of the inserted sequences, or modifies and process the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to insure the correct modification and processing of the foreign protein expressed.

A number of selection systems may be used including, but not limited to, HSV thymidine kinase, hypoxanthine-guanine phosphoribosyltransferase and adenine phosphoribosyltransferase genes, in tk-, hgprt- or aprt-cells, respectively. Also, anti-metabolite resistance can be used as the basis of selection for dhfr, that confers resistance to; gpt, that confers resistance to mycophenolic acid; neo, that confers resistance to the aminoglycoside G418; and hygro, that confers resistance to hygromycin.

G. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

Host cells may be derived from prokaryotes or eukaryotes, depending upon whether the desired result is replication of the vector or expression of part or all of the vector-encoded nucleic acid sequences. Numerous cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK™ Gold Cells (STRATAGENE®, La Jolla). Alternatively, bacterial cells such as E. coli LE392 could be used as host cells for phage viruses.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

H. Cell Propagation

Animal cells can be propagated in vitro in two modes: as non-anchorage dependent cells growing in suspension throughout the bulk of the culture or as anchorage-dependent cells requiring attachment to a solid substrate for their propagation (i.e., a monolayer type of cell growth). Non-anchorage dependent or suspension cultures from continuous established cell lines are the most widely used means of large scale production of cells and cell products. However, suspension cultured cells have limitations, such as tumorigenic potential and lower protein production than adherent T-cells.

Large scale suspension culture of mammalian cells in stirred tanks is a common method for production of recombinant proteins. Two suspension culture reactor designs are in wide use—the stirred reactor and the airlift reactor. The stirred design has successfully been used on an 8000 liter capacity for the production of interferon. Cells are grown in a stainless steel tank with a height-to-diameter ratio of 1:1 to 3:1. The culture is usually mixed with one or more agitators, based on bladed disks or marine propeller patterns. Agitator systems offering less shear forces than blades have been described. Agitation may be driven either directly or indirectly by magnetically coupled drives. Indirect drives reduce the risk of microbial contamination through seals on stirrer shafts.

The airlift reactor, also initially described for microbial fermentation and later adapted for mammalian culture, relies on a gas stream to both mix and oxygenate the culture. The gas stream enters a riser section of the reactor and drives circulation. Gas disengages at the culture surface, causing denser liquid free of gas bubbles to travel downward in the downcomer section of the reactor. The main advantage of this design is the simplicity and lack of need for mechanical mixing. Typically, the height-to-diameter ratio is 10:1. The airlift reactor scales up relatively easily, has good mass transfer of gases and generates relatively low shear forces.

The antibodies of the present invention are particularly useful for the isolation of antigens by immunoprecipitation. Immunoprecipitation involves the separation of the target antigen component from a complex mixture, and is used to discriminate or isolate minute amounts of protein. For the isolation of membrane proteins cells must be solubilized into detergent micelles. Non-ionic salts are preferred, since other agents such as bile salts, precipitate at acid pH or in the presence of bivalent cations. Antibodies are and their uses are discussed further, below.

III. GENERATING ANTIBODIES REACTIVE WITH KILLIN

In another aspect, the present invention contemplates an antibody that is immunoreactive with a Killin molecule of the present invention, or any portion thereof. An antibody can be a polyclonal or a monoclonal antibody. In a preferred embodiment, an antibody is a monoclonal antibody. Means for preparing and characterizing antibodies are well known in the art (see, e.g., Harlow and Lane, 1988).

Briefly, a polyclonal antibody is prepared by immunizing an animal with an immunogen comprising a polypeptide of the present invention and collecting antisera from that immunized animal. A wide range of animal species can be used for the production of antisera. Typically an animal used for production of anti-antisera is a non-human animal including rabbits, mice, rats, hamsters, pigs or horses. Because of the relatively large blood volume of rabbits, a rabbit is a preferred choice for production of polyclonal antibodies.

Antibodies, both polyclonal and monoclonal, specific for isoforms of antigen may be prepared using conventional immunization techniques, as will be generally known to those of skill in the art. A composition containing antigenic epitopes of the compounds of the present invention can be used to immunize one or more experimental animals, such as a rabbit or mouse, which will then proceed to produce specific antibodies against the compounds of the present invention. Polyclonal antisera may be obtained, after allowing time for antibody generation, simply by bleeding the animal and preparing serum samples from the whole blood.

It is proposed that the monoclonal antibodies of the present invention will find useful application in standard immunochemical procedures, such as ELISA and Western blot methods and in immunohistochemical procedures such as tissue staining, as well as in other procedures which may utilize antibodies specific to Killin-related antigen epitopes. Additionally, it is proposed that monoclonal antibodies specific to the particular Killin of different species may be utilized in other useful applications In general, both polyclonal and monoclonal antibodies against Killin may be used in a variety of embodiments. For example, they may be employed in antibody cloning protocols to obtain cDNAs or genes encoding other Killin. They may also be used in inhibition studies to analyze the effects of Killin related peptides in cells or animals. Anti-Killin antibodies will also be useful in immunolocalization studies to analyze the distribution of Killin during various cellular events, for example, to determine the cellular or tissue-specific distribution of Killin polypeptides under different points in the cell cycle. A particularly useful application of such antibodies is in purifying native or recombinant Killin, for example, using an antibody affinity column. The operation of all such immunological techniques will be known to those of skill in the art in light of the present disclosure.

Means for preparing and characterizing antibodies are well known in the art (see, e.g., Harlow and Lane, 1988; incorporated herein by reference). More specific examples of monoclonal antibody preparation are give in the examples below.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine.

As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

MAbs may be readily prepared through use of well-known techniques, such as those exemplified in U.S. Pat. No. 4,196, 265, incorporated herein by reference. Typically, this technique involves immunizing a suitable animal with a selected immunogen composition, e.g., a purified or partially purified Killin protein, polypeptide or peptide or cell expressing high levels of Killin. The immunizing composition is administered in a manner effective to stimulate antibody producing cells. Rodents such as mice and rats are preferred animals, however, the use of rabbit, sheep frog cells is also possible. The use of rats may provide certain advantages (Goding, 1986), but mice are preferred, with the BALB/c mouse being most preferred as this is most routinely used and generally gives a higher percentage of stable fusions.

Following immunization, somatic cells with the potential for producing antibodies, specifically B-lymphocytes (B-cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, 1986; Campbell, 1984). For example, where the immunized animal is a mouse, one may use P3-X63/Ag8, P3-X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with cell fusions.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976), and those using polyethylene glycol (PEG), such as 37% (v/v) PEG, by Gefter et al., (1977). The use of electrically induced fusion methods is also appropriate (Goding, 1986).

Fusion procedures usually produce viable hybrids at low frequencies, around $1\times10^{-6}$ to $1\times10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

IV. DIAGNOSING CANCERS INVOLVING KILLIN

Killin and the corresponding gene may be employed as a diagnostic or prognostic indicator of cancer. More specifically, point mutations, deletions, insertions or regulatory pertubations relating to Killin may cause cancer or promote cancer development, cause or promoter tumor progression at a primary site, and/or cause or promote metastasis. Other phenomena associated with malignancy that may be affected by Killin expression include angiogenesis and tissue invasion.

A. Genetic Diagnosis

One embodiment of the instant invention comprises a method for detecting variation in the expression of Killin. This may comprises determining that level of Killin or determining specific alterations in the expressed product. Obviously, this sort of assay has importance in the diagnosis of related cancers. Such cancer may involve cancers of the brain (glioblastomas, medulloblastoma, astrocytoma, oligodendroglioma, ependymomas), lung, liver, spleen, kidney, pancreas, small intestine, blood cells, lymph node, colon, breast, endometrium, stomach, prostate, testicle, ovary, skin, head and neck, esophagus, bone marrow, blood or other tissue. In particular, the present invention relates to the diagnosis of gliomas.

The biological sample can be any tissue or fluid. Various embodiments include cells of the skin, muscle, facia, brain, prostate, breast, endometrium, lung, head & neck, pancreas, small intestine, blood cells, liver, testes, ovaries, colon, skin, stomach, esophagus, spleen, lymph node, bone marrow or kidney. Other embodiments include fluid samples such as peripheral blood, lymph fluid, ascites, serous fluid, pleural effusion, sputum, cerebrospinal fluid, lacrimal fluid, stool or urine.

Nucleic acid used is isolated from cells contained in the biological sample, according to standard methodologies (Sambrook et al., 1989). The nucleic acid may be genomic DNA or fractionated or whole cell RNA. Where RNA is used, it may be desired to convert the RNA to a complementary DNA. In one embodiment, the RNA is whole cell RNA; in another, it is poly-A RNA. Normally, the nucleic acid is amplified.

Depending on the format, the specific nucleic acid of interest is identified in the sample directly using amplification or with a second, known nucleic acid following amplification. Next, the identified product is detected. In certain applications, the detection may be performed by visual means (e.g., ethidium bromide staining of a gel). Alternatively, the detection may involve indirect identification of the product via chemiluminescence, radioactive scintigraphy of radiolabel or fluorescent label or even via a system using electrical or thermal impulse signals (Affymax Technology; Bellus, 1994).

Following detection, one may compare the results seen in a given patient with a statistically significant reference group of normal patients and patients that have Killin-related pathologies. In this way, it is possible to correlate the amount or kind of Killin detected with various clinical states.

Various types of defects have been identified by the present inventors. Thus, "alterations" should be read as including deletions, insertions, point mutations and duplications. Point mutations result in stop codons, frameshift mutations or amino acid substitutions. Somatic mutations are those occurring in non-germline tissues. Germ-line tissue can occur in any tissue and are inherited. Mutations in and outside the coding region also may affect the amount of Killin produced, both by altering the transcription of the gene or in destabilizing or otherwise altering the processing of either the transcript (mRNA) or protein.

A cell takes a genetic step toward oncogenic transformation when one allele of a tumor suppressor gene is inactivated due to inheritance of a germline lesion or acquisition of a somatic mutation. The inactivation of the other allele of the gene usually involves a somatic micromutation or chromosomal allelic deletion that results in loss of heterozygosity (LOH). Alternatively, both copies of a tumor suppressor gene may be lost by homozygous deletion.

It is contemplated that other mutations in the Killin gene may be identified in accordance with the present invention. A variety of different assays are contemplated in this regard, including but not limited to, fluorescent in situ hybridization (FISH), direct DNA sequencing, PFGE analysis, Southern or Northern blotting, single-stranded conformation analysis (SSCA), RNAse protection assay, allele-specific oligonucleotide (ASO), dot blot analysis, denaturing gradient gel electrophoresis, RFLP and PCR™-SSCP.

(i) Primers and Probes

The term primer, as defined herein, is meant to encompass any nucleic acid that is capable of priming the synthesis of a nascent nucleic acid in a template-dependent process. Typically, primers are oligonucleotides from ten to twenty base pairs in length, but longer sequences can be employed. Primers may be provided in double-stranded or single-stranded form, although the single-stranded form is preferred. Probes are defined differently, although they may act as primers. Probes, while perhaps capable of priming, are designed to binding to the target DNA or RNA and need not be used in an amplification process. In particular embodiments, the probes or primers are labeled with radioactive species ($^{32}P$, $^{14}C$, $^{35}S$, $^{3}H$, or other label), with a fluorophore (rhodamine, fluorescein) or a chemilluminescent (luciferase).

(ii) Template Dependent Amplification Methods

A number of template dependent processes are available to amplify the marker sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1990, each of which is incorporated herein by reference in its entirety.

Briefly, in PCR™, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR™ amplification procedure may be performed in order to quantify the amount of mRNA amplified. Methods of reverse transcribing RNA into cDNA are well known and described in Sambrook et al., 1989. Alternative methods for reverse transcription utilize thermostable, RNA-dependent DNA polymerases. These methods are described in WO 90/07641 filed Dec. 21, 1990. Polymerase chain reaction methodologies are well known in the art.

Another method for amplification is the ligase chain reaction ("LCR"), disclosed in EPO No. 320 308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Application No. PCT/US87/00880, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention, Walker et al., (1992).

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification methods described in GB Application No. 2 202 328, and in PCT Application No. PCT/US89/01025, each of which is incorporated herein by reference in its entirety, may be used in accordance with the present invention. In the former application, "modified" primers are used in a PCR™-like, template- and enzyme-dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR (Kwoh et al., 1989; Gingeras et al., PCT Application WO 88/10315, incorporated herein by reference in their entirety). In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double-stranded by addition of second target specific primer, followed by polymerization. The double-stranded DNA molecules are then multiply transcribed by an RNA polymerase such as T7 or SP6. In an isothermal cyclic reaction, the RNA's are reverse transcribed into single-stranded DNA, which is then converted to double stranded DNA, and then transcribed once again with an RNA polymerase such as T7 or SP6. The resulting products, whether truncated or complete, indicate target specific sequences.

Davey et al., EPO No. 329 822 (incorporated herein by reference in its entirety) disclose a nucleic acid amplification process involving cyclically synthesizing single-stranded RNA ("ssRNA"), ssDNA, and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H(RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of *E. coli* DNA polymerase I), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR™" (Frohman, 1990; Ohara et al., 1989; each herein incorporated by reference in their entirety).

Methods based on ligation of two (or more) oligonucleotides in the presence of nucleic acid having the sequence of the resulting "di-oligonucleotide", thereby amplifying the di-oligonucleotide, may also be used in the amplification step of the present invention. Wu et al., (1989), incorporated herein by reference in its entirety.

(iii) Southern/Northern Blotting

Blotting techniques are well known to those of skill in the art. Southern blotting involves the use of DNA as a target, whereas Northern blotting involves the use of RNA as a target. Each provide different types of information, although cDNA blotting is analogous, in many aspects, to blotting or RNA species.

Briefly, a probe is used to target a DNA or RNA species that has been immobilized on a suitable matrix, often a filter of nitrocellulose. The different species should be spatially separated to facilitate analysis. This often is accomplished by gel electrophoresis of nucleic acid species followed by "blotting" on to the filter.

Subsequently, the blotted target is incubated with a probe (usually labeled) under conditions that promote denaturation and rehybridization. Because the probe is designed to base pair with the target, the probe will binding a portion of the target sequence under renaturing conditions. Unbound probe is then removed, and detection is accomplished as described above.

(iv) Separation Methods

It normally is desirable, at one stage or another, to separate the amplification product from the template and the excess primer for the purpose of determining whether specific amplification has occurred. In one embodiment, amplification products are separated by agarose, agarose-acrylamide or polyacrylamide gel electrophoresis using standard methods. See Sambrook et al., 1989.

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder, 1982).

(v) Detection Methods

Products may be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by a labeled probe. The techniques involved are well known to those of skill in the art and can be found in many standard books on molecular protocols. See Sambrook et al., 1989. For example, chromophore or radiolabel probes or primers identify the target during or following amplification.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

In addition, the amplification products described above may be subjected to sequence analysis to identify specific kinds of variations using standard sequence analysis techniques. Within certain methods, exhaustive analysis of genes is carried out by sequence analysis using primer sets designed for optimal sequencing (Pignon et al, 1994). The present invention provides methods by which any or all of these types of analyses may be used. Using the sequences disclosed herein, oligonucleotide primers may be designed to permit the amplification of sequences throughout the Killin gene that may then be analyzed by direct sequencing.

(vi) Kit Components

All the essential materials and reagents required for detecting and sequencing KILLIN and variants thereof may be assembled together in a kit. This generally will comprise preselected primers and probes. Also included may be enzymes suitable for amplifying nucleic acids including various polymerases (RT, Taq, Sequenase™ etc.), deoxynucleotides and buffers to provide the necessary reaction mixture for amplification. Such kits also generally will comprise, in suitable means, distinct containers for each individual reagent and enzyme as well as for each primer or probe.

(vii) Design and Theoretical Considerations for Relative Quantitative RT-PCR™

Reverse transcription (RT) of RNA to cDNA followed by relative quantitative PCR™ (RT-PCR™) can be used to determine the relative concentrations of specific mRNA species isolated from patients. By determining that the concentration of a specific mRNA species varies, it is shown that the gene encoding the specific mRNA species is differentially expressed.

In PCR™, the number of molecules of the amplified target DNA increase by a factor approaching two with every cycle of the reaction until some reagent becomes limiting. Thereafter, the rate of amplification becomes increasingly diminished until there is no increase in the amplified target between cycles. If a graph is plotted in which the cycle number is on the X axis and the log of the concentration of the amplified target DNA is on the Y axis, a curved line of characteristic shape is formed by connecting the plotted points. Beginning with the first cycle, the slope of the line is positive and constant. This is said to be the linear portion of the curve. After a reagent becomes limiting, the slope of the line begins to decrease and eventually becomes zero. At this point the concentration of the amplified target DNA becomes asymptotic to some fixed value. This is said to be the plateau portion of the curve.

The concentration of the target DNA in the linear portion of the PCR™ amplification is directly proportional to the starting concentration of the target before the reaction began. By determining the concentration of the amplified products of the target DNA in PCR™ reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundances of the specific mRNA from which the target sequence was derived can be determined for the respective tissues or cells. This direct proportionality between the concentration of the PCR™ products and the relative mRNA abundances is only true in the linear range of the PCR™ reaction.

The final concentration of the target DNA in the plateau portion of the curve is determined by the availability of reagents in the reaction mix and is independent of the original concentration of target DNA. Therefore, the first condition that must be met before the relative abundances of a mRNA species can be determined by RT-PCR™ for a collection of RNA populations is that the concentrations of the amplified PCR™ products must be sampled when the PCR™ reactions are in the linear portion of their curves.

The second condition that must be met for an RT-PCR™ experiment to successfully determine the relative abundances of a particular mRNA species is that relative concentrations of the amplifiable cDNAs must be normalized to some independent standard. The goal of an RT-PCR™ experiment is to determine the abundance of a particular mRNA species relative to the average abundance of all mRNA species in the sample. In the experiments described below, mRNAs for β-actin, asparagine synthetase and lipocortin II were used as external and internal standards to which the relative abundance of other mRNAs are compared.

Most protocols for competitive PCR™ utilize internal PCR™ standards that are approximately as abundant as the target. These strategies are effective if the products of the PCR™ amplifications are sampled during their linear phases. If the products are sampled when the reactions are approaching the plateau phase, then the less abundant product becomes relatively over represented. Comparisons of relative abundances made for many different RNA samples, such as is the case when examining RNA samples for differential expression, become distorted in such a way as to make differences in relative abundances of RNAs appear less than they actually are. This is not a significant problem if the internal standard is much more abundant than the target. If the internal standard is more abundant than the target, then direct linear comparisons can be made between RNA samples.

The above discussion describes theoretical considerations for an RT-PCR™ assay for clinically derived materials. The problems inherent in clinical samples are that they are of variable quantity (making normalization problematic), and that they are of variable quality (necessitating the co-amplification of a reliable internal control, preferably of larger size than the target). Both of these problems are overcome if the RT-PCR™ is performed as a relative quantitative RT-PCR™ with an internal standard in which the internal standard is an amplifiable cDNA fragment that is larger than the target cDNA fragment and in which the abundance of the mRNA encoding the internal standard is roughly 5-100 fold higher than the mRNA encoding the target. This assay measures relative abundance, not absolute abundance of the respective mRNA species.

Other studies may be performed using a more conventional relative quantitative RT-PCR™ assay with an external standard protocol. These assays sample the PCR™ products in the linear portion of their amplification curves. The number of PCR™ cycles that are optimal for sampling must be empirically determined for each target cDNA fragment. In addition, the reverse transcriptase products of each RNA population isolated from the various tissue samples must be carefully normalized for equal concentrations of amplifiable cDNAs. This consideration is very important since the assay measures absolute mRNA abundance. Absolute mRNA abundance can be used as a measure of differential gene expression only in normalized samples. While empirical determination of the linear range of the amplification curve and normalization of cDNA preparations are tedious and time consuming processes, the resulting RT-PCR™ assays can be superior to those derived from the relative quantitative RT-PCR™ assay with an internal standard.

One reason for this advantage is that without the internal standard/competitor, all of the reagents can be converted into a single PCR™ product in the linear range of the amplification curve, thus increasing the sensitivity of the assay. Another reason is that with only one PCR™ product, display of the product on an electrophoretic gel or another display method becomes less complex, has less background and is easier to interpret.

(viii) Chip Technologies

Specifically contemplated by the present inventors are chip-based DNA technologies such as those described by Hacia et al. (1996) and Shoemaker et al. (1996). Briefly, these techniques involve quantitative methods for analyzing large numbers of genes rapidly and accurately. By tagging genes with oligonucleotides or using fixed probe arrays, one can employ chip technology to segregate target molecules as high density arrays and screen these molecules on the basis of hybridization. See also Pease et al. (1994); Fodor et al. (1991).

B. Immunodiagnosis

Antibodies of the present invention can be used in characterizing the Killin content of healthy and diseased tissues, through techniques such as ELISAs and Western blotting.

This may provide a screen for the presence or absence of malignancy or as a predictor of future cancer.

The use of antibodies of the present invention, in an ELISA assay is contemplated. For example, anti-Killin antibodies are immobilized onto a selected surface, preferably a surface exhibiting a protein affinity such as the wells of a polystyrene microtiter plate. After washing to remove incompletely adsorbed material, it is desirable to bind or coat the assay plate wells with a non-specific protein that is known to be antigenically neutral with regard to the test antisera such as bovine serum albumin (BSA), casein or solutions of powdered milk. This allows for blocking of non-specific adsorption sites on the immobilizing surface and thus reduces the background caused by non-specific binding of antigen onto the surface.

After binding of antibody to the well, coating with a non-reactive material to reduce background, and washing to remove unbound material, the immobilizing surface is contacted with the sample to be tested in a manner conducive to immune complex (antigen/antibody) formation.

Following formation of specific immunocomplexes between the test sample and the bound antibody, and subsequent washing, the occurrence and even amount of immunocomplex formation may be determined by subjecting same to a second antibody having specificity for Killin that differs the first antibody. Appropriate conditions preferably include diluting the sample with diluents such as BSA, bovine gamma globulin (BGG) and phosphate buffered saline (PBS)/Tween®. These added agents also tend to assist in the reduction of nonspecific background. The layered antisera is then allowed to incubate for from about 2 to about 4 hr. at temperatures preferably on the order of about 25° to about 27° C. Following incubation, the antisera-contacted surface is washed so as to remove non-immunocomplexed material. A preferred washing procedure includes washing with a solution such as PBS/Tween®, or borate buffer.

To provide a detecting means, the second antibody will preferably have an associated enzyme that will generate a color development upon incubating with an appropriate chromogenic substrate. Thus, for example, one will desire to contact and incubate the second antibody-bound surface with a urease or peroxidase-conjugated anti-human IgG for a period of time and under conditions which favor the development of immunocomplex formation (e.g., incubation for 2 hr at room temperature in a PBS-containing solution such as PBS/Tween®).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation, e.g., using a visible spectrum spectrophotometer.

The preceding format may be altered by first binding the sample to the assay plate. Then, primary antibody is incubated with the assay plate, followed by detecting of bound primary antibody using a labeled second antibody with specificity for the primary antibody.

The antibody compositions of the present invention will find great use in immunoblot or Western blot analysis. The antibodies may be used as high-affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. Immunologically-based detection methods for use in conjunction with Western blotting include enzymatically-, radiolabel-, or fluorescently-tagged secondary antibodies against the toxin moiety are considered to be of particular use in this regard.

V. METHODS OF THERAPY

The present invention also involves, in another embodiment, the treatment of cancer. The types of cancer that may be treated, according to the present invention, is limited only by the involvement of Killin. By involvement, it is not even a requirement that Killin be mutated or abnormal—the overexpression of this tumor suppressor may actually overcome other lesions within the cell. Thus, it is contemplated that a wide variety of tumors may be treated using Killin therapy, including cancers of the brain, lung, liver, spleen, kidney, lymph node, pancreas, small intestine, blood cells, colon, stomach, breast, endometrium, prostate, testicle, ovary, skin, head and neck, esophagus, bone marrow, blood or other tissue.

In many contexts, it is not necessary that the tumor cell be killed or induced to undergo normal cell death or "apoptosis." Rather, to accomplish a meaningful treatment, all that is required is that the tumor growth be slowed to some degree. It may be that the tumor growth is completely blocked, however, or that some tumor regression is achieved. Clinical terminology such as "remission" and "reduction of tumor" burden also are contemplated given their normal usage.

A. Genetic Based Therapies

One of the therapeutic embodiments contemplated by the present inventors is the intervention, at the molecular level, in the events involved in tumorigenesis. Specifically, the present inventors intend to provide, to a cancer cell, an expression construct capable of providing Killin to that cell. Because the sequence homology between the human, mouse and dog genes, any of these nucleic acids could be used in human therapy, as could any of the gene sequence variants discussed above which would encode the same, or a biologically equivalent polypeptide. The lengthy discussion of expression vectors and the genetic elements employed therein is incorporated into this section by reference. Particularly preferred expression vectors are viral vectors such as adenovirus, adeno-associated virus, herpesvirus, vaccinia virus and retrovirus. Also preferred is liposomally-encapsulated expression vector.

Those of skill in the art are well aware of how to apply gene delivery to in vivo and ex vivo situations. For viral vectors, one generally will prepare a viral vector stock. Depending on the kind of virus and the titer attainable, one will deliver $1\times10^4$, $1\times10^5$, $1\times10^6$, $1\times10^7$, $1\times10^8$, $1\times10^9$, $1\times10^{10}$, $1\times10^{11}$ or $1\times10^{12}$ infectious particles to the patient. Similar figures may be extrapolated for liposomal or other non-viral formulations by comparing relative uptake efficiencies. Formulation as a pharmaceutically acceptable composition is discussed below.

Various routes are contemplated for various tumor types. The section below on routes contains an extensive list of possible routes. For practically any tumor, systemic delivery is contemplated. This will prove especially important for attacking microscopic or metastatic cancer. Where discrete tumor mass may be identified, a variety of direct, local and regional approaches may be taken. For example, the tumor may be directly injected with the expression vector. A tumor bed may be treated prior to, during or after resection. Following resection, one generally will deliver the vector by a catheter left in place following surgery. One may utilize the tumor vasculature to introduce the vector into the tumor by injecting a supporting vein or artery. A more distal blood supply route also may be utilized.

In a different embodiment, ex vivo gene therapy is contemplated. This approach is particularly suited, although not limited, to treatment of bone marrow associated cancers. In an ex vivo embodiment, cells from the patient are removed and maintained outside the body for at least some period of time. During this period, a therapy is delivered, after which the cells are reintroduced into the patient; hopefully, any tumor cells in the sample have been killed.

Autologous bone marrow transplant (ABMT) is an example of ex vivo gene therapy. Basically, the notion behind ABMT is that the patient will serve as his or her own bone marrow donor. Thus, a normally lethal dose of irradiation or chemotherapeutic may be delivered to the patient to kill tumor cells, and the bone marrow repopulated with the patients own cells that have been maintained (and perhaps expanded) ex vivo. Because, bone marrow often is contaminated with tumor cells, it is desirable to purge the bone marrow of these cells. Use of gene therapy to accomplish this goal is yet another way Killin may be utilized according to the present invention.

B. Protein Therapy

Another therapy approach is the provision, to a subject, of Killin polypeptide, active fragments, synthetic peptides, mimetics or other analogs thereof. The protein may be produced by recombinant expression means or, if small enough, generated by an automated peptide synthesizer. Formulations would be selected based on the route of administration and purpose including, but not limited to, liposomal formulations and classic pharmaceutical preparations.

C. Combined Therapy with Immunotherapy, Traditional Chemo- or Radiotherapy

Tumor cell resistance to DNA damaging agents represents a major problem in clinical oncology. One goal of current cancer research is to find ways to improve the efficacy of chemo- and radiotherapy. One way is by combining such traditional therapies with gene therapy. For example, the herpes simplex-thymidine kinase (HS-tk) gene, when delivered to brain tumors by a retroviral vector system, successfully induced susceptibility to the antiviral agent ganciclovir (Culver et al., 1992). In the context of the present invention, it is contemplated that Killin replacement therapy could be used similarly in conjunction with chemo- or radiotherapeutic intervention. It also may prove effective to combine Killin gene therapy with immunotherapy, as described above.

To kill cells, inhibit cell growth, inhibit metastasis, inhibit angiogenesis or otherwise reverse or reduce the malignant phenotype of tumor cells, using the methods and compositions of the present invention, one would generally contact a "target" cell with a Killin expression construct and at least one other agent. These compositions would be provided in a combined amount effective to kill or inhibit proliferation of the cell. This process may involve contacting the cells with the expression construct and the agent(s) or factor(s) at the same time. This may be achieved by contacting the cell with a single composition or pharmacological formulation that includes both agents, or by contacting the cell with two distinct compositions or formulations, at the same time, wherein one composition includes the expression construct and the other includes the agent.

Alternatively, the gene therapy treatment may precede or follow the other agent treatment by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one would contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either Killin or the other agent will be desired. Various combinations may be employed, where Killin is "A" and the other agent is "B", as exemplified below:

A/B/A  B/A/B  B/B/A  A/A/B  B/A/A  A/B/B  B/B/B/A  B/B/A/B
A/A/B/B  A/B/A/B  A/B/B/A  B/B/A/A  B/A/B/A  B/A/A/B  B/B/B/A
A/A/A/B  B/A/A/A  A/B/A/A  A/A/B/A  A/B/B/B  B/A/B/B  B/B/A/B

Other combinations are contemplated. Again, to achieve cell killing, both agents are delivered to a cell in a combined amount effective to kill the cell.

Agents or factors suitable for use in a combined therapy are any chemical compound or treatment method that induces DNA damage when applied to a cell. Such agents and factors include radiation and waves that induce DNA damage such as, γ-irradiation, X-rays, UV-irradiation, microwaves, electronic emissions, and the like. A variety of chemical compounds, also described as "chemotherapeutic agents," function to induce DNA damage, all of which are intended to be of use in the combined treatment methods disclosed herein. Chemotherapeutic agents contemplated to be of use, include, e.g., adriamycin, 5-fluorouracil (5FU), etoposide (VP-16), camptothecin, actinomycin-D, mitomycin C, cisplatin (CDDP) and even hydrogen peroxide. The invention also encompasses the use of a combination of one or more DNA damaging agents, whether radiation-based or actual compounds, such as the use of X-rays with cisplatin or the use of cisplatin with etoposide. In certain embodiments, the use of cisplatin in combination with a Killin expression construct is particularly preferred as this compound.

In treating cancer according to the invention, one would contact the tumor cells with an agent in addition to the expression construct. This may be achieved by irradiating the localized tumor site with radiation such as X-rays, UV-light, γ-rays or even microwaves. Alternatively, the tumor cells may be contacted with the agent by administering to the subject a therapeutically effective amount of a pharmaceutical composition comprising a compound such as, adriamycin, 5-fluorouracil, etoposide, camptothecin, actinomycin-D, mitomycin C, or more preferably, cisplatin. The agent may be prepared and used as a combined therapeutic composition, or kit, by combining it with a Killin expression construct, as described above.

Agents that directly cross-link nucleic acids, specifically DNA, are envisaged to facilitate DNA damage leading to a synergistic, antineoplastic combination with Killin. Agents such as cisplatin, and other DNA alkylating agents may be used. Cisplatin has been widely used to treat cancer, with efficacious doses used in clinical applications of 20 mg/m² for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25-75 mg/m$^2$ at 21 day intervals for adriamycin, to 35-50 mg/m$^2$ for etoposide intravenously or double the intravenous dose orally.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage DNA, on the precursors of DNA, the replication and repair of DNA, and the assembly and maintenance of chromosomes. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The inventors propose that the local or regional delivery of Killin expression constructs to patients with cancer will be a very efficient method for treating the clinical disease. Similarly, the chemo- or radiotherapy may be directed to a particular, affected region of the subjects body. Alternatively, systemic delivery of expression construct and/or the agent may be appropriate in certain circumstances, for example, where extensive metastasis has occurred.

In addition to combining Killin therapies with chemo- and radiotherapies, it also is contemplated that combination with other gene therapies will be advantageous. For example, targeting of Killin and p53 mutations at the same time may produce an improved anti-cancer treatment. Any other tumor-related gene conceivably can be targeted in this manner, for example, p21, Rb, APC, DCC, NF-1, NF-2, BCRA2, p16, FHIT, WT-1, MEN-I, MEN-II, BRCA1, VHL, FCC, MCC, ras, myc, neu, raf, erb, src, fms, jun, trk, ret, gsp, hst, bcl and abl.

It also should be pointed out that any of the foregoing therapies may prove useful by themselves in treating a Killin. In this regard, reference to chemotherapeutics and non-Killin gene therapy in combination should also be read as a contemplation that these approaches may be employed separately.

E. Formulations and Routes for Administration to Patients

Where clinical applications are contemplated, it will be necessary to prepare pharmaceutical compositions—expression vectors, virus stocks, proteins, antibodies and drugs—in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, described supra. Of particular interest is direct intratumoral administration, perfusion of a tumor, or administration local or regional to a tumor, for example, in the local or regional vasculature or lymphatic system, or in a resected tumor bed.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

VI. KITS

According to the present invention, there are provided kits for detecting killin mutations and Killin expression. The kit of the present invention can be prepared by known materials and techniques which are conventionally used in the art. Generally, kits comprises separate vials or containers for the various reagents, such as probes, primers, enzymes, antibodies, etc. The reagents are also generally prepared in a form suitable for preservation by dissolving it in a suitable solvent. Examples of a suitable solvent include water, ethanol, various buffer solutions, and the like. The various vials or containers are often held in blow-molded or injection-molded plastics.

VII. TRANSGENICS

In one embodiment of the invention, transgenic animals are produced which contain a functional transgene encoding a functional Killin polypeptide or variants thereof. Transgenic animals expressing Killin transgenes, recombinant cell lines derived from such animals and transgenic embryos may be useful in methods for screening for and identifying agents that induce or repress function of Killin. Transgenic animals of the present invention also can be used as models for studying indications such as cancers. The promoter controlling the transgene may be one that is capable of tissue specific or inducible expression. Within a particularly preferred embodiment, transgenic mice are generated which overexpress Killin or express a mutant form of the polypeptide.

In one embodiment of the invention, a Killin transgene is introduced into a non-human host to produce a transgenic animal expressing a human or murine Killin gene. The transgenic animal is produced by the integration of the transgene into the genome in a manner that permits the expression of the transgene. Methods for producing transgenic animals are generally described by Wagner and Hoppe (U.S. Pat. No. 4,873,191; which is incorporated herein by reference), Brinster et al. (1985; which is incorporated herein by reference in its entirety) and in "Manipulating the Mouse Embryo; A Laboratory Manual" (1994); which is incorporated herein by reference in its entirety).

It may be desirable to replace the endogenous Killin by homologous recombination between the transgene and the endogenous gene so as to measure the effects of only the transgene's expression. Typically, a Killin gene flanked by genomic sequences is transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish. Alternatively, the endogenous gene may be eliminated by deletion as in the preparation of "knock-out" animals, optionally followed by insertion of the Killin transgene. the absence of one or both alleles of a Killin gene in "knock-out" mice permits the study of the effects that a reduction in or loss of Killin protein has on a cell in vivo. Knock-out mice also provide a model for the development of Killin-related cancers.

As noted above, transgenic animals and cell lines derived from such animals may find use in certain testing experiments. In this regard, transgenic animals and cell lines capable of expressing wild-type or mutant Killin may be exposed to test substances. These test substances can be screened for the ability to enhance wild-type Killin expression and or function or impair the expression or function of mutant Killin.

VIII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials & Methods

Cell culture. The p53-inducible H1299 lung cancer cell line p53-3 was a gift from XB Chen et al. (1996). Human colorectal adenocarcinoma cell lines DLD-1 was from ATTC. DLD-1(tetR) (with a tetracycline-regulated transactivator) and DLD1 with an inducible wild-type p53 expression were kindly provided by Yu et al. (1999). Cos-1 cells were gift of J. Flanagan (Harvard Medical School). Cell culture conditions and the inductions of wild-type p53, GFP, and GFP-Killin expression in both H1299 and DLD-1 cells were carried out essentially as described previously (Yu et al., 1999; Chen et al., 1996; Stein et al., 2004). Proliferation assays were performed by seeding 5,000 cells in each well of six-well tissue culture dishes in duplicate for each data point and incubated at 37° C. for 5 days, during which cells were trypsinized and counted using the Coulter cell counter (Beckman Coulter).

Cell transfection, RNA isolation, FDD, Northern blot analysis, Real time RT-PCR, and cDNA library screening. Cell transfection, FDD screening and Northern Blot analysis were carried out essentially as described previously (Stein et al., 2004). Quantitative real-time RT-PCR assays for endogenous killin mRNA expression were conducted with killin specific primers, 5'-TACACAAGCACCCACATC-3' (SEQ ID NO:5) and 5'-TACACAAGCACCCACATC-3'(SEQ ID NO:6). The predicted killin-specific RT-PCR product is 151 bp in size. For sample normalization, a constitutively expressed house-keeping gene glyceraldehyde-3-phosphate dehydrogenase(GAPDH), was measured using primers, 5'-CATGAGAAGTATGACAACAGCCT-3' (SEQ ID NO:7) and 5'-AGTCCTTCCACGATACCAAAGT-3'(SEQ ID NO: 8) which specifically amplify GAPDH mRNA. After DNase I treatment with a MessageClean kit (GenHunter) to remove any chromosomal DNA, total RNA from each sample was reverse-transcribed using an oligo $dT_{20}$ primer (GenHunter) and Superscriptase (Invitrogene). All real-time PCR reactions were performed on an iCycler iQ(Bio-Rad), using iQ™ SYBR Green Supermix (Bio-Rad) as instructed by the manufacturer. The amplification protocol consisted of 3 min denaturation at 95° C. followed by 45 cycles of amplification (95° C. for 10 s, 63° C. for 45 s). Each sample was run in triplicate in separate wells to permit quantification of the killin and GAPDH mRNA expression. All data were calculated by the comparative Ct method to determine relative gene expression level. A 4.1 kb full-length killin cDNA was isolated from a human kidney cDNA library (Stratagene) using the killin FDD cDNA probe and completely sequenced.

RNA Interference. RNAi sequence targeting killin, 5'-GGATACACGGGCCACAGTC-3'(SEQ ID NO:9)(positions 153 to 171) was selected following the instruction from oligoengine.com. Primers used were: forward primer (64mer) 5'-GATCCCCGGATACACGGGCCACAGTCT-TCAAGAGAGACTGTGGCCCGTGT ATCCTTTTTG-GAAA-3' (SEQ ID NO:10)and reverse primer (64mer)'-AGCTTTTCCAAAAAGGATACACGGGCCACAGTCTC-TCTTGAAGACTGTGGC CCG TGTATCCGGG-3' (SEQ ID NO:11). The annealed RNAi template was cloned into BglII and HindIII sites of pSUPER27 (gift from R. Agami, The Netherlands Cancer Institute, Amsterdam, Netherlands). The RNAi construct was confirmed by sequencing.

Dual Luciferase Reporter Assay. The p53 binding site located within human Killin promoter was amplified by PCR from the genomic DNA of human HEK293T cells using the following forward and reverse primers based on the human genome database:

(SEQ ID NO:12)
5'-GGTACCTCTGGGTGCGAGCGCAGAG-3'

(SEQ ID NO:13)
5'-AGATCTCGTTATCCTCGCCTCGCGTTG-3'

The 140 bp PCR product was cloned first into PCR-TRAP cloning vector and then shuttled into the KpnI and BglII sites of the pGL3-basic vector (Promega). H1299 cells (p53 null) were cultured overnight in 12-well plate and subsequently co-transfected with pGL3 or pGL3-PKillin reporter plasmid with either pCEP4-p53 (p53) (Stein et al., 2004) expressing wild-type p53, or pRc-p53 expressing a loss of function mutant p53 (p53-mut) (Taniura et al., 1999). Following 24 hrs of transfection, cells were lysed and the luciferase activity was determined using the dual luciferase reporter assay system (Promega) and Monolight™ 3010 luminometer (BD PharMingen). All experiments were performed in duplicate. The pRL-CMV plasmid containing the *Renilla luciferase* reporter gene (Promega) was used to normalize the transfection efficiency.

Inducible GFP-Killin expression. The entire coding region of Killin (aa 2-178) was amplified by PCR using primers:

(SEQ ID NO:14)
B1-5'-CGCGGATCCGATCGCCCGGGGCCAGGCTCC-3'

(SEQ ID NO:15)
B2-5'-CGCGGATCCTCAGTCCTTTGGCTTGCTCTT-3'

After cloning into PCR-TRAP (GenHUnter), the insert was subcloned into the BamHI site of pEGFP-C1 (Clontech) to allow in-frame fusion of Killin to EGFP. The GFP-Killin fusion was then shuttled into pTRE2 vector (Clonetech) as a NheI-HindIII fragment to allow tetracycline regulated expression after stably transfected into DLD-1 (TetR) cell line. GFP alone was also subcloned into pTRE2 from pEGFP-C1 as a NheI-DraI fragment. All fusion constructs were verified by DNA sequencing.

FACS analysis, immunoblotting and fluorescent microscopy. FACS analysis and immunoblotting including sources of antibodies were essentially as described previously (Stein et al., 2004). Fluorescent microscopy of GFP and GFP-killin expression in vivo was carried out using a Zeiss 200M inverted fluorescence microscope (Carl Zeiss Microimage, Germany) with temperature- and $CO_2$-controlled chamber. Captured images were analyzed using the Openlab software (Improvision, Lexington, Mass.). For confocal microscopy, cells were grown on cover slips, transfected with GFP-PCNA or GFP-Killin, fixed and stained with DAPI for DNA colocalization, mounted using the ProLong antifade (Molecular Probes) and examined with a Zeiss Axioplan 2 microscope using the 63× oil immersion objective. Digital images were captured with an ORCA-ER camera and selected images were processed by deconvolution microscopy using the OpenLab software.

DNA binding assays. In vitro transcribed and translated Killin cloned into pcDNA3.1 (Invitrogen) (K), or vector alone (V) were labeled with $^{35}S$ using Translabel (ICN) and a TnT kit (Promega). The labeled Killin and vector control were incubated with either single-stranded (ss) or double-stranded (ds) DNA cellulose (Sigma). After washing with PBS, bound proteins were resolved on a 15% SDS-PAGE gel, dried onto a 3M paper before autoradiography. For peptide binding, 42 aa of Killin/N8-50 peptide (MW: 5007 dalton) was synthesized and verified with mass spec by Sigma-Genosys at a purity of at least 70%. The peptide was dissolved in PBS as 1 mg/mL stock solution before use. For in vitro DNA binding assay, 3 primers (32-35 bases in length) with arbitrary sequences were designed:

```
LL:                                           (SEQ ID NO:16)
5'-TTTGCACGTCGGATCCGACCCAGACTACGGAGGCC-3'

RLM:                                          (SEQ ID NO:17)
5'-GGCCTCCGTAGTCTGGGTCGGATCCGACGTGC-3'

RL:                                           (SEQ ID NO:18)
5'-CCGGAGGCATCAGACGGTCGGATCCGACGTGC-3')
```

After annealing, probes for artificial replication fork (LL and RL) or double-stranded DNA template (LL and RLM) were end-labeled with $\alpha$-$^{32}P$-dATP (Perkin-Elmer) using Klenow (New England Biolab). Single-stranded oligonucleotide (LL) was end-labeled with $\gamma$-$^{32}P$-dATP (Perkin-Elmer) using T4 polynucleotide kinase (New England Biolab). After purifying with Sephadex-G50 spin columns (Roche), the labeled probes (200,000 CPM each) were mixed with an increasing amount of Killin/N8-50 peptide in the presence of 20 mM Tris-Cl (pH 8.4), 25 mM KCl, 1.5 mM $MgCl_2$ and 100 μg/mL of BSA. The reaction mixtures were incubated at RT for 30 min and separated on a 6% polyacrylamide gel with 1×TBE buffer. After drying the gel onto a Whatman No. 1 filter paper, the DNA-protein complexes were visualized by autoradiography. For binding kinetics, bands from DNA-peptide complex were excised and the radioactivity was determined by scintillation counting. To determine the stability of the DNA-Killin peptide complex, 0.5 μg of either double-stranded (RF form) or single-stranded (viral form) of PhiX174 bacterial phage DNA (New England Biolab) were incubated at room temperature for 30 min with 1 μg of Killin/N8-50 peptide in a 20 μL reaction. The samples were then resolved on a 0.8% TAE agarose gel and stained with ethidium bromide.

In vitro DNA synthesis assay. pUC18 plasmid from exponentially growing (log phase) bacteria was purified and used as a template for in vitro DNA synthesis assay using a HotPrime DNA labeling kit (GenHunter). For each in vitro DNA synthesis assay, 0.8 μg of theta form (incompletely replicated) pUC18 was mixed with an increasing amount of Killin/N8-50 peptide in the presence of 2.5 μCi of $\alpha$-$^{32}P$-dATP and 1× labeling buffer containing 200 μM of dNTP(-dATP). After 1 hour, 5 units of Klenow (NEB) were added to each reaction to initiate DNA synthesis reaction at 37° C. After 30 min, the reaction was stopped with 6 μl of 100 mM EDTA. Mini Quick DNA Spin columns (Roche Applied Science) were utilized to remove unincorporated nucleotides, and rate of DNA synthesis was determined by scintillation counting of purified high molecular weight DNA.

Random Mutagenesis, deletion analysis, and genetic screen of killin. Mutagenesis experiments were performed using EMS (ethylmethanesulfonate) (Sigma) as described previously with minor modification. Exponentially growing XL-1 blue with pQE32-Killin was harvested by centrifugation, washed, and resuspended in minimal A buffer (10.5 g of $K_2HPO_4$, 4.5 g of $KH_2PO_4$, 1 g of $[NH_4]_2SO4$, and 0.5 g of sodium citrate:$2H_2O$ in 1 liter). EMS was added to the cells at a concentration of 140 μM for 1 hour during continuous shaking at 37° C. After washing with minimal A buffer, cells was diluted 1:10 in LB medium and grown for 6 hrs at 37° C. before mutagenized plasmids were purified and transformed into either GH1 (without repression, GenHunter) or XL-1 blue (with repression, Stratagene) competent cells. Ampicilin resistant colonies were scored after an overnight incubation.

For deletion analysis, PCR was performed to amplify different regions of Killin as specificed. PCR primer sequences used for the deletions are listed below:

```
L-1 (32mer):                                  (SEQ ID NO:19)
5'-CGCGGATCCTGGATCGCCCGGGGCCAGGCTCC-3'

L-8 (26mer):                                  (SEQ ID NO:20)
5'-GGATCCTGGCGCGCCCCGGCCGGACC-3'

L-11 (26mer):                                 (SEQ ID NO:21)
5'-GGATCCTGGGCCGGACCGTGCACGTT-3'

L-124 (26mer):                                (SEQ ID NO:22)
5'-GGATCCTCCCGAAGGAGCGCTGTCGG-3'

R-43 (28mer):                                 (SEQ ID NO:23)
5'-GGATCCTCATAGGTCTCCTCGCCCCGCC-3'

R-49 (29mer):                                 (SEQ ID NO:24)
5'-GGATCCTACCTCCTTTTGAACCCTCCTAG-3'

R-85 (27mer):                                 (SEQ ID NO:25)
5'-GGATCCTAGCCTCCGGAGCTATCACTG-3'

R-97 (27mer):                                 (SEQ ID NO:26)
5'-GGATCCTAGGCAAGAGCACCCCGAGCA-3'

R-178 (27mer):                                (SEQ ID NO:27)
5'-CGCGGATCCTCAGTCCTTTGGCTTGCTCTT-3'
```

The obtained PCR products were first cloned into PCR-TRAP cloning vector and then subcloned as BglII fragments into the BamHI site of the pQE32 6XHIS-tag expression vector (Qiagen). The expression vectors were transformed into XL-1 blue under transcription repression for the transgene (-IPTG). All killin deletion plasmid constructs were verified by DNA sequencing before being transformed into GH1 competent cells (GenHunter), which does not have lacI$^q$ (no repression for transcription), to allow scoring for inhibition of bacteria colony formation when selected with ampicillin. As a negative control, all vectors were simultaneously transformed into XL-1 blue cells, which gave near confluent transformants under transcription repression for all constructs. Similar deletion constructs were also made as GFP fusion protein as described above and transiently transfected into the H1299 cells to visualized their ability to cause cell apoptosis based on nuclear chromosome condensation.

In vitro SV40 DNA replication assay. The SV40 origin (ori) of replication-dependent in vitro DNA replication was carried out essentially as described previously (Li and Kelly, 1984) with minor modifications. Briefly, the source of SV40 large T antigen was from HEK293T cells (GenHunter). The SV40 ori-containing plasmid vector pAPtag-2 (GenHunter) and a negative control vector pUC18 that lacks SV40 ori were used as templates for the in vitro DNA replication assays. 10 µg of nuclear protein extracts and 250 ng of plasmid DNA template were used for each assay. Nascent DNA synthesis in the absence and presence of Killin/N8-50 peptide after $^{32}$P-α-dATP labeling was analyzed on a 6% TBE PAGE gel, dried onto a 3 M paper (Whatman) and visualize by autoradiography.

Example 2

Results

Figure 8:
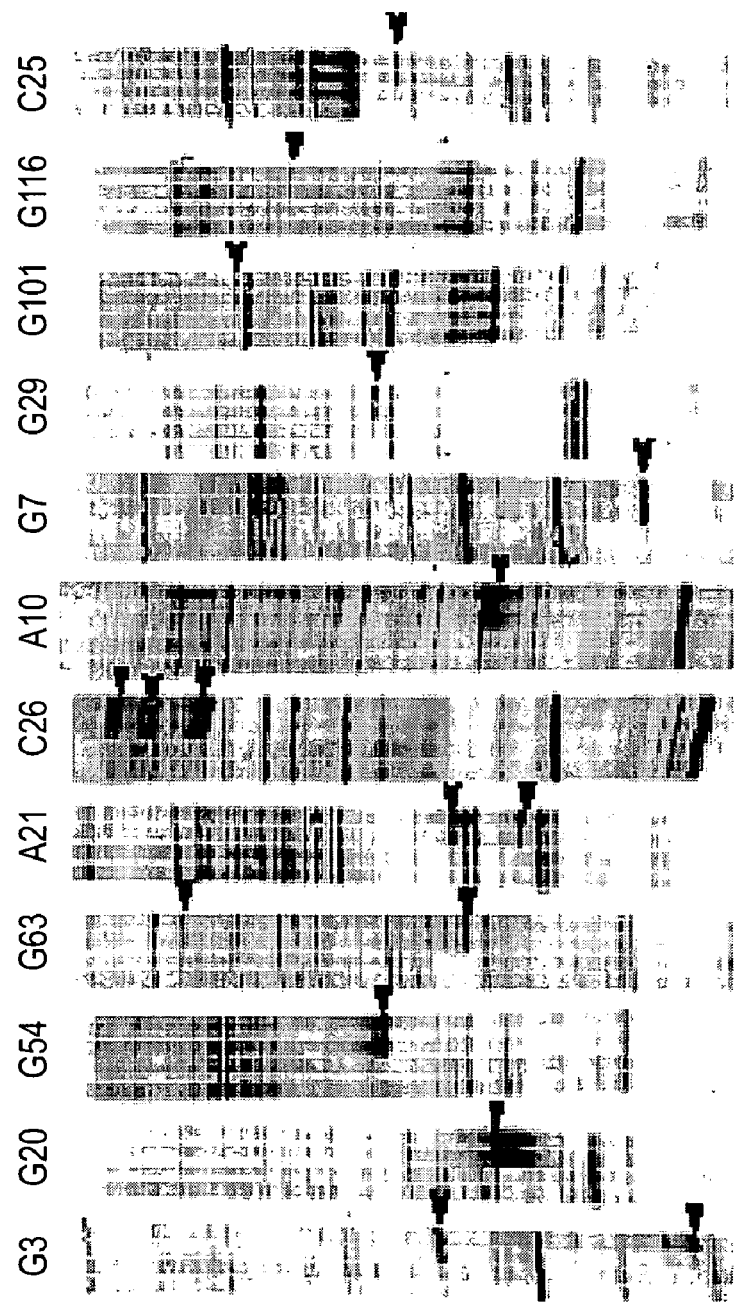
FIG. 8—Representative FDD (in gray scale) detecting p53 regulated changes in gene expression following tetracycline removal from DLD-1 or H1299 cells with inducible wild-type p53. Four RNA samples representing 9 and 12 hours with Tet (left two lanes) and without Tet (right two lanes), respectively were compared. Primer combinations detecting the changes in gene expression are as indicated (e.g., G3=G-anchor+ HAP-3, etc.). Four of the clearly induced genes (G20, G54, G63 and G116) after sequencing turned out to be p53 itself, validating the comprehensiveness and precision of the inventors' FDD platform. The nature of other p53 induced genes is summarized in Table 6.

High-throughput fluorescent differential display (FDD) screening for p53 target genes. In an attempt to systematically identify p53 target genes that are involved in S-phase checkpoint control, the inventors employed the comprehensive FDD screening strategy that they pioneered (Liang and Pardee, 1992; Cho et al., 2001; Liang 2002; Liang and Pardee, 2003; Yang and Liang, 2004). They chose two cell types in which p53 mutations had been clearly linked to human cancer, the p53-null human lung carcinoma cell line H1299 (Chen et al., 1996) and the DLD-1 colon cancer cell line (Yu et al., 1999). Both cell lines contained tetracycline-regulated expression of wild-type p53 tumor suppressor gene and underwent apoptosis within 24-48 hrs following tetracycline withdraw (Chen et al., 1996; Yu et al., 1999; Stein et al., 2004). One of the greatest advantages of Differential Display (DD) over many other methods for differential gene expression studies is that it allows simultaneous comparison of more than just two RNA samples, so better controls can be built in to cut down the biological variables or "noise" that are p53-independent (Liang and Pardee, 2003). For example, to control for the effects of elapse of time, washing the cells and media change to remove tetracycline in order to turn on p53 expression, the inventors included, in parallel, a control set of plates containing the same cells that were washed and incubated with new media with tetracycline (no p53 induction). RNA and protein samples were isolated and the induction of p53 and subsequent cell apoptosis were confirmed (FIGS. 1A-D). After DNase I treatment to remove any residual chromosomal DNA, four total RNA samples from 9 and 12 hr time points without and with the induction of p53 were reverse transcribed and processed for comprehensive FDD analysis. After screening through 192 combinations of DD primers (G-anchor in combinations with arbitrary 13mers HAP(1-120), A-anchor with HAP(1-24) and C-anchor with HAP(1-48), over a dozen candidate p53 target genes were identified (FIG. 8 & Table 6). This represented about 40% coverage of all the genes expressed in a cell based on a recent theoretical model of DD (Yang and Liang, 2004). DNA sequence analysis revealed that 4 of them, G20, G54, G63 and G116 corresponded to the wild-type p53 transgene itself (Table 6). Among these were also several known bonafide p53 target genes, including human homolog of mdm-2 (found twice, A10 and G10) and p21 (A21), while the rest of the candidate p53 target genes including G101 (killin) and NDRG1 were either novel genes or novel p53 targets (Stein et al., 2004) (Table 6). The findings of p53 induction as well as other major known p53 target genes several times by FDD demonstrated an excellent gene coverage and accuracy of our FDD platform, since the method is non-biased and does not require any prior knowledge in gene sequences being detected (Yang and Liang, 2004). While the inventors have previously shown that NDRG1 is necessary for p53-mediated apoptosis (Stein et al., 2004), here the inventors focus on the characterization of killin and show that it is a novel p53 target gene which functions directly in S-phase control and apoptosis.

TABLE 6 p53 target genes identified by comprehensive FDD Screening

| FDD band | Gene identity | Anchor used | H-AP used | Known Target |
|---|---|---|---|---|
| G3 | NDRG1 | G | H-AP-3 | Yes |
| G7 | Novel | G | H-AP-3 | No |
| G10 | HDM-2 | G | H-AP-10 | Yes |
| G14 | Novel | G | H-AP-14 | No |
| G17 | NDRG1 | G | H-AP-17 | Yes |
| G20 | p53 | G | H-AP-20 | Yes |
| G29 | Pir-121 | G | H-AP-29 | Yes-No |
| G40 | Glutaminase | G | H-AP-40 | No |
| G54 | p53 | G | H-AP-54 | Yes |
| G63 | p53 | G | H-AP-63 | Yes |
| G77 | Novel | G | H-AP-77 | No |
| G101 (killin) | Novel | G | H-AP-101 | No |
| G116 | p53 | G | H-AP-116 | No |
| A9 | PP2C-gamma-like | A | H-AP-10 | No |
| A10 | HDM-2 | A | H-AP-10 | Yes |
| A21 | p21 | A | H-AP-21 | Yes |
| C25 | Tis11d | C | H-AP-25 | No |
| C26 | Novel | C | H-AP-26 | No |
| C29 | Pir-121 | C | H-AP-29 | Yes-no |

Figures 1A, 1B:
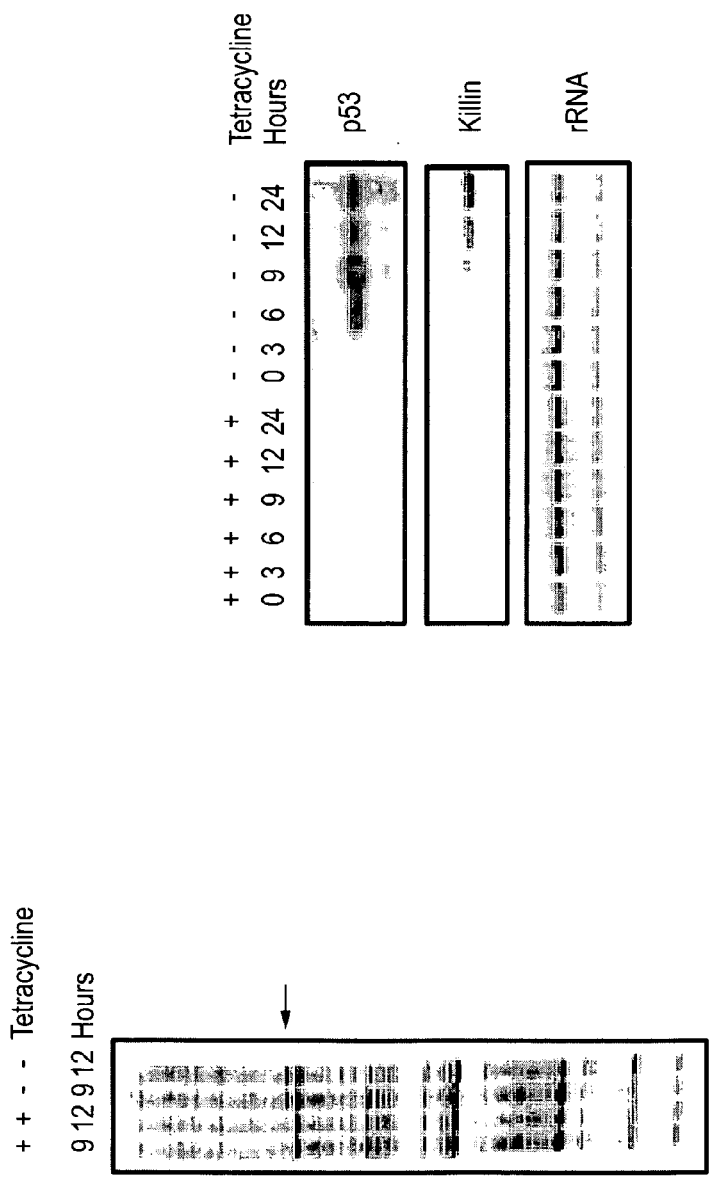
FIGS. 1A-D—Identification and Confirmation of killin (G101) as a Novel p53 Target Gene.
Figures 1C, 1D:
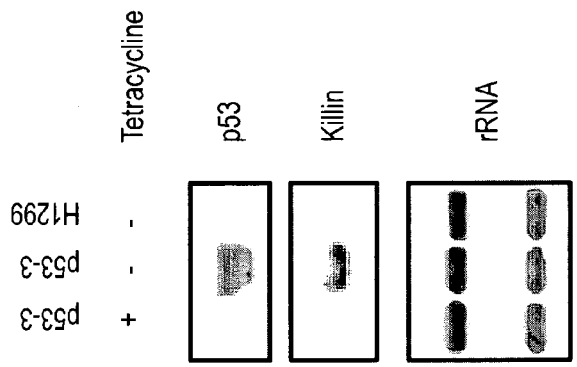

Identification of killin as a novel p53 target gene. The identification of killin as a p53 target gene by FDD and its confirmation by Northern blot analysis using the cDNA fragment recovered from FDD was shown in FIGS. 1A-B. The induction of the 4 kb killin mRNA following tetracycline withdraw was evident from 9 hrs, which was slightly behind the induction of p53 as expected. To rule out the effect of tetracycline on killin expression that was independent of p53, H1299 (p53 null) parental cells grown in the absence of tetracycline was included as a negative control, which confirmed that killin expression was indeed p53-dependent (FIG. 1C). DNA sequence analysis of the 542 bp killin cDNA recovered from FDD revealed that killin is a novel gene, which is normally expressed at low level detectable only in kidney and lung. Using the killin FDD cDNA as a probe, a 4.1 kb full-length cDNA for the gene was isolated from a human kidney cDNA library. After complete sequencing, the cDNA was shown to encode a novel and small 20 kDa basic protein of 178 amino acids with an apparent pI of 11.3 (FIG. 1D). An in-frame stop codon was found within 15 bases upstream of the predicted translation start site of Killin. Bioinformatic analysis of Killin indicated that the protein did not share any homology to any known proteins from any species, except two putative nuclear localization domains were noted (FIG. 1D).

Figure 2A:
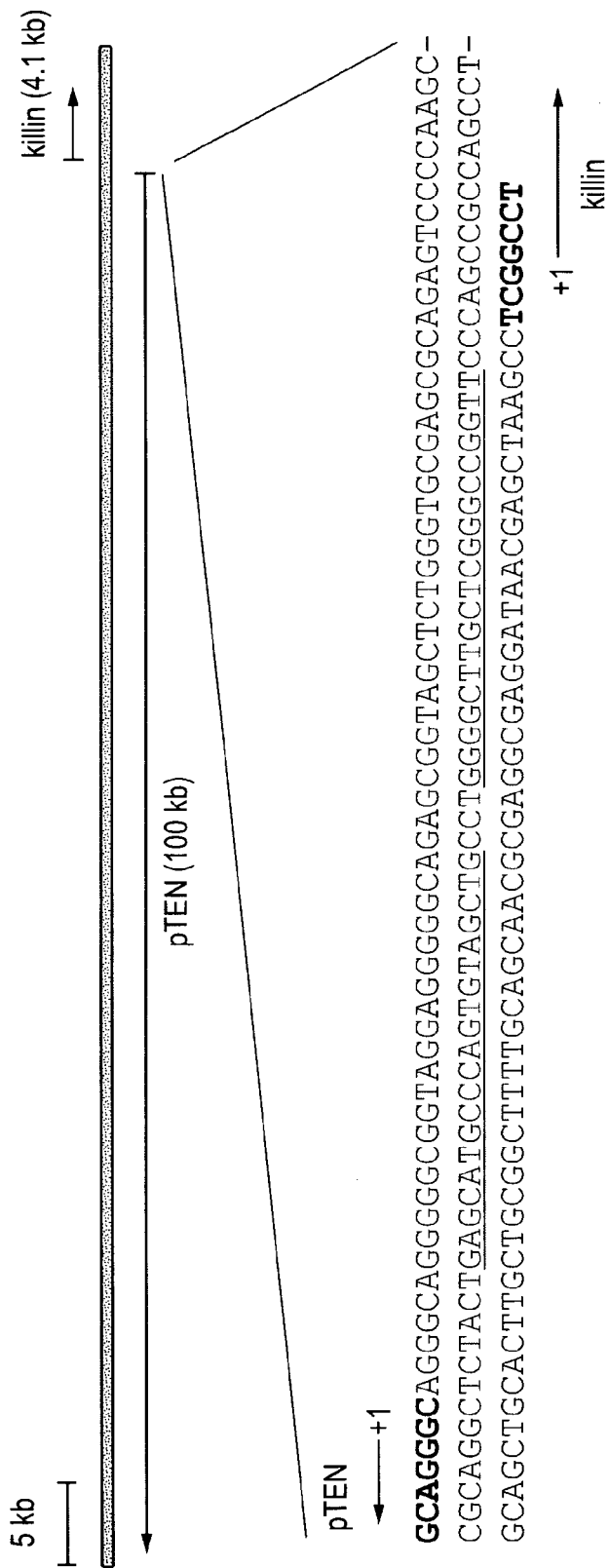
FIGS. 2A-B—Killin is Localized in Close Proximity to pTEN Tumor-Suppressor Gene and is Transcriptionally Activated by p53.
Figure 2B:
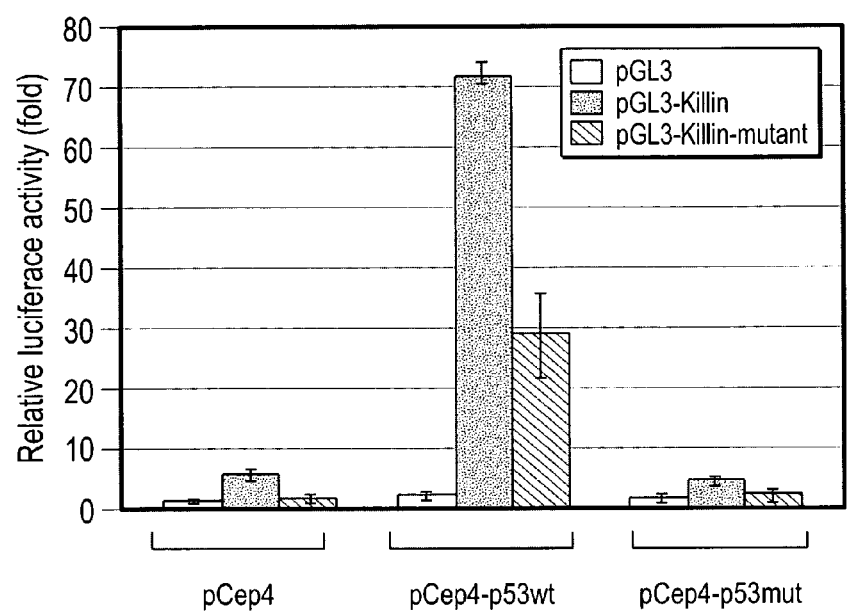

Killin is localized near the pTEN tumor-suppressor gene locus which contains a divergent promotor driving p53-dependent transcription of killin. DNA sequencing and genomic database search revealed that killin is localized in close proximity to the pten tumor-suppressor gene on human chromosome 10 (FIG. 2A). In fact, the intergenic region separating the two genes (based on transcriptional start sites) is only 194 bp in length that contains a divergent promoter with a highly consensus p53 binding site (FIG. 2A). Interestingly, pTEN was previously shown to be modulated by p53 as well, although, unlike killin, the basal level of PTEN expression appears to be constitutive (Stambolic et al., 2001). In order to determine if killin is a direct p53 target gene, a dual luciferase reporter assay was performed using the 140 bp intergenic region containing the conserved p53-binding site (FIG. 2B). The killin promoter conferred about 70-fold increase in wild-type p53-dependent luciferase activity, whereas an expression vector encoding a DNA-binding mutant p53 (R248W) failed to activate the promoter. Moreover, mutations within the conserved p53 binding site in the killin promoter great decreased the p53-dependent promoter strength (FIG. 2B). Taken together, these detailed promoter analysis confirms that killin is a direct transcriptional target of p53.

Figure 3A:
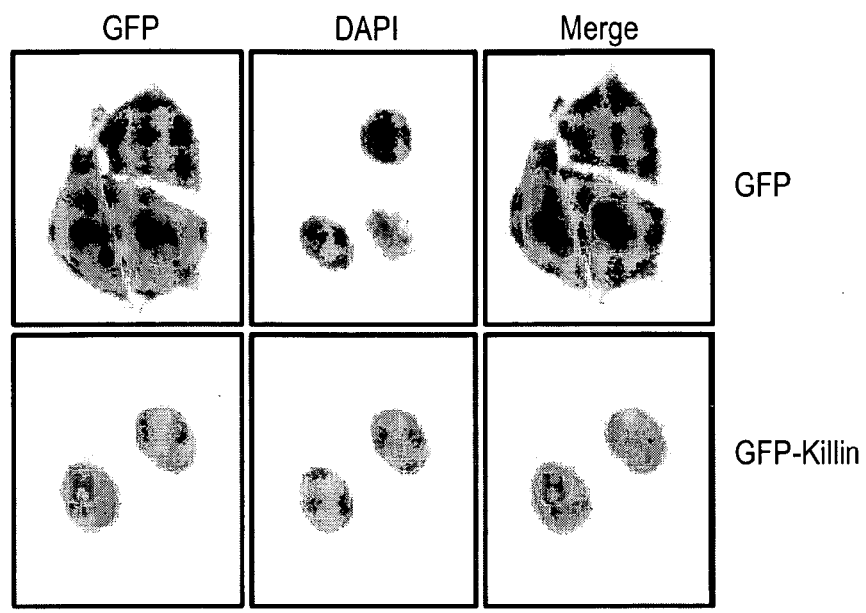
FIGS. 3A-C—Killin is a Nuclear Protein.
Figure 3B:
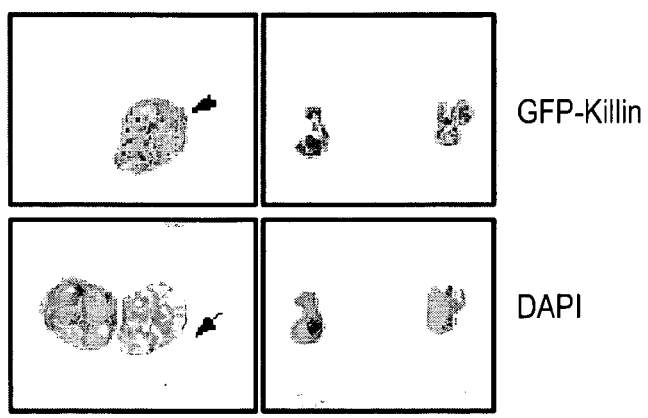
Figure 3C:
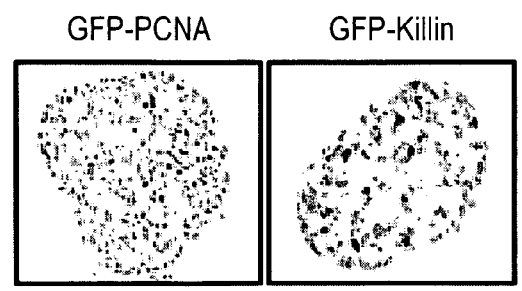

Killin is localized in the cell nucleus. To shed light on the biological function of Killin, the inventors first tried to determine its subcellular localization. Given its alkaline pI and the existence of two putative nuclear localization domains, the surmised that Killin might be a nuclear protein. To confirm this prediction, a GFP-Killin in-frame fusion protein was constructed. After stable transfection into the DLD-1 colon cancer cell line with a Tet repressor, the induction of either GFP alone or GFP-Killin within 16 hrs after removal of tetracycline was visualized under a fluorescence microscope. In contrast to GFP alone, which was expressed throughout the cells, GFP-Killin was exclusively nuclear in localization as shown by DAPI co-staining of the nuclei (FIG. 3A). To better visualize the sub-cellular distribution of Killin in the nucleus, which could provide clues to its biochemical functions, the inventors transiently transfected the GFP-Killin expression vector into Cos-1 cells, which were well attached and had large nuclei as depicted by DAPI staining (FIG. 3B). GFP-Killin was clearly localized in the nucleus of transfected cells and appeared to present as nuclear clusters or foci (FIG. 3B, upper left). Such focal distribution of GFP-Killin seemed to precede the nuclear condensation of apoptotic cells (FIG. 3B, upper right). Confocal fluorescent microscopy of Cos-1 cells expressing either GFP-PCNA or GFP-Killin provided a higher resolution of phase specific distribution of the corresponding proteins as nuclear foci (FIG. 3C). For GFP-PCNA, these foci are known to be clusters of replication forks along the chromatin where PCNA binds in S-phase nuclei (Leonhardt et al., 2000), whereas GFP-Killin foci exhibited a similar continuous cluster distribution pattern, except that the foci appeared more diffusive. These data suggest that Killin appears to be associated with chromatin.

Figure 4A:
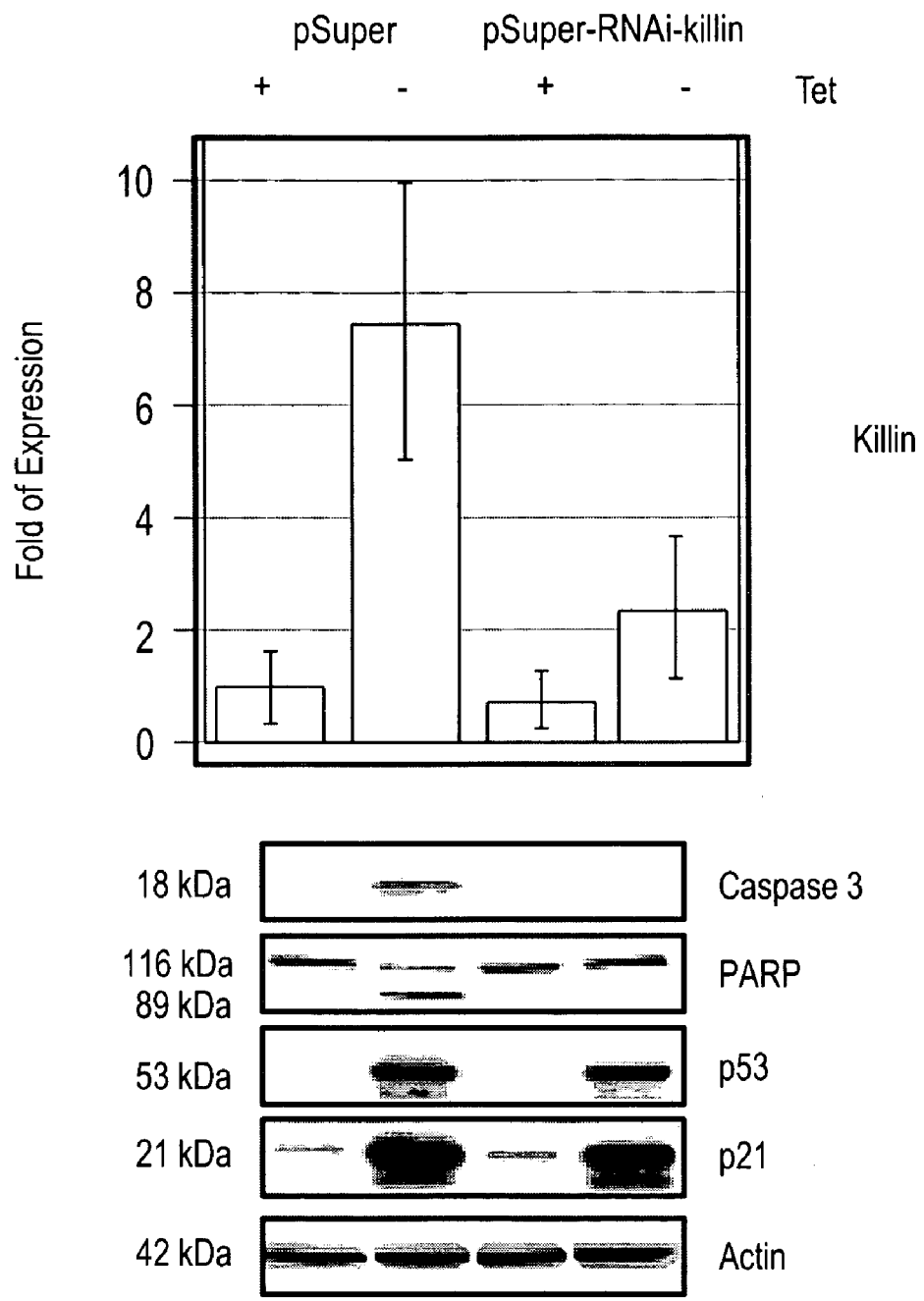
FIGS. 4A-B—Killin is Necessary for p53-mediated Apoptosis.
Figure 4B:
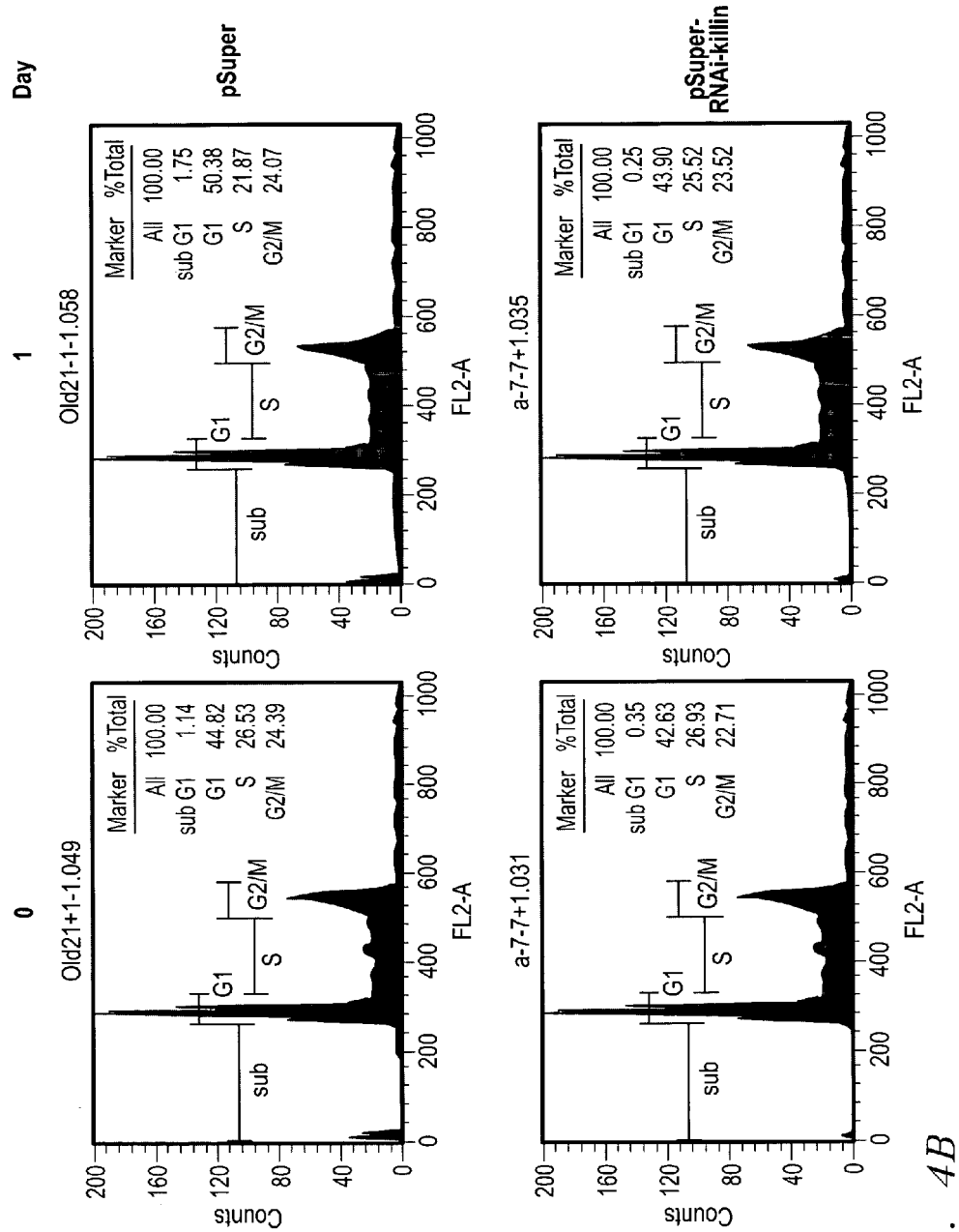
Figure 4C:
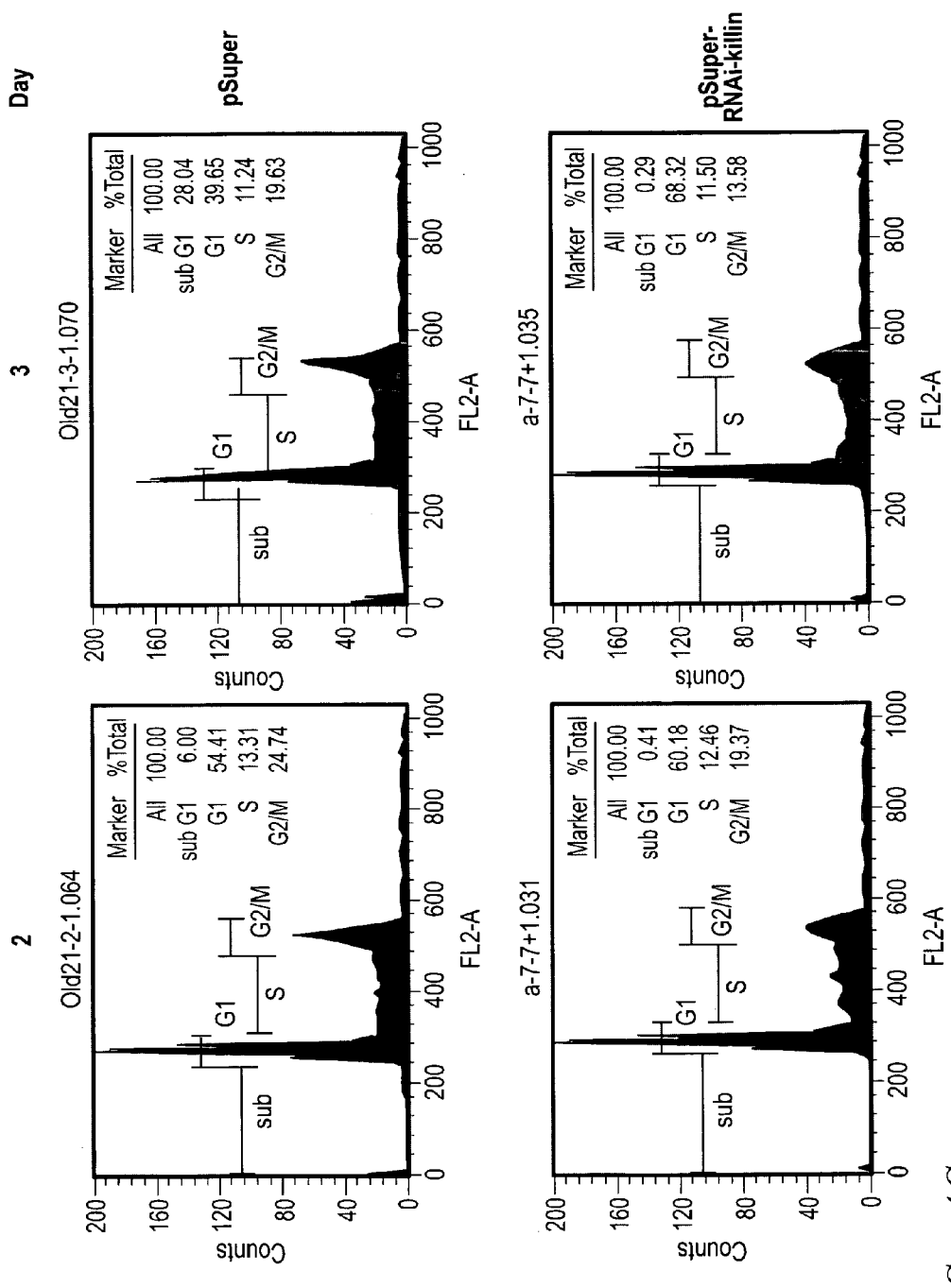
Figure 4D:
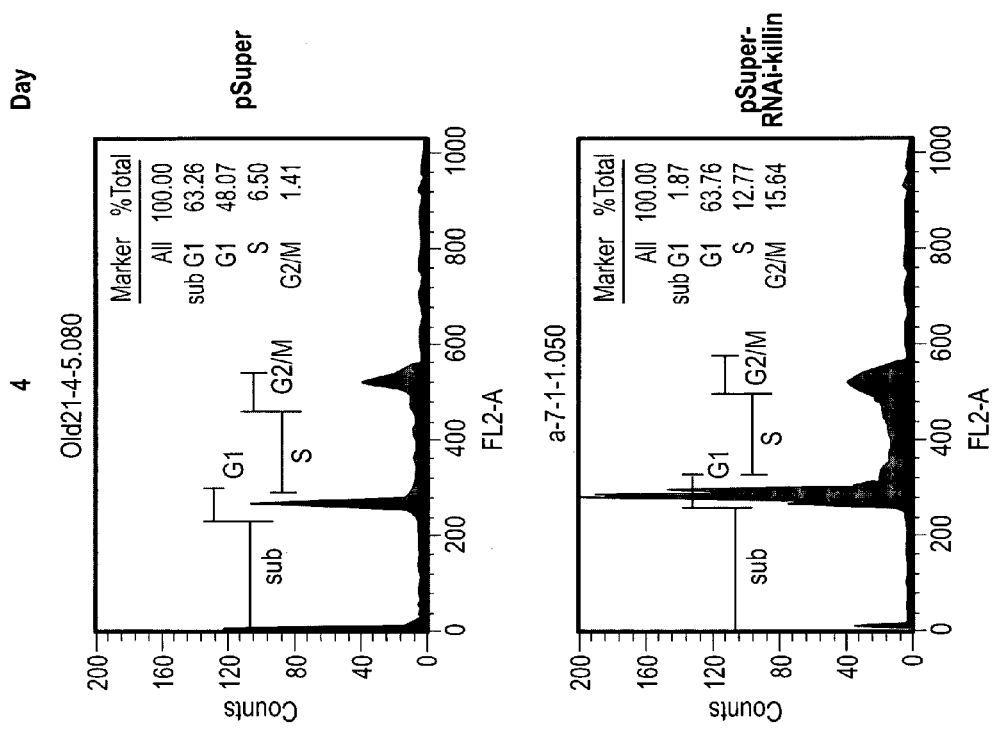

Killin is necessary for p53-mediated apoptosis. To determine if Killin is involved in any of the p53-mediated biological functions, the inventors employed RNAi technology to selectively knockdown the killin mRNA expression in H1299 cell line containing an inducible wild-type p53 gene, which was used for the initial FDD screening. Compared to cells stably transfected with the pSUPER RNAi vector control, cells stably transfected with pSUPER-RNAi-Killin showed not only a significantly decreased killin mRNA expression, but also marked blockade of p53-mediated apoptosis manifested by dramatic inhibition of both caspase-3 activation and caspase-dependent PARP cleavage, as well as by FACS analysis of the cell cycle profiles (FIGS. 4A-B). Moreover, blocking killin expression had little effect on p53 induced p21 expression (FIG. 4A), which led to mainly G1 arrest of the cells, as expected (FIG. 4B).

Figure 5A:
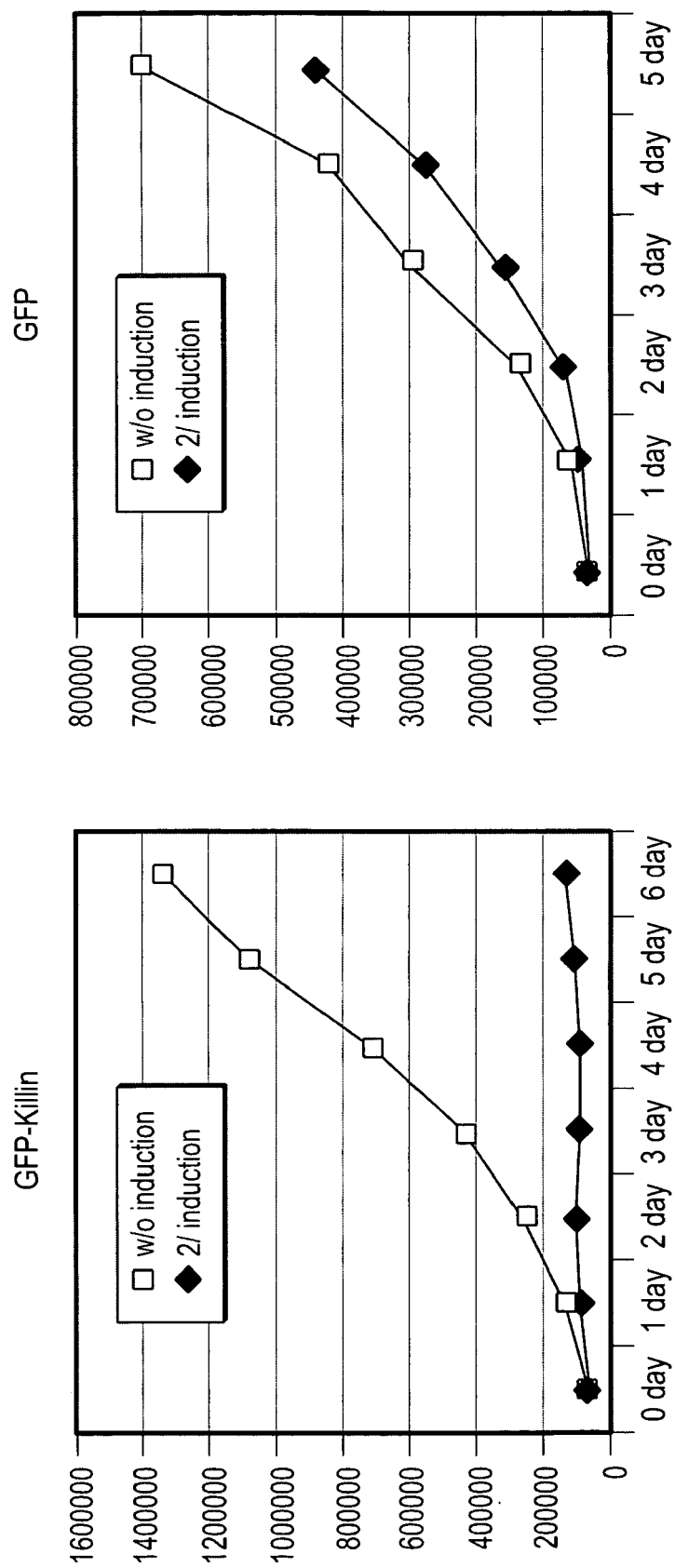
FIGS. 5A-C—Killin is Sufficient for Cell Apoptosis.
Figure 5B:
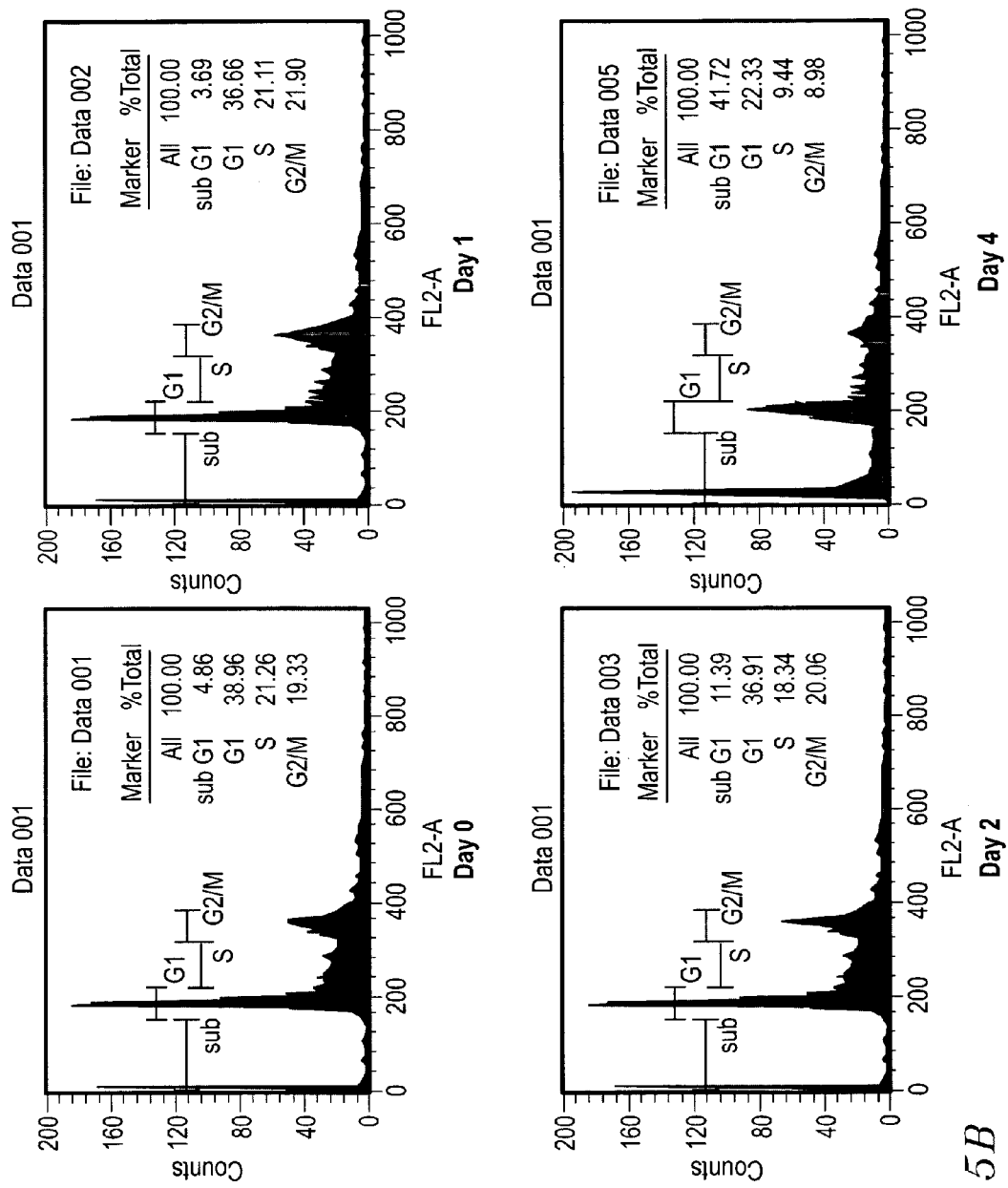
Figure 5C:
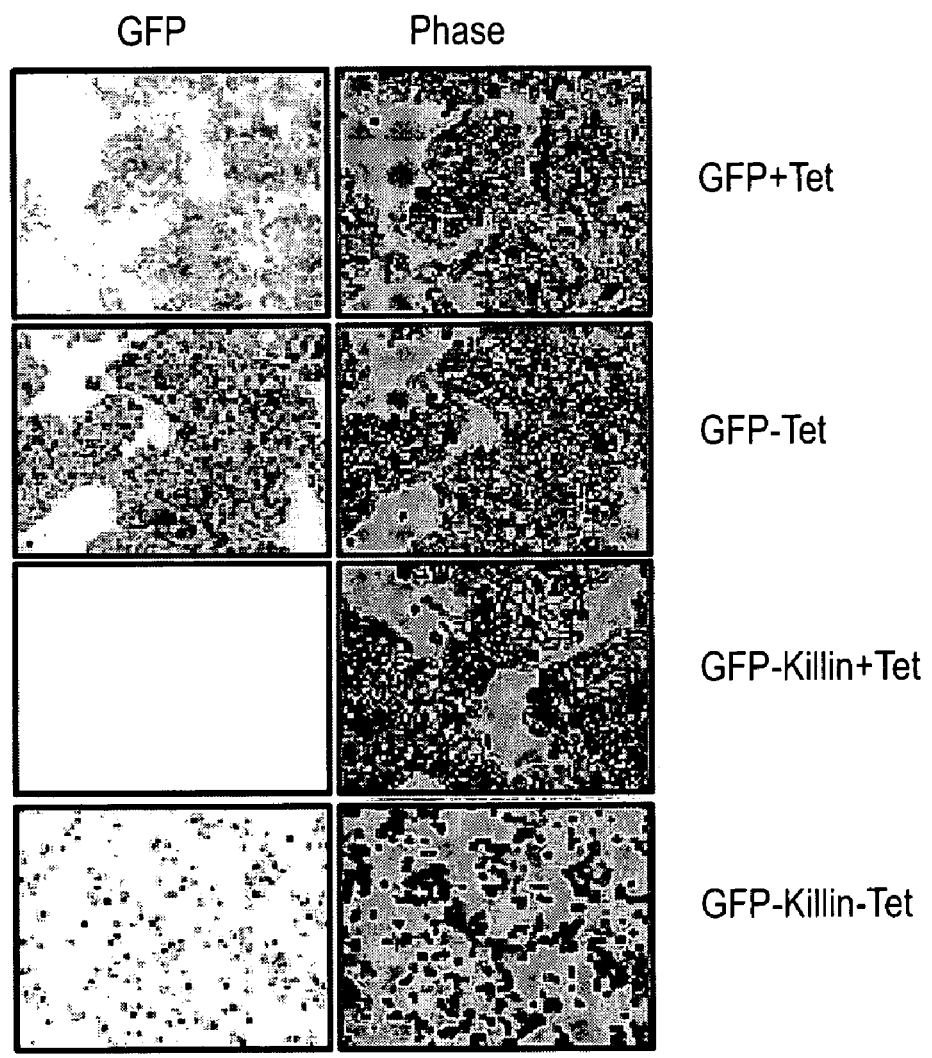

Killin is sufficient in inducing cell Growth arrest at S-phase followed by massive apoptosis. To determine if Killin is sufficient in triggering cell growth arrest and apoptosis, the inventors next analyzed the effect of inducible expression of GFP-Killin over time in DLD-1 colon cancer cells. Based on measurements of cell proliferation, fluorescent microscopy and FACS analysis, GFP-Killin was shown to cause rapid cell growth arrest within 24 hrs after tetracycline removal, whereas GFP alone had little effect (FIG. 5A). Interestingly, unlike p53-mediated growth arrest which occurs primarily at G1 via p21 (Chen et al., 1996), FACS analysis indicated that there was little decrease in S-phase DNA content nor increase in either G1 or G2 DNA content during the first 48 hrs of cell growth arrest following the induction of Killin (FIG. 5B). This rather surprising finding suggests that Killin may function as an inhibitor of DNA replication and causes S-phase arrest. However, massive apoptosis was observed by FACS analysis and fluorescence microscopy after 2-3 days following tetracycline removal and the induction of GFP-Killin (FIGS. 5B-C). This finding suggests that Killin induced growth arrest is coupled to cell death, in contrast to G1 arrest mediated by p21, which prevents cells from undergoing apoptosis.

Killin is a high affinity DNA binding protein. Based on Killin's nuclear localization, pattern of distribution and its potent effect on cell growth arrest at S-phase, the inventors hypothesized that Killin is a DNA binding protein. To further biochemically and functionally characterize Killin, four different experimental approaches were taken to verify this prediction. First, the inventors tried to bacterially express and purify a 6XHIS-tagged Killin. It turned out that the induction of the recombinant fusion protein by IPTG caused immediate growth arrest of the bacteria hosts within 30 min when the expressed protein could be barely detectable by Western blot analysis using HIS-tag monoclonal antibody. In addition to extremely low-level expression before cells stopped growing, bacterially expressed Killin appeared to adopt a unique conformation (e.g., association with other molecules such as DNA), which prevents it from being able to bind to Ni-NTA column, making its purification in native form literally impossible. The extremely toxic effect of low level Killin expression in bacteria appeared to concur with our prediction for it being a general DNA synthesis inhibitor, given the fact that bacteria have naked DNA. To overcome the difficulty in expression and purifying Killin protein, the full length Killin with predicted 20 kDa molecular weight was produced by in vitro transcription and translation, and shown to be able to bind to both single-stranded and double-stranded DNA templates (FIG. 6A). In contrast, a higher molecular weight non-specific protein encoded by the vector alone or the free labels failed to bind to the DNA cellulose beads, which served as negative controls for binding specificity (FIG. 6A).

Genetic and biochemical mapping of the DNA binding domain of killin. To further confirm and better define the functional domain of Killin for DNA binding, the inventors then turned to a genetic approach by taking advantage of the toxicity of Killin expression in *E. coli*. They hypothesized that the toxicity of Killin in mammalian cells and bacteria are functionally related and might have something to do with its ability to bind DNA and inhibit DNA replication. Thus, they first truncated the coding region of Killin into two parts at a unique Eco47III restriction site and showed that the N-terminal 123 amino acids were sufficient to retain toxicity to *E.* coli, whereas the plasmid expressing the C-terminal 124-178 amino acid residues was able to transform E. coli into colonies in the absence of transcriptional repression (FIG. 6B). To speed up the genetic screen for the functional domain of Killin, they then randomly mutagenized the plasmid encoding the full-length N-terminal HIS-tagged Killin using an alkylating agent, ethylmethanesulfonate (EMS). Compared to non-mutagenized vector, the mutagenesis allowed colony formation following transformation into a wild-type lac I host. DNA sequencing analysis revealed that the loss of function mutations of killin fell into 5 groups, and they were either premature nonsense mutations at codon 18, 24, 33 and 37 (FIG. 6B), or with a deletion of a tandem-repeat sequence within the promoter region of the pQE32 bacterial expression vector. The concentration of the loss of function mutations near the N-terminus of Killin suggested that its functional domain is smaller than initially anticipated. Further refined deletional mutagenesis was then conducted by PCR from both the N- and C-terminus of Killin and the results allowed the inventors to unambiguously pinpoint the minimal sequence from 8-49 amino acid residues, which were essential for Killin's toxicity in bacteria (FIG. 6B). It did not escape our notice that this region of Killin contained multiple WXXR or KXXW motifs and is rich in basic amino acids (FIG. 6C).

Figure 6D:
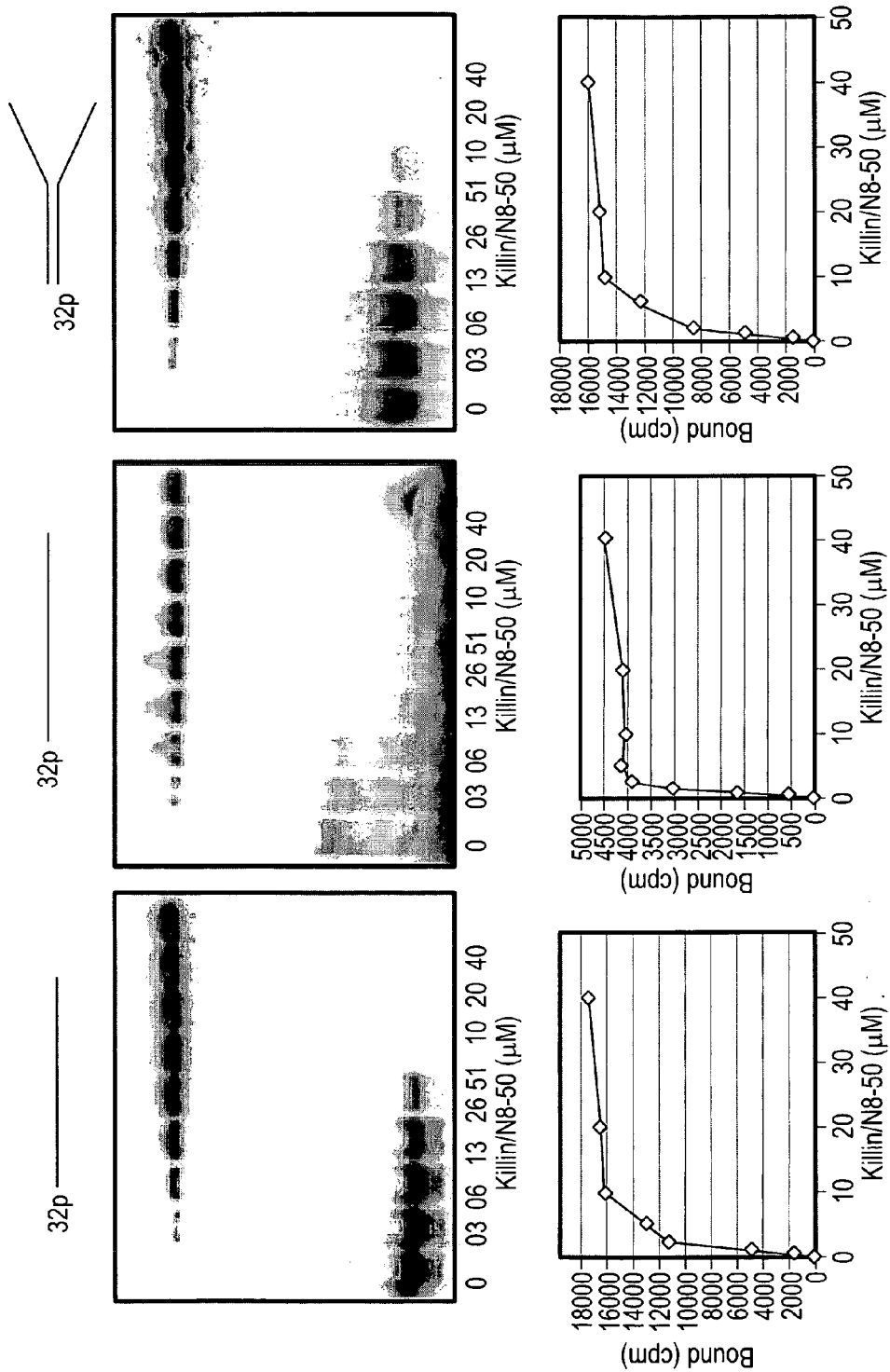

To overcome the difficulty in high-level expression of Killin due to its toxicity, the inventors chemically synthesized a peptide of 42 amino acid residues in length corresponding to N8-50 of Killin (FIG. 6C, here under designated as Killin/N8-50). In vitro kinetic binding studies using $^{32}$P-end labeled oligo nucleotide probes demonstrated that Killin/N8-50 peptide was able to bind to double-stranded DNA and an artificial replication fork with an apparent Kd of 1 μM, whereas the affinity to single-stranded DNA template appeared to be slightly higher with an apparent Kd being 0.5 μM (FIG. 6D). This important finding provides a biochemical basis for Killin function.

Figure 7A:
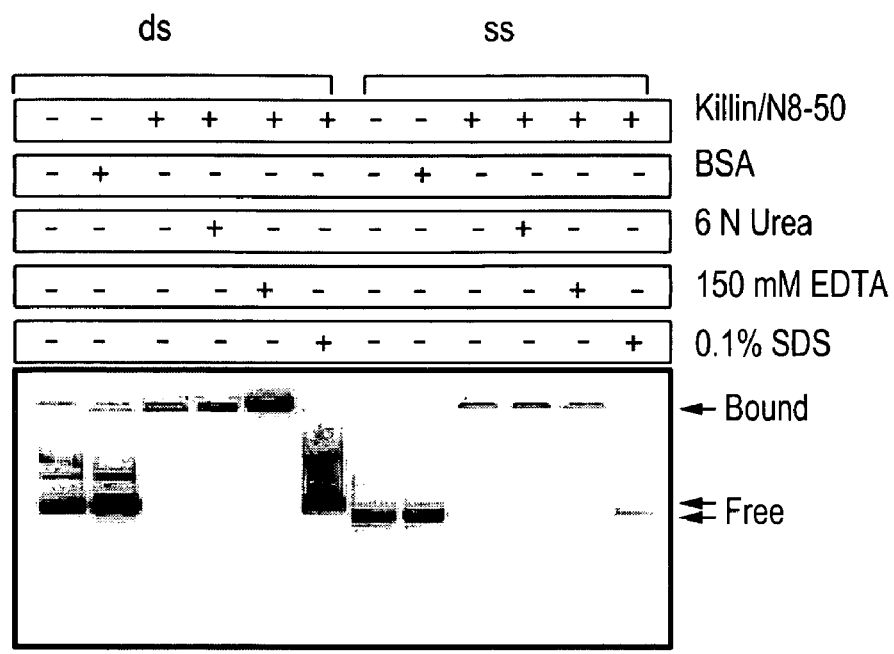
FIGS. 7A-B—Stability of Killin/N8-50-DNA Complex and Inhibition of in vitro DNA Replication by Killin/N8-50 Peptide.

Killin forms a highly stable non-covalently linked complex with DNA and inhibits DNA synthesis in vitro. Killin could bind not only to oligo nucleotide probes, but also much larger templates such as bacteria phage DNA and plasmids, which could be easily visualized by ethidium bromide staining (FIG. 7A). Complexes formed between Killin/N8-50 peptide and either the double-stranded or single-stranded bacteria phage PhiX174 DNA were so stable that it could withstand 6M urea and 150 mM EDTA, suggesting that neither hydrogen bonds nor divalent cations were involved in the interaction (FIG. 7A). However, SDS at a concentration as low as 0.1% could completely disrupt the Killin-DNA complex, indicating that Killin/N8-50 was neither a nuclease, nor the Killin-DNA complex was covalently bound.

Figure 7B:
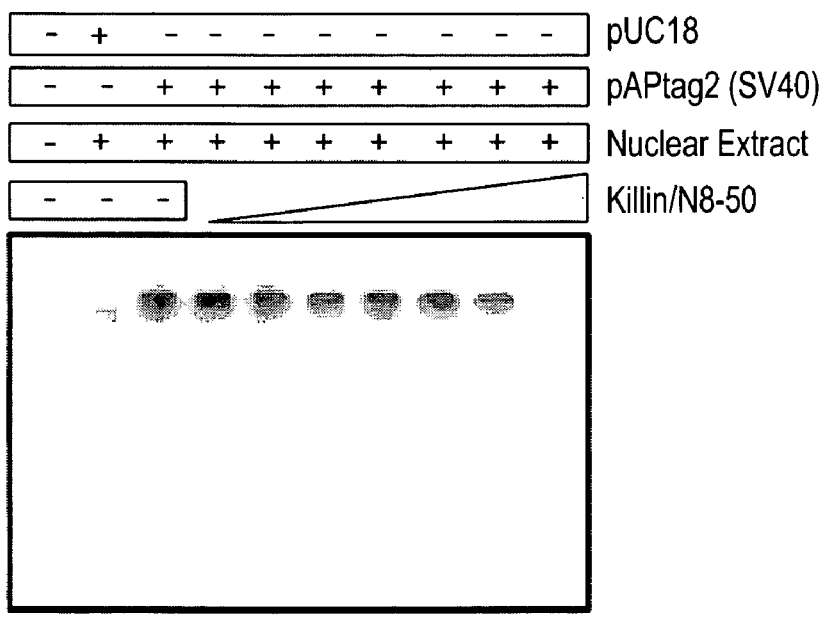

To determine if Killin/N8-50 peptide binding to DNA has any consequences in DNA replication, the inventors employed the commonly used in vitro eukayotic DNA replication assays originally described by Li and Kelly (1984). This assay uses soluble cell-free system derived from mammalian cell nuclear extract that is capable of replicating exogenous plasmid DNA molecules containing the simian virus 40 (SV40) origin of replication. Replication in the system is completely dependent upon the addition of the SV40 large T antigen. Using this assays, the inventors showed that the Killin/N8-50 peptide could greatly inhibit DNA replication (FIG. 7B). The requirement of higher concentration of Killin/N8-50 peptide for the inhibition of DNA replication than that seen in the in vitro DNA binding assays was most likely due to the high concentration of chromosomal DNA present in the nuclear extracts used as a source of SV40 large T antigen. Such chromosomal DNA would conceivably compete against plasmid template for Killin peptide binding, thus competitively inhibit the plasmid DNA replication. This prediction was consistent with results obtained by decreasing the amount nuclear extract used for the assay (data not shown).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

IX. REFERENCES

The following references, to the extent that they provide exemplary procedural or other details supplementary to those set forth herein, are specifically incorporated herein by reference:

U.S. Pat. No. 4,196,265
U.S. Pat. No. 4,554,101
U.S. Pat. No. 4,683,195
U.S. Pat. No. 4,683,202
U.S. Pat. No. 4,683,202
U.S. Pat. No. 4,684,611
U.S. Pat. No. 4,800,159
U.S. Pat. No. 4,873,191
U.S. Pat. No. 4,879,236
U.S. Pat. No. 4,883,750
U.S. Pat. No. 4,952,500
U.S. Pat. No. 5,217,879
U.S. Pat. No. 5,279,721
U.S. Pat. No. 5,302,523
U.S. Pat. No. 5,322,783
U.S. Pat. No. 5,354,855
U.S. Pat. No. 5,384,253
U.S. Pat. No. 5,384,253
U.S. Pat. No. 5,384,253
U.S. Pat. No. 5,464,765
U.S. Pat. No. 5,506,138
U.S. Pat. No. 5,506,138
U.S. Pat. No. 5,538,877
U.S. Pat. No. 5,538,880
U.S. Pat. No. 5,550,318
U.S. Pat. No. 5,563,055
U.S. Pat. No. 5,580,859
U.S. Pat. No. 5,589,466
U.S. Pat. No. 5,610,042
U.S. Pat. No. 5,656,610
U.S. Pat. No. 5,670,488
U.S. Pat. No. 5,670,488
U.S. Pat. No. 5,670,488
U.S. Pat. No. 5,702,932
U.S. Pat. No. 5,736,524
U.S. Pat. No. 5,739,018
U.S. Pat. No. 5,780,448
U.S. Pat. No. 5,789,215
U.S. Pat. No. 5,824,544

U.S. Pat. No. 5,824,544
U.S. Pat. No. 5,830,725
U.S. Pat. No. 5,849,304
U.S. Pat. No. 5,851,826
U.S. Pat. No. 5,858,744
U.S. Pat. No. 5,871,982
U.S. Pat. No. 5,871,983
U.S. Pat. No. 5,871,983
U.S. Pat. No. 5,871,986
U.S. Pat. No. 5,879,934
U.S. Pat. No. 5,888,502
U.S. Pat. No. 5,925,565
U.S. Pat. No. 5,928,906
U.S. Pat. No. 5,932,210
U.S. Pat. No. 5,932,210
U.S. Pat. No. 5,935,819
U.S. Pat. No. 5,945,100
U.S. Pat. No. 5,955,331
U.S. Pat. No. 5,955,331
U.S. Pat. No. 5,981,274
U.S. Pat. No. 5,994,136
U.S. Pat. No. 5,994,624
U.S. Pat. No. 6,013,516
EPO 0273085
EPO 329 822
GB Appn. 2 202 328
PCT Appln. PCT/US87/00880
PCT Appln. PCT/US89/01025
PCT Appln. WO 88/10315
PCT Appln. WO 89/06700
PCT Appln. WO 90/07641
PCT Appln. WO 9217598
PCT Appln. WO 94/09699
PCT Appln. WO 95/06128
Abraham, *Genes Dev.,* 15:2177-2196, 2001.
Almendro et al., *J. Immunol.,* 157 (12):5411-5421, 1996.
Amado and Chen, *Science,* 285 (5428):674-676, 1999.
Angel et al., *Cell,* 49:729, 1987b.
Angel et al., *Mol. Cell. Biol.,* 7:2256, 1987a.
Armentano et al., *Proc. Natl. Acad. Sci. USA,* 87(16):6141-6145, 1990.
Atchison and Perry, *Cell,* 46:253, 1986.
Atchison and Perry, *Cell,* 48:121, 1987.
Ausubel et al., In: *Current Protocols in Molecular Biology,* John, Wiley & Sons, Inc, New York, 1994.
Banerji et al., *Cell,* 27 (2 Pt 1):299-308, 1981.
Banerji et al., *Cell,* 33 (3):729-740, 1983.
Barany and Merrifield, In: *The Peptides,* Gross and Meienhofer (Eds.), Academic Press, NY, 1-284, 1979.
Bates, *Mol. Biotechnol.,* 2 (2):135-145, 1994.
Batra et al., *Am. J. Respir. Cell Mol. Biol.,* 21 (2):238-245, 1999.
Battraw and Hall, *Theor. App. Genet.,* 82 (2):161-168, 1991.
Bellus, *J. Macromol. Sci. Pure Appl. Chem.,* A31 (1): 1355-1376, 1994.
Berkhout et al., *Cell,* 59:273-282, 1989.
Bett et al., *J. Virololgy,* 67 (10):5911-5921, 1993.
Bhattacharjee et al., *J. Plant Bioch. Biotech.,* 6 (2):69-73, 1997.
Bilbao et al., *Transplant Proc.,* 31 (1-2):792-793, 1999.
Blackwell et al., *Arch. Otolaryngol. Head. Neck Surg.,* 125 (8):856-863, 1999.
Blanar et al, *EMBO J,* 8:1139, 1989.
Blomer et al., *J. Virol.,* 71 (9):6641-6649, 1997.
Bodine and Ley, *EMBO J,* 6:2997, 1987.
Boshart et al., *Cell,* 41:521, 1985.
Bosze et al., *EMBO J,* 5 (7):1615-1623, 1986.
Braddock et al., *Cell,* 58:269, 1989.
Brinster et al., *Proc. Natl. Acad. Sci. USA,* 82 (13):4438-4442, 1985. Levine, *Cell,* 88:323-331, 1997.
Bulla and Siddiqui, *J. Virol.,* 62:1437, 1986.
Campbell and Villarreal, *Mol. Cell. Biol.,* 8:1993, 1988.
Campbell et al., *Am. Rev. Respir. Dis.,* 130 (3):417-423, 1984.
Campere and Tilghman, *Genes and Dev.,* 3:537, 1989.
Campo et al., *Nature,* 303:77, 1983.
Capaldi et al., *Biochem. Biophys. Res. Comm.,* 76:425, 1977.
Caplen et al., *Gene Ther.,* 6 (3):454-459, 1999.
Carbonelli et al., *"FEMS Microbiol Lett.* 177 (1):75-82, 1999.
Case et al., *Proc. Natl. Acad. Sci. USA,* 96 (6):2988-2893, 1999.
Celander and Haseltine, *J. Virology,* 61:269, 1987.
Celander et al., *J. Virology,* 62:1314, 1988.
Chandler et al., *Cell,* 33:489, 1983.
Chandler et al., *Proc. Natl. Acad. Sci. USA,* 94 (8):3596-601, 1997.
Chang et al., *Mol. Cell. Biol.,* 9:2153, 1989.
Chatterjee et al., *Proc. Natl. Acad. Sci. USA,* 86:9114, 1989.
Chen and Okayama, *Mol. Cell. Biol.* 7:2745-2752, 1987.
Chen et al., *Genes Dev.,* 10:2438-2451, 1996.
Chillon et al., *J. Virol.,* 73 (3):2537-2540, 1999.
Cho et al., *Biotechniques,* 30:562-572, 2001.
Choi et al., *Cell,* 53:519, 1988.
Christou et al., *Proc. Natl. Acad. Sci. USA,* 84 (12):3962-3966, 1987.
Clay et al., *Pathol. Oncol. Res.,* 5 (1):3-15, 1999.
Cocea, *Biotechniques,* 23 (5): 814-816, 1997.
Coffey et al., *Science,* 282 (5392):1332-1334, 1999.
Cohen et al., *J. Cell. Physiol.,* 5:75, 1987.
Cook et al., *Cell,* 27:487-496, 1981.
Costa et al., *Mol. Cell. Biol.,* 8:81, 1988.
Cripe et al, *EMBO J,* 6:3745, 1987.
Culotta and Hamer, *Mol. Cell. Biol.,* 9:1376, 1989.
Culver et al., *Science,* 256 (5063):1550-1552, 1992.
Dandolo et al., *J. Virology,* 47:55-64, 1983.
De Villiers et al., *Nature,* 312(5991):242-246, 1984.
DeLuca et al., *J. Virol.,* 56 (2):558-570, 1985.
Deng et al., *Cell,* 82:675-684, 1995.
Derby et al., *Hear Res.,* 134 (1-2):1-8, 1999.
Deschamps et al., *Science,* 230:1174-1177, 1985.
D'Halluin et al., *Plant Cell,* 4 (12):1495-1505, 1992.
Dorai et al., *Int. J. Cancer,* 82 (6):846-852, 1999.
Edbrooke et al., *Mol. Cell. Biol.,* 9:1908, 1989.
Edlund et al., *Science,* 230:912-916, 1985.
El-Deiry, *Semin. Cancer Biol.* 8:345-357, 1998.
Engel and Kohn, *Front Biosci.,* 4:e26-33, 1999.
Falck et al., *Nature,* 434:605-611, 2005.
Fechheimer, et al., *Proc Natl. Acad. Sci. USA,* 84:8463-8467, 1987.
Feldman et al., *Semin. Interv. Cardiol.,* 1 (3):203-208, 1996.
Feng and Holland, *Nature,* 334:6178, 1988.
Feng et al., *Nat. Biotechnol.,* 15 (9):866-870, 1997.
Firak and Subramanian, *Mol. Cell. Biol.,* 6:3667, 1986.
Fisher et al., *Virology,* 217 (1):11-22, 1996.
Foder et al., *Science,* 251:767-773, 1991.
Foecking and Hofstetter, *Gene,* 45 (1):101-105, 1986.
Forster and Symons, *Cell,* 49:211-220, 1987.
Fraley et al., *Proc. Natl. Acad. Sci. USA,* 76:3348-3352, 1979.
Freifelder, In: *Physical Biochemistry Applications to Biochemistry and Molecular Biology,* 2nd Ed. Wm. Freeman and Co., NY, 1982.
Frohman, In: *PCR Protocols: A Guide To Methods And Applications,* Academic Press, N.Y., 1990.
Fujita et al., *Cell,* 49:357, 1987.

Fujiwara and Tanaka, *Nippon Geka Gakkai Zasshi,* 99 (7): 463-468, 1998.
Garoff and Li, *Curr. Opin. Biotechnol.,* 9 (5):464-469, 1998.
Garrido et al., *J. Neurovirol.,* 5 (3):280-288, 1999.
Gefter et al., *Somatic Cell Genet.,* 3:231-236, 1977.
Gerlach et al., *Nature* (London), 328:802-805, 1987.
Ghosh and Bachhawat, In: *Liver Diseases, Targeted Diagnosis and Therapy Using Specific Receptors and Ligands,* Wu and Wu (Eds.), Marcel Dekker, New York, 87-104, 1991.
Gilles et al., *Cell,* 33:717, 1983.
Gloss et al., *EMBO J.,* 6:3735, 1987.
Gnant et al., *Cancer Res.,* 59 (14):3396-403, 1999.
Gnant et al., *J. Natl. Cancer Inst.,* 91 (20):1744-1750, 1999.
Godbout et al., *Mol. Cell. Biol.,* 8:1169, 1988.
Goding, In: *Monoclonal Antibodies: Principles and Practice,* 2d ed., Orlando, Fla., Academic Press, 60-61, 65-66, 71-74, 1986.
Goodbourn and Maniatis, *Proc. Natl. Acad. Sci. USA,* 85:1447, 1988.
Goodbourn et al., *Cell,* 45:601, 1986.
Gopal, *Mol. Cell. Biol.,* 5:1188-1190, 1985.
Gottifredi and Prives, *Semin. Cell Dev. Biol.,* 16:355-368, 2005.
Graham and Prevec *Mol. Biotechnol.,* 3 (3):207-220, 1995.
Graham and Van Der Eb, *Virology* 52:456-467, 1973
Greene et al., *Immunology Today,* 10:272, 1989
Grosschedl and Baltimore, *Cell,* 41:885, 1985.
Hacia et al., *Nature Genet.,* 14:441-449, 1996.
Haecker et al., *Hum. Gene Ther.,* 7 (15):1907-1914, 1996.
Han et al., *Euro. J. Surgical Oncology,* 25:194-198, 1999.
Harland and Weintraub, *J. Cell Biol.,* 101:1094-1099, 1985.
Harlow and Lane, In: *Antibodies: A laboratory Manual,* Cold Spring Harbor Laboratories, Cold Spring Harbor, N.Y., 1988.
Haslinger and Karin, *Proc. Natl. Acad. Sci. USA,* 82:8572, 1985.
Hauber and Cullen, *J. Virology,* 62:673, 1988.
Hayashi et al., *Neurosci. Lett.,* 267 (1):37-40, 1999.
He et al., *Plant Cell Reports,* 14 (2-3):192-196, 1994.
Hen et al., *Nature,* 321:249, 1986.
Hensel et al., *Lymphokine Res.,* 8:347, 1989.
Hermens and Verhaagen, *Prog. Neurobiol.,* 55 (4):399-432, 1998.
Herr and Clarke, *Cell,* 45:461, 1986.
Hirochika et al., *J. Virol.,* 61:2599, 1987.
Hirsch et al., *Mol. Cell. Biol.,* 10:1959, 1990.
Hogan et al., In: *Manipulating the Mouse Embryo: A Laboratory Manual,* 2nd ed., Cold Spring Harbor Laboratory Press, 1994.
Holbrook et al., *Virology,* 157:211, 1987.
Holzer et al., *Virology,* 253 (1):107-114, 1999.
Horlick and Benfield, *Mol. Cell. Biol.,* 9:2396, 1989.
Hou and Lin, *Plant Physiology,* 111: 166, 1996.
Howard et al., *Ann. NY Acad. Sci.,* 880:352-365, 1999.
Huang et al., *Cell,* 27:245, 1981.
Huard et al., *Neuromuscul Disord.,* 7 (5):299-313, 1997.
Hug et al., *Mol. Cell. Biol.,* 8:3065, 1988.
Hwang et al., *Mol. Cell. Biol.,* 10:585, 1990.
Imagawa et al., *Cell,* 51:251, 1987.
Imai et al., *J. Virol.,* 72 (5):4371-4378, 1998.
Imbra and Karin, *Nature,* 323:555, 1986.
Imler et al., *Mol. Cell. Biol.,* 7:2558, 1987.
Imperiale and Nevins, *Mol. Cell. Biol.,* 4:875, 1984.
Innis et al., *Proc Natl Acad Sci USA,* 85 (24):9436-9440, 1988.
Irie et al., *Antisense Nucleic Acid Drug Dev.,* 9 (4):341-349, 1999.
Jakobovits et al., *Mol. Cell. Biol.,* 8:2555, 1988.
Jameel and Siddiqui, *Mol. Cell. Biol.,* 6:710, 1986.
Jaynes et al., *Mol. Cell. Biol.,* 8:62, 1988.
Johnson et al., *IN: Biotechnology And Pharmacy,* Pezzuto et al., (Eds.), Chapman and Hall, New York, 1993.
Johnson et al., *Mol. Cell. Biol.,* 9:3393, 1989.
Johnston et al., *J. Virol.,* 73 (6):4991-5000, 1999.
Joyce, *Nature,* 338:217-244, 1989.
Kadesch and Berg, *Mol. Cell. Biol.,* 6:2593, 1986.
Kaeppler et al., *Plant Cell Reports,* 9:415-418, 1990.
Kaneda et al., *Science,* 243:375-378, 1989.
Karin et al., *Mol. Cell. Biol.,* 7:606, 1987.
Katinka et al., *Cell,* 20:393, 1980.
Kato et al., *J. Biol. Chem.,* 266 (6):3361-3364, 1991.
Kaufman et al., *Surv. Ophthalmol.,* 43 Suppl 1:S91-97, 1999.
Kawamoto et al., *Mol. Cell. Biol.,* 8:267, 1988.
Kay, *Haemophilia,* 4 (4):389-392, 1998.
Kiledjian et al., *Mol. Cell. Biol.,* 8:145, 1988.
Kim and Cech, *Proc. Natl. Acad. Sci. USA,* 84:8788-8792, 1987.
Klamut et al., *Mol. Cell. Biol.,* 10:193, 1990.
Klimatcheva et al., *Front Biosci.,;* 4:D481-96, 1999.
Koch et al., *Mol. Cell. Biol.,* 9:303, 1989.
Kohler and Milstein, *Eur. J. Immunol.,* 6:511-519, 1976.
Kohler and Milstein, *Nature,* 256:495-497, 1975.
Kohut et al., *Am. J. Physiol.,* 275 (6 Pt 1):L1089-94, 1998.
Kooby et al., *FASEB J.,* 13 (11):1325-1334, 1999.
Kornberg, In: *DNA Replication,* W. H. Freeman and Company, New York, 1992.
Kraus et al., *FEBS Lett.,* 428 (3):165-170, 1998.
Kriegler and Botchan, In: *Eukaryotic Viral Vectors,* Gluzman (Ed.), Cold Spring Harbor: Cold Spring Harbor Laboratory, NY, 1982.
Kriegler and Botchan, *Mol. Cell. Biol.,* 3:325, 1983.
Kriegler et al., *Cell,* 38:483, 1984.
Kriegler et al, *Cell,* 53:45, 1988.
Krisky et al., *Gene Ther.,* 5 (11):1517-1530, 1998.
Krisky et al., *Gene Ther.,* 5 (12):1593-1603, 1998.
Kuhl et al., *Cell,* 50:1057, 1987.
Kunz et al., *Nucl. Acids Res.,* 17:1121, 1989.
Kwoh et al., *Proc. Natl. Acad. Sci. USA,* 86 (4):1173-1177, 1989.
Kyte and Doolittle, *J. Mol. Biol.,* 157 (1):105-132, 1982.
Lachmann and Efstathiou, *Clin. Sci. (Colch),* 96 (6):533-541, 1999.
Lareyre et al., *J. Biol. Chem.,* 274 (12):8282-8290, 1999.
Larsen et al., *Proc Natl. Acad. Sci. USA.,* 83:8283, 1986.
Laspia et al., *Cell,* 59:283, 1989.
Latimer et al., *Mol. Cell. Biol.,* 10: 760, 1990.
Lazzeri, *Methods Mol. Biol.,* 49:95-106, 1995.
Lee et al., *Korean J. Genet.,* 11 (2):65-72, 1989.
Lee et al., *J. Auton. Nerv. Syst.,* 74 (2-3):86-90, 1997.
Lee et al., *Nature,* 294:228, 1981.
Lee et al., *Nature,* 329 (6140):642-645, 1987.
Lee et al., *Nucleic Acids Res.,* 12:4191-206, 1984.
Leibowitz et al., *Diabetes,* 48 (4):745-753, 1999.
Leonhardt et al., *J. Cell Biol.,* 149:271-280, 2000.
Lesch, *Biol. Psychiatry,* 45 (3):247-253, 1999.
Levenson et al., *Human Gene Therapy,* 9:1233-1236, 1998.
Levinson et al., *Nature,* 295:79, 1982.
Li et al., *Science,* 275:1943-1947, 1997.
Liang and Pardee, *Nature Reviews Cancer,* 3:869-876, 2003.
Liang, *Biotechniques,* 33:338-346, 2002.
Lin et al., *Mol. Cell. Biol.,* 10:850, 1990.
Lundstrom, *J. Recept. Signal Transduct. Res.,* 19 (1-4):673-686, 1999.
Luria et al., *EMBO J.,* 6:3307, 1987.

Lusky and Botchan, *Proc. Natl. Acad. Sci. USA*, 83:3609, 1986.
Lusky et al., *Mol. Cell. Biol.*, 3:1108, 1983.
Macejak and Sarnow, *Nature*, 353:90-94, 1991.
Majors and Varmus, *Proc. Natl. Acad. Sci. USA*, 80:5866, 1983.
Marienfeld et al., *Gene Ther.*, 6 (6):1101-1113, 1999.
Mastrangelo et al., *Cancer Gene Ther.*, 6 (5):409-422 1999.
McNeall et al., *Gene*, 76:81, 1989.
Merrifield, *Science*, 232 (4748):341-347 1986.
Michel and Westhof, *J. Mol. Biol.*, 216:585-610, 1990.
Miksicek et al., *Cell*, 46:203, 1986.
Miller et al., *Methods Enzymol.*, 217:581-599, 1993.
Miyatake et al., *Gene Ther.*, 6 (4):564-572, 1999.
Moldawer et al., *Shock*, 12 (2):83-101, 1999.
Mordacq and Linzer, *Genes and Dev.*, 3:760, 1989.
Moreau et al., *Nuc. Acids Res.*, 9:6047, 1981.
Moriuchi et al., *Cancer Res.*, 58 (24):5731-5737, 1998.
Morrison et al., *J. Gen. Virol.*, 78 (Pt 4):873-878, 1997.
Muesing et al., *Cell*, 48:691, 1987.
Nahle et al., *Nat. Cell Biol.*, 4:859-864, 2002.
Naldini et al., *Proc. Natl. Acad. Sci. USA*, 93 (21):11382-11388, 1996.
Ng et al., *Nuc. Acids Res.*, 17:601, 1989.
Nicolau and Sene, *Biochim. Biophys. Acta*, 721:185-190, 1982.
Nicolau et al., *Methods Enzymol.*, 149:157-176, 1987
Nomoto et al., *Gene*, 236 (2):259-271, 1999.
Ohara et al., *Proc. Natl. Acad. Sci. USA*, 86:5673-5677, 1989.
Omirulleh et al., *Plant Mol. Biol.*, 21 (3):415-28, 1993.
Ondek et al., *EMBO J.*, 6:1017, 1987.
Omitz et al., *Mol. Cell. Biol.*, 7:3466, 1987.
Palmiter et al., *Nature*, 300:611, 1982.
Parks et al., *J. Virol.*, 71 (4):3293-8, 1997.
Pease et al., *Proc. Natl. Acad. Sci. USA*, 91:5022-5026, 1994.
Pech et al., *Mol. Cell. Biol.*, 9:396, 1989.
Pelletier and Sonenberg, *Nature*, 334:320-325, 1988.
Perales et al., *Proc. Natl. Acad. Sci. USA*, 91:4086-4090, 1994.
Perez-Stable and Constantini, *Mol. Cell. Biol.*, 10:1116, 1990.
Petrof, *Eur. Respir. J*, 11 (2):492-497, 1998.
Picard and Schaffner, *Nature*, 307:83, 1984.
Pignon J et al., *Hum. Mutat.*, 3 (2): 126-132, 1994.
Pinkert et al., *Genes and Dev.*, 1:268, 1987.
Polyak et al., *Genes Dev.*, 10: 1945-1952, 1996.
Ponta et al., *Proc. Natl. Acad. Sci. USA*, 82:1020, 1985.
Porton et al., *Mol. Cell. Biol.*, 10:1076, 1990.
Potrykus et al., *Mol. Gen. Genet.*, 199:183-188, 1985.
Potter et al., *Proc. Natl. Acad. Sci. USA*, 81:7161-7165, 1984.
Queen and Baltimore, *Cell*, 35:741, 1983.
Quinn et al., *Mol. Cell. Biol.*, 9:4713, 1989.
Rabinovitch et al., *Diabetes*, 48 (6):1223-1229, 1999.
Reddy et al., *J. Virol.*, 72 (2):1394-1402, 1998.
Redondo et al., *Science*, 247:1225, 1990.
Reinhold-Hurek and Shub, *Nature*, 357:173-176, 1992.
Reisman and Rotter, *Mol. Cell. Biol.*, 9:3571, 1989.
Remington's Pharmaceutical Sciences, 15th ed., pages 1035-1038 and 1570-1580, Mack Publishing Company, Easton, Pa., 1980.
Remington's Pharmaceutical Sciences 15th Edition, 33:624-652, 1990
Resendez Jr. et al., *Mol. Cell. Biol.*, 8:4579, 1988.
Rhodes et al., *Methods Mol. Biol.*, 55:121-131, 1995.
Ripe et al., *Mol. Cell. Biol.*, 9:2224, 1989.
Rippe et al., "DNA-mediated gene transfer into adult rat hepatocytes in primary culture," *Mol. Cell Biol.*, 10:689-695, 1990.
Rittling et al., *Nuc. Acids Res.*, 17:1619, 1989.
Robbins and Ghivizzani, *Pharmacol. Ther.*, 80 (1):35-47, 1998.
Robbins et al., *Proc. Natl. Acad. Sci. USA*, 95 (17):10182-10187 1998.
Robbins et al., *Trends Biotechnol.*, 16 (1):35-40, 1998.
Rosen et al., *Cell*, 41:813, 1988.
Sakai et al., *Genes and Dev.*, 2:1144, 1988.
Sambrook et al., In: *Molecular Cloning: A Laboratory Manual*, Vol. 1, Cold Spring Harbor Laboratory Press, Cold Spring Harbor, N.Y., Ch. 7,7, 19-17.29, 1989.
Sarver et al., *Science*, 247:1222-1225, 1990.
Satake et al., *J. Virology*, 62:970, 1988.
Sawai et al., *Mol. Genet. Metab.*, 67 (1):36-42, 1999.
Scanlon et al., *Proc. Natl. Acad. Sci. USA*, 88:10591-10595, 1991.
Schaffner et al., *J. Mol. Biol.*, 201:81, 1988.
Searle et al., *Mol. Cell. Biol.*, 5:1480, 1985.
Sharp and Marciniak, *Cell*, 59:229, 1989.
Shaul and Ben-Levy, *EMBO J*, 6:1913, 1987.
Sherman et al., *Mol. Cell. Biol.*, 9:50, 1989.
Shoemaker et al., *Nature Genetics*, 14:450-456, 1996.
Sleigh and Lockett, *J. EMBO*, 4:3831, 1985.
Smith, *Arch. Neurol.*, 55 (8):1061-1064, 1998.
Spalholz et al., *Cell*, 42:183, 1985.
Spandau and Lee, *J. Virology*, 62:427, 1988.
Spandidos and Wilkie, *EMBO J.*, 2:1193, 1983.
Stambolic et al., *Mol. Cell*, 8:317-325, 2001.
Steck et al., *Nat. Genet.*, 15:356-362, 1997.
Stein et al., *J. Biol. Chem.*, 279:48930-48940, 2004.
Stephens and Hentschel, *Biochem. J.*, 248:1, 1987.
Stewart and Young, "Solid Phase Peptide Synthesis", 2d. ed., Pierce Chemical Co., 1984.
Stewart et al., *Gene Ther.*, 6 (3):350-363, 1999.
Stuart et al., *Nature*, 317:828, 1985.
Sullivan and Peterlin, *Mol. Cell. Biol.*, 7:3315, 1987.
Suzuki et al., *Biochem. Biophys. Res. Commun.*, 252 (3):686-690, 1998.
Swartzendruber and Lehman, *J. Cell. Physiology*, 85:179, 1975.
Takebe et al., *Mol. Cell. Biol.*, 8:466, 1988.
Tam et al., *J. Am. Chem. Soc.*, 105:6442, 1983.
Tanaka et al., *Oncogene*, 8:2253-2258, 1993.
Taniura et al., *J. Biol. Chem.*, 274:16242-16248, 1999.
Tavernier et al., *Nature*, 301:634, 1983.
Taylor and Kingston, *Mol. Cell. Biol.*, 10:165, 1990a.
Taylor and Kingston, *Mol. Cell. Biol.*, 10:176, 1990b.
Taylor and Stark, *Oncogene*, 20:1803-1815, 2001.
Taylor et al., *J. Biol. Chem.*, 264:15160, 1989.
Thiesen et al., *J. Virology*, 62:614, 1988.
Timiryasova et al., *Int. J. Oncol.*, 14 (5):845-854, 1999.
Timiryasova et al., *Oncol. Res.*; 11 (3):133-144, 1999.
Treisman, *Cell*, 42:889, 1985.
Tronche et al., *Mol. Biol. Med.*, 7:173, 1990.
Trudel and Constantini, *Genes and Dev.*, 6:954, 1987.
Tsukada et al., *Plant Cell Physiol.*, 30 (4) 599-604, 1989.
Tsumaki et al., *J. Biol. Chem.*, 273 (36):22861-22864, 1998.
Tur-Kaspa et al., *Mol. Cell. Biol.*, 6:716-718, 1986.
Tyndell et al., *Nuc. Acids. Res.*, 9:6231, 1981.
Vanderkwaak et al., *Gynecol. Oncol.*, 74 (2):227-234, 1999.
Vannice and Levinson, *J. Virology*, 62:1305, 1988.
Vasseur et al., *Proc Natl. Acad. Sci. USA*, 77:1068, 1980.
Vogelstein et al., *Nature*, 408 (6810):307-310, 2000.
Vogelstein, *Nature*, 348(6303):681-682, 1990.

Vousden and Lu, *Nat. Rev. Cancer,* 2:594-604, 2002.
Vousden and Prives, *Cell,* 120:7-10, 2005.
Wagner et al., *Science,* 260:1510-1513, 1990.
Walker et al., *Nucleic Acids Res.,* 20 (7):1691-1696, 1992.
Wang and Calame, *Cell,* 47:241, 1986.
Wang et al., *Gynecol. Oncol.,* 71 (2):278-287, 1998.
Weber et al., *Cell,* 36:983, 1984.
Weihl et al., *Neurosurgery,* 44 (2):239-252, 1999.
Weinberg et al., *Biochemistry,* 28:8263-8269, 1989.
Weinberger et al., *Mol. Cell. Biol.,* 8:988, 1984.
White et al., *J. Virol.,* 73 (4):2832-28340, 1999.
Wilson, *J. Clin. Invest.,* 98 (11):2435, 1996.
Winoto and Baltimore, *Cell,* 59:649, 1989.
Wong et al., *Gene,* 10:87-94, 1980.
Wu and Wallace, *Genomics,* 4:560-569, 1989.
Wu and Wu, *J. Biol. Chem.,* 262:4429-4432, 1987.
Wu et al., *Biochem. Biophys. Res. Commun.,* 233 (1):221-226, 1997.
Wu, Chung *Hua Min Kuo Hsiao Erh Ko I Hsueh Hui Tsa Chih,* 39 (5):297-300, 1998.
Yamada et al., *Proc. Natl. Acad. Sci. USA,* 96 (7):4078-4083, 1999.
Yang and Liang, *Mol Biotechnol.,* 3:197-208, 2004.
Yeung et al., *Gene Ther.,* 6 (9):1536-1544, 1999.
Yoon et al., *J. Gastrointest. Surg.,* 3 (1):34-48, 1999.
Yu and Zhang, *Biochem. Biophys. Res. Commun.,* 331:851-858, 2005.
Yu et al., *Proc. Natl. Acad. Sci. USA,* 100:1931-1936, 2003.
Yu et al., *Proc. Natl. Acad. Sci. USA,* 96:14517-14522, 1999.
Yutzey et al., *Mol. Cell. Biol.,* 9:1397, 1989.
Zhao-Emonet et al., *Biochim. Biophys. Acta,* 1442 (2-3):109-119, 1998.
Zheng et al., *J. Gen. Virol.,* 80 (Pt 7):1735-1742, 1999.
Zhou et al., *Exp. Hematol,* 21:928-933, 1993.
Zufferey et al., *Nat. Biotechnol.,* 15 (9):871-875, 1997.

What is claimed is:

1. An isolated polynucleotide encoding a polypeptide having the amino acid sequence of SEQ ID NO:1, said sequence operably linked to a heterologous promoter.

2. The polynucleotide of claim 1, wherein said polynucleotide has the nucleic acid sequence of SEQ ID NO:2 or a complement thereof.

3. The polynucleotide of claim 2, wherein said heterologous promoter is operable in eukaryotic cells.

4. The polynucleotide of claim 3, wherein said promoter is selected from the group consisting of hsp68, SV40, CMV IE, MKC, GAL4$_{UAS}$, HSV and β-actin.

5. The polynucleotide of claim 4, wherein said promoter is a tissue specific promoter.

* * * * *

UNITED STATES PATENT AND TRADEMARK OFFICE
CERTIFICATE OF CORRECTION

| | | |
|---|---|---|
| PATENT NO. | : 7,576,191 B2 | Page 1 of 1 |
| APPLICATION NO. | : 11/519193 | |
| DATED | : August 18, 2009 | |
| INVENTOR(S) | : Liang et al. | |

It is certified that error appears in the above-identified patent and that said Letters Patent is hereby corrected as shown below:

On the Title page,

[*] Notice:    Subject to any disclaimer, the term of this patent is extended or adjusted under 35 USC 154(b) by 0 days.

Delete the phrase "by 0 days" and insert -- by 43 days --

Signed and Sealed this

Thirtieth Day of March, 2010

David J. Kappos
*Director of the United States Patent and Trademark Office*

SEQUENCE LISTING

```
<160> NUMBER OF SEQ ID NOS: 3

<210> SEQ ID NO 1
<211> LENGTH: 178
<212> TYPE: PRT
<213> ORGANISM: Homo sapiens

<400> SEQUENCE: 1

Met Asp Arg Pro Gly Pro Gly Ser Ala Arg Pro Gly Arg Thr Val His
1               5                   10                  15

Val Trp Gly Tyr Arg Val Glu Trp Lys Val Arg Asn Gly Arg Lys Leu
                20                  25                  30

Gln Pro Ser Glu Trp Ala Gly Arg Gly Asp Leu Gly Gly Phe Lys Arg
            35                  40                  45

Arg Trp Lys Asp Thr Arg Ala Thr Val Gly Thr Thr Phe Arg Arg Arg
    50                  55                  60

Ser Arg Val Ser Leu Val Gly Glu Leu Ser Lys Phe Pro Leu Pro Ser
65                  70                  75                  80

Asp Ser Ser Gly Gly Lys Ser Ser Ser Phe Ala Arg Gly Ala Leu
                85                  90                  95

Ala Trp Cys Arg Gln Arg Asn Pro Asn Pro Ser Cys Ala Ala Ala Glu
                100                 105                 110

Thr Gly Ala Arg Thr Ser Leu Pro Lys Glu Arg Cys Arg Gly Trp Arg
            115                 120                 125

Leu Gly Asn Trp Leu His Lys His Pro His Pro Asn Thr Cys Pro Arg
    130                 135                 140

Leu Pro Ala Cys Trp Leu Pro Pro Ile Leu Thr Glu Arg Gly Glu Arg
145                 150                 155                 160

Val Pro Lys Leu Val Pro Leu Leu Ala Cys Tyr Pro Lys Ser Lys Pro
                165                 170                 175

Lys Asp

<210> SEQ ID NO 2
<211> LENGTH: 537
<212> TYPE: DNA
<213> ORGANISM: Homo sapiens

<400> SEQUENCE: 2
```

```
atggatcgcc cggggccagg ctccgcgcgc cccggccgga ccgtgcacgt ttggggttac     60
cgggttgagt ggaaagtacg gaacggtagg aagctgcagc ccagcgagtg ggcggggcga    120
ggagacctag gagggttcaa aaggaggtgg aaggatacac gggccacagt cggaactact    180
ttccgaagga ggtcacgtgt gtccctagtt ggggaacttt ccaaattccc actccccagt    240
gatagctccg gaggcaagtc gtcttcttcc tttgctcggg gtgctcttgc ctggtgcagg    300
cagcggaacc ccaacccttc ctgcgccgcg gcggaaacag gggctcggac cagcctcccg    360
aaggagcgct gtcggggctg gcgcttgggg aactggttac acaagcaccc acatccaaac    420
acgtgccccc gcctccccgc ctgctggctg ccgccgattc ttacagaacg cggggagaga    480
gtccccaaac tggtgccact cctcgcctgc taccctaaga gcaagccaaa ggactga      537

<210> SEQ ID NO 3
<211> LENGTH: 193
<212> TYPE: DNA
<213> ORGANISM: Homo sapiens

<400> SEQUENCE: 3
agggcagggg gcggtaggag ggggcagagc ggtagctctg ggtgcgagcg cagagtcccc     60
aagccgcagg ctctactgag catgcccagt gtagctgcct ggggcttgct cgggccggtt    120
cccagccgcc agcctgcagc tgcacttgct gcggcttttg cagcaacgcg aggcgaggat    180
aacgagctaa gcc                                                       193
```